US012215344B2

(12) United States Patent
Levin et al.

(10) Patent No.: US 12,215,344 B2
(45) Date of Patent: Feb. 4, 2025

(54) ENGINEERED MULTICELLULAR CILIATED ORGANISMS AND KINEMATIC SELF-REPLICATION THEREOF

(71) Applicants: Trustees of Tufts College, Medford, MA (US); University of Vermont, Burlington, VT (US)

(72) Inventors: Michael Levin, Beverly, MA (US); Douglas J. Blackiston, Medford, MA (US); Kelly A. McLaughlin, Medford, MA (US); Josh Bongard, Jericho, VT (US); Sam Kriegman, Burlington, VT (US)

(73) Assignees: Trustees of Tufts College, Medford, MA (US); University of Vermont, Burlington, VT (US)

( * ) Notice: Subject to any disclaimer, the term of this patent is extended or adjusted under 35 U.S.C. 154(b) by 57 days.

(21) Appl. No.: 17/647,847

(22) Filed: Jan. 12, 2022

(65) Prior Publication Data
US 2022/0220437 A1 Jul. 14, 2022

Related U.S. Application Data

(60) Provisional application No. 63/261,258, filed on Sep. 15, 2021, provisional application No. 63/136,564, filed on Jan. 12, 2021.

(51) Int. Cl.
*C12N 5/07* (2010.01)
*C12M 3/00* (2006.01)
*C12M 3/06* (2006.01)

(52) U.S. Cl.
CPC ............... *C12N 5/06* (2013.01); *C12M 21/08* (2013.01); *C12M 23/16* (2013.01)

(58) Field of Classification Search
CPC ......... C12N 5/06; C12N 5/0603; C12M 21/08
USPC ................................. 435/70.3, 325; 530/850
See application file for complete search history.

(56) References Cited

PUBLICATIONS

Salahudeen et al., "Progenitor identification and SARS-CoV-2 infection in human distal lung organoids". Nature. Dec. 2020; 588(7839):670-675. (Year: 2020).*
Blackiston et al. "A cellular platform for the development of synthetic living machines". Science Robotics. Mar. 31, 2021. (Year: 2021).*
Kriegman, Sam, et al. "A scalable pipeline for designing reconfigurable organisms." Proceedings of the National Academy of Sciences 117.4 (2020): 1853-1859.
Dale, L., and J. M. Slack. "Fate map for the 32-cell stage of Xenopus laevis." Development 99.4 (1987): 527-551.
Vandenberg, Laura N., Dany S. Adams, and Michael Levin. "Normalized shape and location of perturbed craniofacial structures in the Xenopus tadpole reveal an innate ability to achieve correct morphology." Developmental Dynamics 241.5 (2012): 863-878.
Lin, Ning, et al. "Hurricane Sandy's flood frequency increasing from year 1800 to 2100." Proceedings of the National Academy of Sciences 113.43 (2016): 12071-12075.
Liu, Yang-Yu, Jean-Jacques Slotine, and Albert-László Barabási. "Controllability of complex networks." nature 473.7346 (2011): 167-173.
Losner, Julia, Katharine Courtemanche, and Jessica L. Whited. "A cross-species analysis of systemic mediators of repair and complex tissue regeneration." NPJ Regenerative Medicine 6.1 (2021): 21.
Soreni-Harari, Michal, et al. "Multimaterial 3D printing for microrobotic mechanisms." Soft robotics 7.1 (2020): 59-67.
Maury, Carl Peter J. "Amyloid and the origin of life: self-replicating catalytic amyloids as prebiotic informational and protometabolic entities." Cellular and Molecular Life Sciences 75.9 (2018): 1499-1507.
Cheney, Nick, et al. "Unshackling evolution: evolving soft robots with multiple materials and a powerful generative encoding." ACM SIGEVOlution 7.1 (2014): 11-23.
Park, Sung-Jin, et al. "Phototactic guidance of a tissue-engineered soft-robotic ray." Science 353.6295 (2016): 158-162.
Penrose, Lionel S. "Self-reproducing machines." Scientific American 200.6 (1959): 105-117.
Wang, Qianqian, et al. "Real-time magnetic navigation of a rotating colloidal microswarm under ultrasound guidance." IEEE Transactions on Biomedical Engineering 67.12 (2020): 3403-3412.
Qu, Zhe, et al. "Towards high-performance microscale batteries: Configurations and optimization of electrode materials by in-situ analytical platforms." Energy Storage Materials 29 (2020): 17-41.
Bilodeau, R. Adam, and Rebecca K. Kramer. "Self-healing and damage resilience for soft robotics: A review." Frontiers in Robotics and AI 4 (2017): 48.
Falk, Raphael, Neta Orevi, and Bea Menzl. "A fate map of larval organs of *Drosophila* and preblastoderm determination." Nature New Biology 246.149 (1973): 19-20.
Solé, Ricard, et al. "Synthetic collective intelligence." Biosystems 148 (2016): 47-61.
Woodrick, Robert, et al. "The *Arabidopsis* embryonic shoot fate map." Development 127.4 (2000): 813-820.
Ray, Thomas S. "Evolution, complexity, entropy and artificial reality." Physica D: Nonlinear Phenomena 75.1-3 (1994): 239-263.
Ricotti, Leonardo, et al. "Biohybrid actuators for robotics: A review of devices actuated by living cells." Science robotics 2.12 (2017): eaaq0495.
Liu, S., et al. "Voxcraft-sim, a gpuaccelerated voxel-based physics engine." https://github.com/voxcraft/voxcraft-sim (2020).

(Continued)

*Primary Examiner* — Anne Marie S Wehbe
*Assistant Examiner* — Hanan Isam Abuzeineh
(74) *Attorney, Agent, or Firm* — Quarles & Brady LLP

(57) ABSTRACT

Disclosed are engineered multicellular organisms. The disclosed organisms comprise an aggregate of ciliated cells, and the organisms move when the ciliated cells are actuated. The engineered multicellular organisms also are capable of kinematic self-replication. The engineered multicellular organisms are capable of moving a plurality of dissociated ciliated cells into piles of ciliated cells which form a multicellular organism comprising an aggregate of ciliated cells which moves when the ciliated cells are actuated. Also disclosed are systems and methods for designing, preparing, and utilizing the engineered multicellular organisms.

17 Claims, 34 Drawing Sheets

(56) References Cited

PUBLICATIONS

Manicka, Santosh, and Michael Levin. "Modeling somatic computation with non-neural bioelectric networks." Scientific reports 9.1 (2019): 18612.

Manicka, Santosh, and Michael Levin. "The Cognitive Lens: a primer on conceptual tools for analysing information processing in developmental and regenerative morphogenesis." Philosophical Transactions of the Royal Society B 374.1774 (2019): 20180369.

Sokol, S., and D. A. Melton. "Pre-existent pattern in Xenopus animal pole cells revealed by induction with activin." Nature 351.6325 (1991): 409-411.

Toda, Satoshi, et al. "Programming self-organizing multicellular structures with synthetic cell-cell signaling." Science 361.6398 (2018): 156-162.

Schmidt, Michael D., and Hod Lipson. "Age-fitness pareto optimization." Proceedings of the 12th annual conference on Genetic and evolutionary computation. 2010.

Schmidt, Michael, and Hod Lipson. "Distilling free-form natural laws from experimental data." science 324.5923 (2009): 81-85.

Studer, Gregory, and Hod Lipson. "Spontaneous emergence of self-replicating structures in molecube automata." Proc. of the 10th Int. Conf. on the Simulation and Synthesis of Living Systems (Artificial Life X), MIT Press, Cambridge, MA. 2006.

Ariizumi, Takashi, et al. "Isolation and differentiation of Xenopus animal cap cells." Current protocols in stem cell biology 9.1 (2009): 1D-5.

Tank, Elizabeth MH, et al. "Prion protein repeat expansion results in increased aggregation and reveals phenotypic variability." Molecular and cellular biology 27.15 (2007): 5445-5455.

Webster, Victoria A., et al. "3D-printed biohybrid robots powered by neuromuscular tissue circuits from Aplysia californica." Biomimetic and Biohybrid Systems: 6th International Conference, Living Machines 2017, Stanford, CA, USA, Jul. 26-28, 2017, Proceedings 6. Springer International Publishing, 2017.

Walentek, Peter. "Manipulating and analyzing cell type composition of the Xenopus mucociliary epidermis." Xenopus: Methods and Protocols (2018): 251-263.

Wu, Qirui, et al. "Organ-on-a-chip: Recent breakthroughs and future prospects." Biomedical engineering online 19 (2020): 1-19.

Dong, Xiaoguang, and Metin Sitti. "Controlling two-dimensional collective formation and cooperative behavior of magnetic microrobot swarms." The International Journal of Robotics Research 39.5 (2020): 617-638.

Hatada, Yohko, and Claudio D. Stern. "A fate map of the epiblast of the early chick embryo." Development 120.10 (1994): 2879-2889.

Zykov, Victor, et al. "Self-reproducing machines." Nature 435.7039 (2005): 163-164.

Yu, Jiangfan, et al. "Ultra-extensible ribbon-like magnetic microswarm." Nature communications 9.1 (2018): 3260.

Neumann, J. von. "Theory of self-reproducing automata." Mathematics of Computation 21 (1966): 745.

International Search Report in PCT/US2022/076484.

Bongso, Ariff, and Mark Richards. "History and perspective of stem cell research." Best practice & research Clinical obstetrics & gynaecology 18.6 (2004): 827-842.

Redkar, Abhay, Michael Montgomery, and Judith Litvin. "Fate map of early avian cardiac progenitor cells." (2001): 2269-2279.

Servant, Ania, et al. "Controlled in vivo swimming of a swarm of bacteria-like microrobotic flagella." Advanced Materials 27.19 (2015): 2981-2988.

Urrios, Arturo, et al. "A synthetic multicellular memory device." ACS synthetic biology 5.8 (2016): 862-873.

Adams, Bryant, and Hod Lipson. "A universal framework for analysis of self-replication phenomena." Entropy 11.2 (2009): 295-325.

Gallagher, Betty C., Alexandra M. Hainski, and Sally A. Moody. "Autonomous differentiation of dorsal axial structures from an animal cap cleavage stage blastomere in Xenopus." Development 112.4 (1991): 1103-1114.

Williams, Brian J., et al. "A self-propelled biohybrid swimmer at low Reynolds number." Nature communications 5.1 (2014): 3081.

Zhang, Boyang, et al. "Advances in organ-on-a-chip engineering." Nature Reviews Materials 3.8 (2018): 257-278.

Benjamini, Yoav, and Yosef Hochberg. "Controlling the false discovery rate: a practical and powerful approach to multiple testing." Journal of the Royal statistical society: series B (Methodological) 57.1 (1995): 289-300.

Blackiston, Douglas, et al. "A cellular platform for the development of synthetic living machines." Science Robotics 6.52 (2021): eabf1571.

Boer, Matthias M., Víctor Resco de Dios, and Ross A. Bradstock. "Unprecedented burn area of Australian mega forest fires." Nature Climate Change 10.3 (2020): 171-172.

Anderson, Claire, and Claudio D. Stern. "Organizers in development." Current topics in developmental biology 117 (2016): 435-454.

Kimmel, Charles B., R. M. Warga, and T. F. Schilling. "Origin and organization of the zebrafish fate map." Development 108.4 (1990): 581-594.

Alcântara, Carlos CJ, et al. "3D fabrication of fully iron magnetic microrobots." Small 15.16 (2019): 1805006.

Cvetkovic, Caroline, et al. "Three-dimensionally printed biological machines powered by skeletal muscle." Proceedings of the National Academy of Sciences 111.28 (2014): 10125-10130.

Chirikjian, Gregory S. "Parts entropy and the principal kinematic formula." 2008 IEEE International Conference on Automation Science and Engineering. IEEE, 2008.

Chirikjian, Gregory S., Yu Zhou, and Jackrit Suthakorn. "Self-replicating robots for lunar development." IEEE/ASME transactions on mechatronics 7.4 (2002): 462-472.

Chou, Hui-Hsien, and James A. Reggia. "Emergence of self-replicating structures in a cellular automata space." Physica D: Nonlinear Phenomena 110.3-4 (1997): 252-276.

Wettstein, Daniel A., David L. Turner, and Chris Kintner. "The Xenopus homolog of Drosophila Suppressor of Hairless mediates Notch signaling during primary neurogenesis." Development 124.3 (1997): 693-702.

Blackiston, Douglas, Laura N. Vandenberg, and Michael Levin. "High-throughput Xenopus laevis immunohistochemistry using agarose sections." Cold Spring Harbor Protocols 2010.12 (2010): pdb-prot5532.

Avci, Ebubekir, Maria Grammatikopoulou, and Guang-Zhong Yang. "Laser-printing and 3D optical-control of untethered microrobots." Advanced Optical Materials 5.19 (2017): 1700031.

Ebrahimkhani, Mo R., and Michael Levin. "Synthetic living machines: A new window on life." Iscience 24.5 (2021): 102505.

Emanuel, Kerry. "Increasing destructiveness of tropical cyclones over the past 30 years." Nature 436.7051 (2005): 686-688.

Baluška, Frantiek, and Michael Levin. "On having no head: cognition throughout biological systems." Frontiers in psychology 7 (2016): 902.

Keijzer, Fred, Marc Van Duijn, and Pamela Lyon. "What nervous systems do: early evolution, input-output, and the skin brain thesis." Adaptive Behavior 21.2 (2013): 67-85.

Adam, Georges, et al. "Towards functional mobile microrobotic systems." Robotics 8.3 (2019): 69.

Rossi, Giuliana, Andrea Manfrin, and Matthias P. Lutolf. "Progress and potential in organoid research." Nature Reviews Genetics 19.11 (2018): 671-687.

Gao, Wei, et al. "Flexible electronics toward wearable sensing." Accounts of chemical research 52.3 (2019): 523-533.

Garreta, Elena, et al. "Rethinking organoid technology through bioengineering." Nature materials 20.2 (2021): 145-155.

Gilbert, Scott F., and Sahotra Sarkar. "Embracing complexity: organicism for the 21st century." Developmental dynamics: an official publication of the American Association of Anatomists 219.1 (2000): 1-9.

Griffith, Saul, Dan Goldwater, and Joseph M. Jacobson. "Self-replication from random parts." nature 437.7059 (2005): 636-636.

(56) References Cited

PUBLICATIONS

Sive, Hazel L., Robert M. Grainger, and Richard M. Harland. "Animal cap isolation from Xenopus laevis." Cold Spring Harbor Protocols 2007.6 (2007): pdb-prot4744.

Xie, Hui, et al. "Reconfigurable magnetic microrobot swarm: Multimode transformation, locomotion, and manipulation." Science robotics 4.28 (2019): eaav8006.

Han, Yu, et al. "Mesenchymal stem cells for regenerative medicine." Cells 8.8 (2019): 886.

Hiller, Jonathan, and Hod Lipson. "Dynamic simulation of soft multimaterial 3d-printed objects." Soft robotics 1.1 (2014): 88-101.

Huh, Dongeun, et al. "Reconstituting organ-level lung functions on a chip." Science 328.5986 (2010): 1662-1668.

Hussey, George S., Jenna L. Dziki, and Stephen F. Badylak. "Extracellular matrix-based materials for regenerative medicine." Nature Reviews Materials 3.7 (2018): 159-173.

Bruss, Isaac R., and Sharon C. Glotzer. "Curvature-induced microswarming." Soft matter 13.30 (2017): 5117-5121.

Green, Jeremy. "The animal cap assay." Molecular methods in developmental biology: Xenopus and zebrafish (1999): 1-13.

Sung, Jong Hwan, et al. "Recent advances in body-on-a-chip systems." Analytical chemistry 91.1 (2018): 330-351.

Hiller, Jonathan, and Hod Lipson. "Automatic design and manufacture of soft robots." IEEE Transactions on Robotics 28.2 (2011): 457-466.

Stubbs, Jennifer L., et al. "Radial intercalation of ciliated cells during Xenopus skin development." (2006): 2507-2515.

Mustard, Jessica, and Michael Levin. "Bioelectrical mechanisms for programming growth and form: taming physiological networks for soft body robotics." Soft Robotics 1.3 (2014): 169-191.

Wiedenmann, Jörg, et al. "EosFP, a fluorescent marker protein with UV-inducible green-to-red fluorescence conversion." Proceedings of the National Academy of Sciences 101.45 (2004): 15905-15910.

Jacobson, Homer. "On models of reproduction." American Scientist 46.3 (1958): 255-284.

Jones, E. A., and H. R. Woodland. "Development of the ectoderm in Xenopus: tissue specification and the role of cell association and division." Cell 44.2 (1986): 345-355.

Stanley, Kenneth O. "Compositional pattern producing networks: A novel abstraction of development." Genetic programming and evolvable machines 8 (2007): 131-162.

Kamm, Roger D., et al. "Perspective: The promise of multi-cellular engineered living systems." APL bioengineering 2.4 (2018): 040901.

Kim, Hye Young, et al. "Tissue mechanics drives regeneration of a mucociliated epidermis on the surface of Xenopus embryonic aggregates." Nature communications 11.1 (2020): 665.

Kim, Young Duck, et al. "Bright visible light emission from graphene." Nature nanotechnology 10.8 (2015): 676-681.

* cited by examiner

ENGINEERED MULTICELLULAR CILIATED ORGANISMS AND KINEMATIC SELF-REPLICATION THEREOF

CROSS-REFERENCE TO RELATED PATENT APPLICATIONS

The present application claims the benefit of priority under 35 U.S.C. § 119(e) to U.S. Provisional Application No. 63/136,564, filed on Jan. 12, 2021, and U.S. Provisional Application No. 63/261,258, filed on Sep. 15, 2021, the contents of which are incorporated herein by reference in their entireties.

STATEMENT REGARDING FEDERALLY SPONSORED RESEARCH OR DEVELOPMENT

This invention was made with government support under grant HR0011-18-2-0022 awarded by the Department of Defense. The government has certain rights in the invention.

BACKGROUND

The field of the invention relates to engineered multicellular organisms and systems and methods for designing, preparing, and utilizing engineered multicellular organisms. The engineered multicellular organisms may be configured for movement and other physical and biological activities.

Here, we introduce "Xenobots," which are multicellular biological robots ("biobots") from frog (*Xenopus laevis*) with a diameter ranging from 100 to 500 microns. Xenobots have a built-in capacity for motility in aqueous environments based on locomotive appendages called "cilia" which cover their surface. Xenobots are induced to arise by cellular self-organization and do not require scaffolds or microprinting, and the amphibian cells which form Xenobots are highly amenable to surgical, genetic, chemical, and optical stimulation to control the self-assembly process. Xenobots are motile and are capable of moving in various trajectories including loops, straight lines, large arcs, and even in zigzag patterns with a linear speed ranges from 5-50 microns/second.

Because Xenobots develop on their own without the need for external manipulation or micromanagement, many of them can be grown in parallel. This makes Xenobots amenable to easy mass fabrication, which not only makes their production more scalable and economical, but also enables easy generation of Xenobots swarms that may collectively accomplish task that cannot be accomplished by a single Xenobot. Furthermore, Xenobots can be loaded with exogenous payloads such as RNA, protein, drugs, dyes, and synthetic molecules. Therefore, Xenobots can be programmed on demand to execute a diverse set of tasks in different environments.

Recently, we have found that semitoroidal shaped ("Pac Man" shape) xenobots are capable of kinematic self replication. We also found that xenobots can push individual frog cells into piles. The cells in these piles attach together and grow cilia—small motion-propelling hairs on the pile's outer face.

Making functional self copies of oneself by amassing and organizing external material through motion is known as kinematic self replication. This differs from growth-based replication, the standard form of propagation in biology.

We have observed that a swarm of semitoroids can trigger five rounds of this replicative process before losing the ability to self-replicate, if supplied with enough frog cells as construction material. It should be possible to keep this process going indefinitely if sufficient quantities of cells are provided. Further, starting with just a few starter semitoroids, a very large number of xenobots can be created automatically, thus classing this technology as an exponential technology. We have shown that, in theory, these swarms are capable of performing exponentially increasing amounts of useful work at the microscale, such as building and fixing microelectronics, or cleaning contaminants from soils and waterways.

SUMMARY

Disclosed are engineered multicellular organisms. The disclosed organisms comprise or consist of relatively small aggregates of ciliated cells, and the organisms move when the ciliated cells are actuated.

The engineered multicellular organisms also are capable of kinematic self-replication. The engineered multicellular organisms are capable of moving a plurality of dissociated ciliated cells into piles of ciliated cells which form a multicellular organism comprising an aggregate of ciliated cells which moves when the ciliated cells are actuated. Also disclosed are systems and methods for designing, preparing, and utilizing the engineered multicellular organisms.

DETAILED DESCRIPTION

Figure 1:
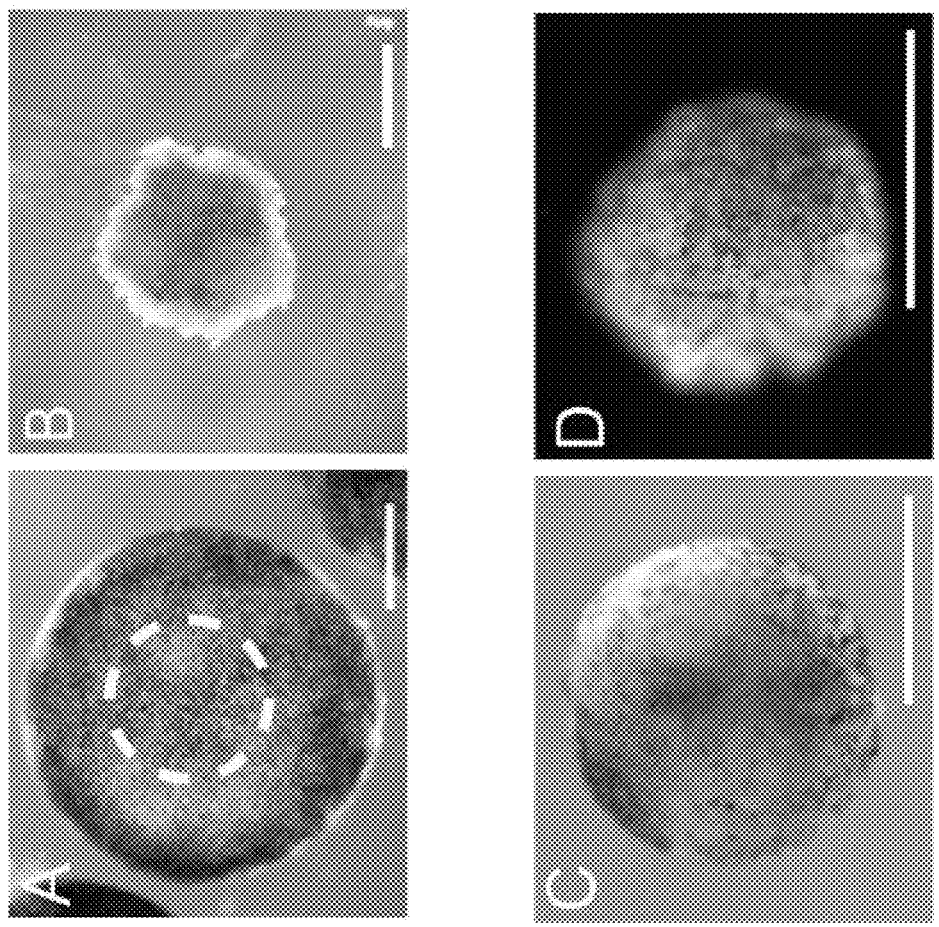
FIG. 1. *Xenopus* embryonic explants create a mobile living machine. (A) Tissue is harvested from the animal hemisphere of a Nieuwkoop and Faber stage 9 *Xenopus laevis* embryo. (B) Explants are then moved to a 0.75×MMR solution and inverted during healing. (C) After 30 minutes explants heal into a spherical ball of presumptive ectoderm. (D) Four days after formation, explants differentiate into irregular epidermis and are selected for experimentation. (E) Time-lapse imaging reveals that explants are mobile when observed in an aqueous environment, with rotational biases observed when tracked for longer time periods (E'). (F) Motion is produced by multi-ciliated cells present on the surface of the explant, visualized with anti-acetylated tubulin immunohistochemistry, and multiciliated cell differentiation can be removed though the overexpression of the intracellular domain of Notch (NotchICD) (F'). (G) Multi-ciliated cells are also present on the epidermis of age-matched embryos and can likewise be inhibited through overexpression of NotchICD (G'). Quantification of multi-ciliated cells per 500 μM diameter region in each of the conditions. (H) Both wild type (I, I') and NotchICD expressing explants (J, J') have a lifespan of approximately 9 days in standard 0.75×MMR, with movement observed across all days of testing for wild type explants. (K) Average velocity μm/s over time. Error bars indicate ±1 SD. Scale bars are 500 μM.
Figure 1:
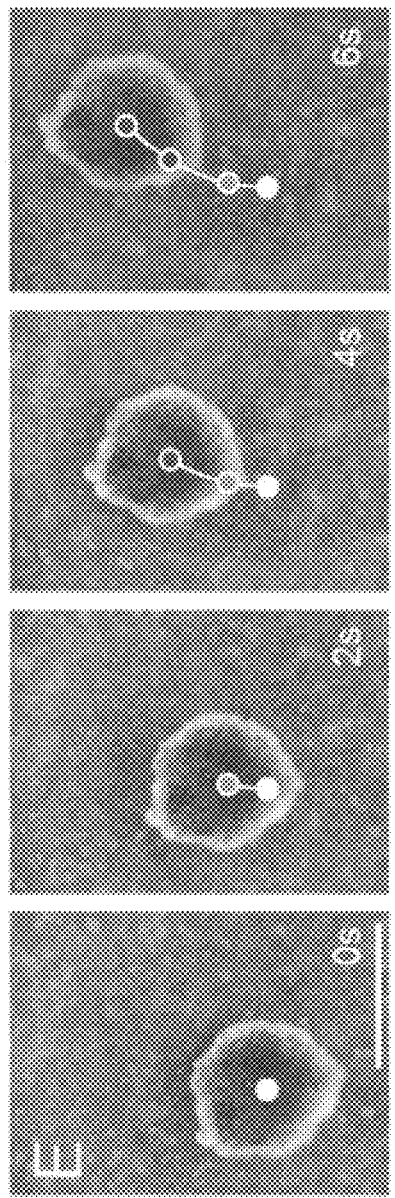
Figure 1:
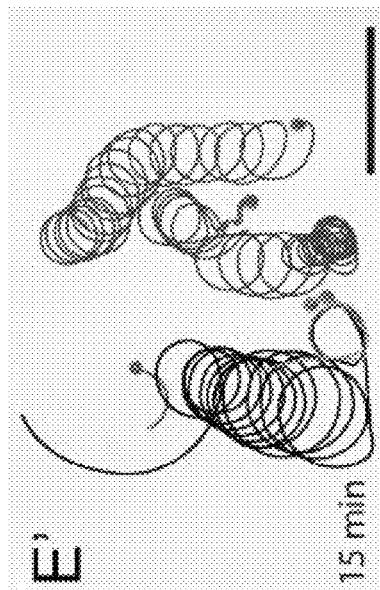
Figure 1:
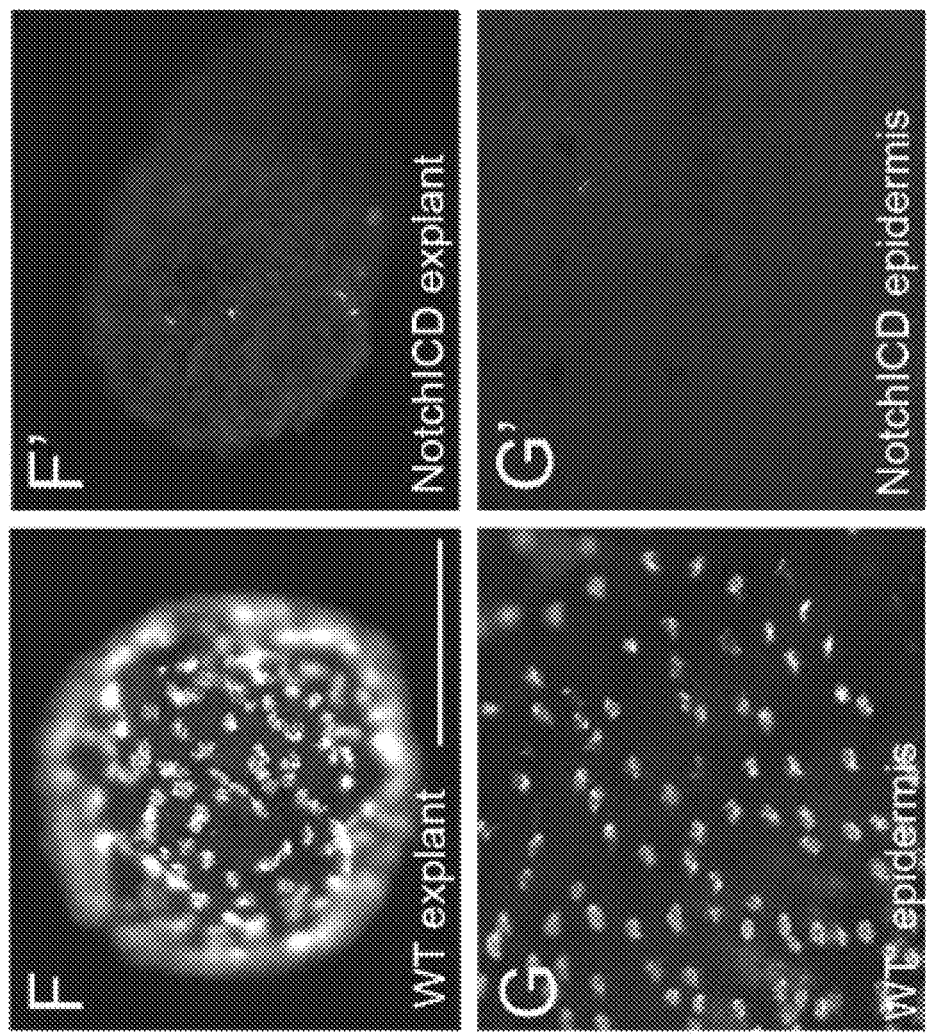
Figure 1:
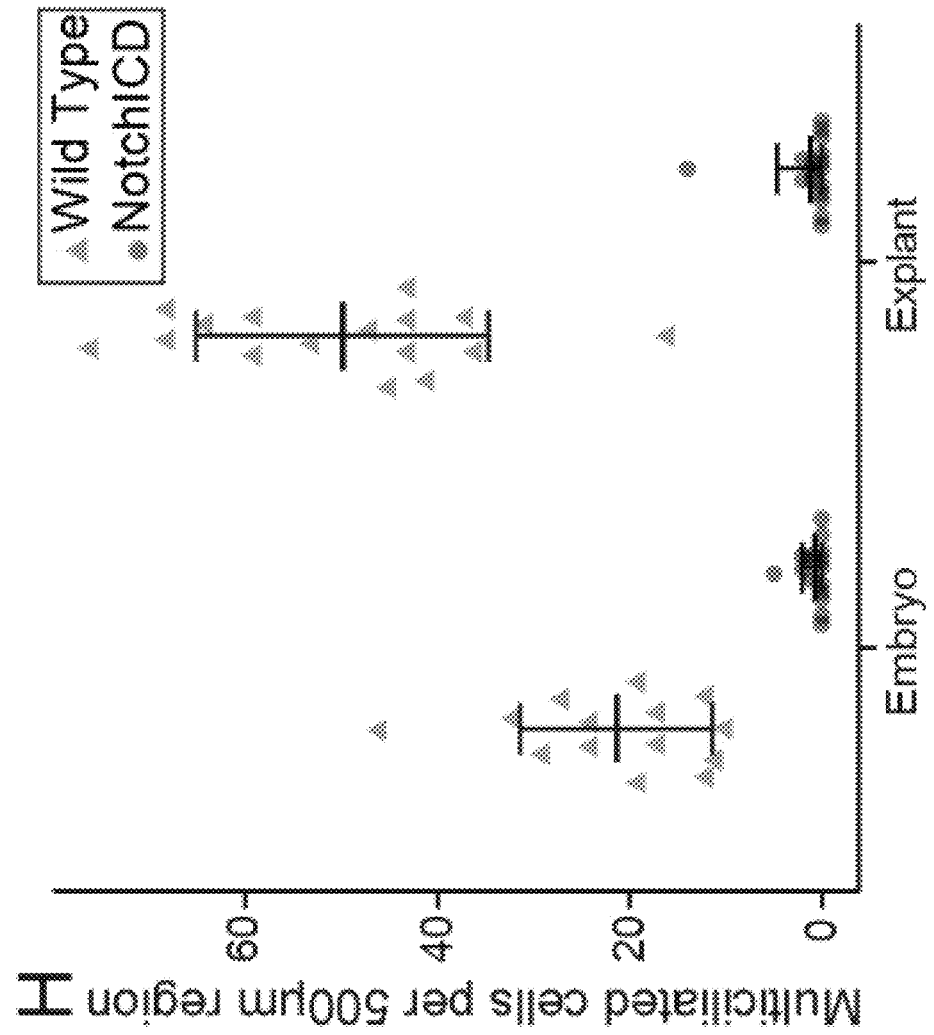
Figure 1:
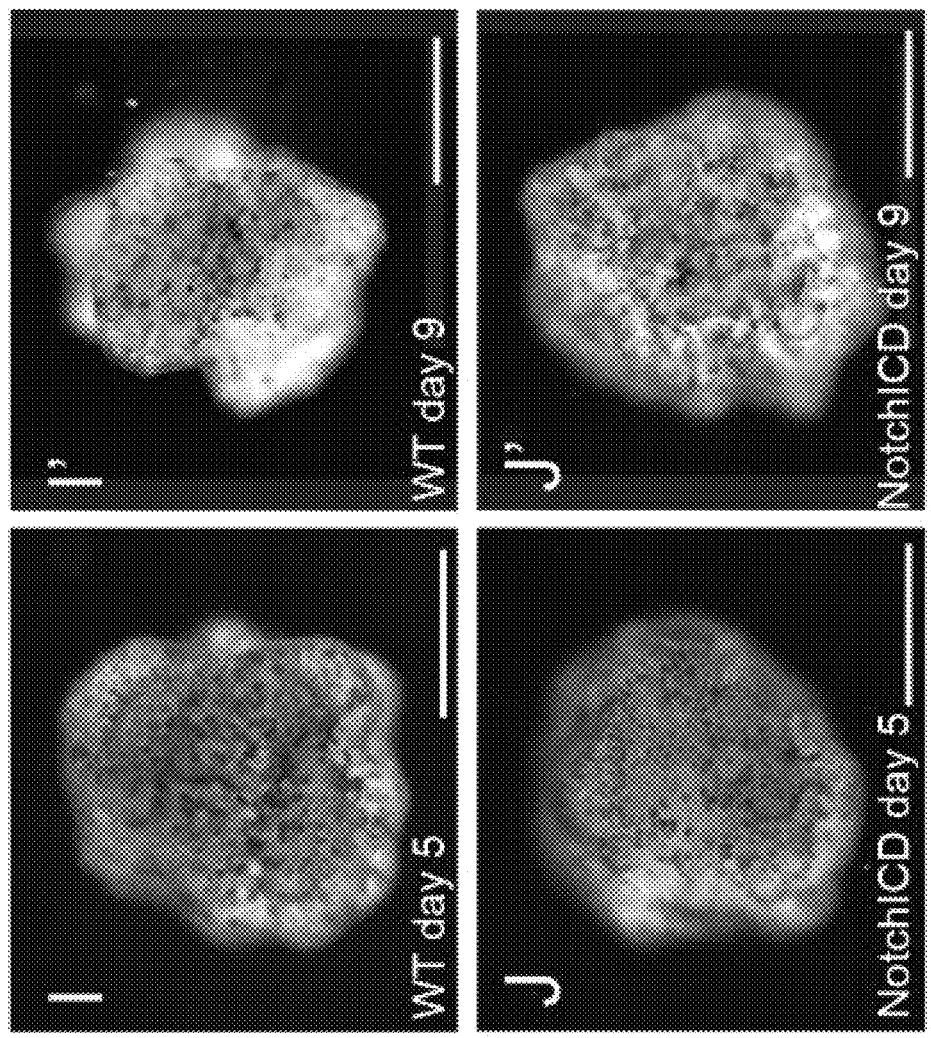
Figure 1:
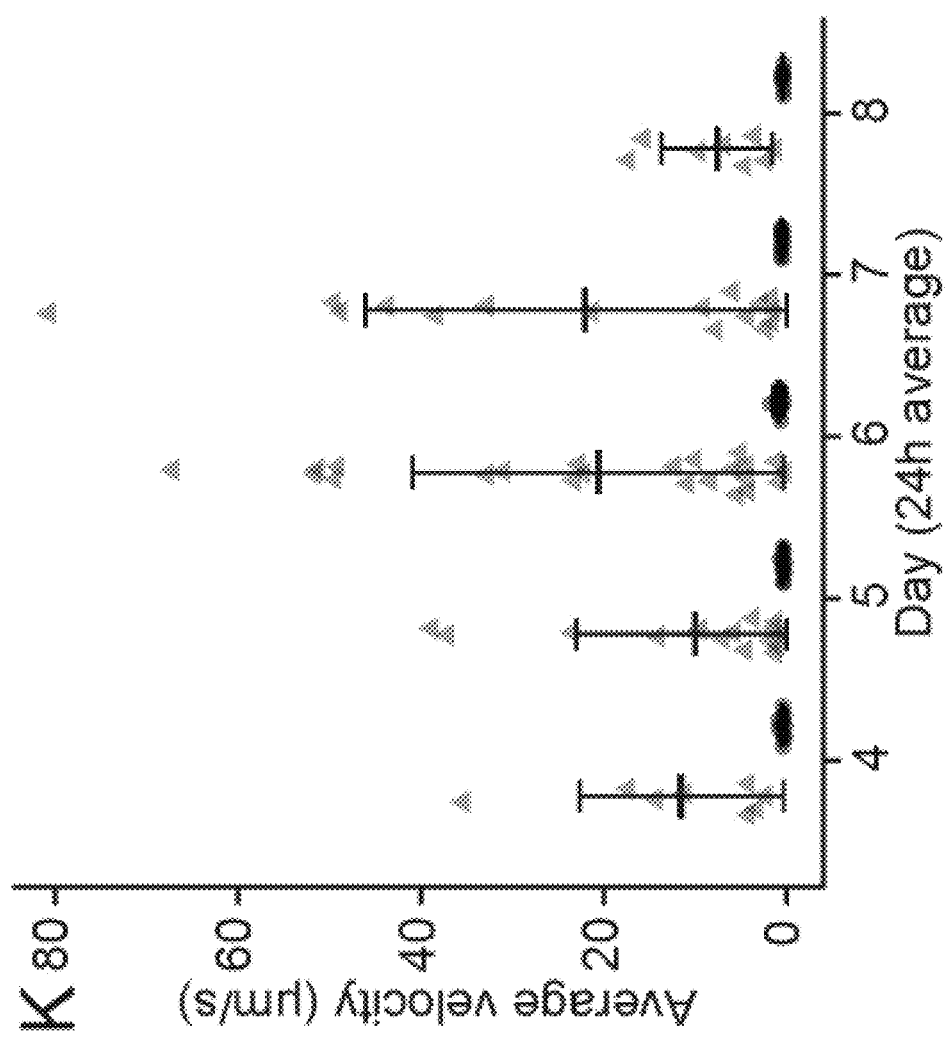

The following discussion is presented to enable a person skilled in the art to make and use embodiments of the disclosure. Various modifications to the illustrated embodiments will be readily apparent to those skilled in the art, and the generic principles herein can be applied to other embodiments and applications without departing from embodiments of the disclosure. Thus, embodiments of the disclosure are not intended to be limited to embodiments shown, but are to be accorded the widest scope consistent with the principles and features disclosed herein. The following detailed description is to be read with reference to the figures. The figures, which are not necessarily to scale, depict selected embodiments and are not intended to limit the scope of embodiments of the disclosure. Skilled artisans will recognize the examples provided herein have many useful alternatives and fall within the scope of embodiments of the disclosure.

Definitions and Terminology

Disclosed are engineered multicellular organisms and systems and methods designing, preparing, and utilizing the engineered multicellular organisms. The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a cell" should be interpreted to mean "one or more cells." As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

Engineered Multicellular Organisms

Disclosed are engineered multicellular organisms. The disclosed organisms comprise an aggregate of ciliated cells, and the organisms move when the ciliated cells are actuated. Also disclosed are systems and methods for designing, preparing, and utilizing the engineered multicellular organisms.

The engineered multicellular organisms typically comprise an aggregate of ciliated cells (e.g., an aggregate of multiciliated cells). In some embodiments, the aggregate of cells comprises, consists essentially of, or consists of epidermal cells, such as ciliated epidermal cells. Suitable ciliated cells may include, but are not limited to, ciliated cells derived from ectoderm (e.g., differentiated ectodermal cells).

Ciliated cells for use in preparing the disclosed engineered multicellular organisms may include ciliated cells which are non-motile in their native condition or tissue but which are motile in the engineered multicellular organisms. The cilia of the ciliated cells utilized for forming the disclosed engineered multicellular organisms may be motile cilia, in contrast to non-motile primary cilia. Motile cilia of ciliated cells utilized to form the disclosed engineered multicellular organisms may include an axoneme as known in the art to actuate motility.

Optionally, the engineered multicellular organisms may meet at least one of the following criteria: (i) the organism comprises less than about 1000 total cells, or less than about 900, 700, 600, 500, 400, 300, 200, or 100 cells (or the organism comprises a number of cells within a range bounded by any of these values (e.g., 100-1000 cells); and (ii) the organism has an effective diameter of less than about 2 mm, or less than about 1.5 mm, 1.0 mm, 0.9 mm, 0.8 mm, 0.7 mm, 0.6 mm, 0.5 mm, 0.4 mm, 0.3 mm, 0.2 mm, or 0.1 mm (or the organism has an effective diameter within a size range bounded by any of these values (e.g., 0.1-0.5 mm).

The engineered multicellular organisms preferably are self-motile and move when the cilia of the organisms are actuated. In some embodiments, the cilia of the organisms may be actuated by electrical stimulation or optogenetics where the cilia have been genetically modified to express light-sensitive ion channels.

In some embodiments, the engineered multicellular organisms move when the cilia of the organisms are actuated. Preferably, the organisms move at a rate of at least about 1, 2, 3, 4, 5, 10, 15, 20, 25, 30, 35, 40, 45, 50, 100, 200, 500, or 1000 microns/second or faster when the cilia of the organisms are actuated.

Preferably, the engineered multicellular organism have a self-limiting life-span when placed in an physiologically suitable environment of at least about 3, 4, 5, 6, 7, 8, 9, 10, 11, 12, 13, 14, 15, 16, 17, 18, 19, 20, 21, 22, 23, 24, 25, 26, 27, 28, 29, or 30 days.

The engineered multicellular organisms comprise an aggregate of cells which may be referred to as a plurality of living cells that are cohered to one another. The aggregate of cells forms a three-dimensional shape which shape may change over time.

The aggregate of cells of the disclosed organism may comprise selected cell types. Suitable cell types may include, but are not limited to, ciliated cells such as ciliated epidermal cells. Suitable ciliated cells may include, but are not limited to ciliated cells of derived from ectoderm (e.g., differentiated ectodermal cells). Suitable cell types may include epithelial cells of the bronchi and oviducts.

Suitable cells may comprise animal cells. Suitable animal cells may comprise amphibian cells (e.g., frog cells and the like) or mammalian cells (e.g., human cells, mouse cells, rat cells, and the like). Suitable cells may include cells that have been cultured in vitro.

The aggregate of cells may comprise, consist essentially of, or consist of ciliated cells. In some embodiments, the aggregate of cells may comprise or may not comprise additional non-ciliated cell types.

In some embodiments, the engineered multicellular organisms are non-innervated (e.g., the organisms do not comprise neural cells or neural tissue) and/or or non-cartilaginous. The multicellular organisms may be described as "engineered" because they are different from naturally occurring organism that arise without the guidance of human ingenuity and modifications. In other words, the multicellular organisms are synthetic and non-naturally occurring, albeit the multicellular organism may utilize endogenous cell:cell signaling and morphogenesis.

The aggregate of cells of the engineered multicellular organisms may comprise cells that have been engineered to express a heterologous molecule. In some embodiments, the cells of the organisms are engineered to express a heterologous protein or secrete specific desired molecules.

In embodiments in which the aggregate of cells comprises cells that have been engineered to express a heterologous molecule, suitable heterologous molecules that are expressed may include enzymes. Suitable enzymes may include enzymes that metabolize a target substrate, which may include toxins. Other suitable heterologous molecules may include receptors for a target ligand (e.g., a target ligand sensed by the organism), or sensors of light, heat, and other physical properties in the environment. Other suitable heterologous molecules may include reporter molecules (e.g., photoconvertible fluorescent reporter molecules).

The disclosed engineered multicellular organisms may be self-repairing. In some embodiments, if the aggregate of cells is subjected to deaggregation (e.g., physical damage that disrupts aggregation of the cells), the cells will reaggregate and/or remodel to re-form the aggregate of cells having the original shape or a new shape.

The engineered multicellular organisms may be configured in order to perform tasks. For example, the engineered multicellular organisms may be configured structurally and/or genetically.

In some embodiments, the organism is configured for moving a target object (e.g., by pushing a target object). In further embodiments, the organism is configured for moving target objects (e.g., by pushing target objects) and collecting the moved target objections (i.e., aggregating the target objects).

The engineered multicellular organisms may be configured to have a cavity. In some embodiments, the engineered multicellular organisms are configured to have a cavity for capturing and/or transporting a target object.

The engineered multicellular organisms may be utilized in a number of applications. In some embodiments, the engineered multicellular organisms are utilized in methods for removing a target substrate from an environment (e.g., a toxin from an environment). The methods may comprise engineering the organisms to express an enzyme that metabolizes the target substrate and placing the organism in the environment to remove the target substrate from the environment.

In other embodiments, the engineered multicellular organisms are utilized in methods for detecting a target ligand in a sample. The methods may comprise engineering the organisms to express a receptor for the target ligand and place the organism in the sample, where the organism generates a signal after the receptor binds the target ligand.

In other embodiments, the engineered multicellular organisms may express a photoconvertible fluorescent reporter molecule, and the organism generates a fluorescent signal when the photoconvertible fluorescent reporter molecule is exposed to light. As such, the activity and movement of the organisms may be monitored by placing the organisms in an environment and providing a light source for activating the photoconvertible fluorescent reporter molecule.

Also disclosed are methods for preparing the engineered multicellular organisms. In some embodiments, the methods comprising explanting cells from tissue and culturing the explanted cells under conditions in which the cultured, explanted cells form the engineered multicellular organisms.

ILLUSTRATIVE EMBODIMENTS

The following embodiments are illustrative and should not be interpreted to limit the scope of the claimed subject matter.

Embodiment 1. An engineered multicellular organism comprising an aggregate of ciliated cells, wherein the organism moves when the ciliated cells are actuated.

Embodiment 2. The organism of embodiment 1, wherein the organism consists of biological material and/or does not comprise any inorganic material, for example as a scaffold.

Embodiment 3. The organism of embodiment 1 or 2, wherein the organism comprises a sensor for detecting a target molecule.

Embodiment 4. The organism of any of the foregoing embodiments, wherein the cells of the organism self-assemble.

Embodiment 5. The organism of any of the foregoing embodiments, wherein the organism has an effective diameter of about 100-500 microns.

Embodiment 6. The organism of any of the foregoing embodiments, wherein the organism moves at a rate of at least about 15, 20, 25, 50, 100, 200, 500, or 1000 microns/second when the ciliated cells are actuated.

Embodiment 7. The organism of any of the foregoing embodiments, wherein the organism does not comprise neural cells or neural tissue.

Embodiment 8. The organism of any of the foregoing embodiments, wherein the ciliated cells are eukaryotic epidermal cells.

Embodiment 9. The organism of any of the foregoing embodiments, wherein the ciliated cells are engineered to express a heterologous molecule.

Embodiment 10. The organism of embodiment 9, wherein the heterologous molecule is a reporter molecule (e.g., a photoconvertible fluorescent reporter molecule).

Embodiment 11. The organism of embodiment 9, wherein the heterologous molecule is an enzyme that metabolizes a target substrate (e.g., a toxin).

Embodiment 12. The organism of embodiment 9, wherein the heterologous molecule is a receptor for a target ligand (e.g., a target ligand sensed by the organism).

Embodiment 13. The organism of any of the foregoing embodiments, wherein the aggregate of cells reaggregates after the aggregate is subjected to deaggregation (i.e., the organism self-repairs).

Embodiment 14. The organism of any of the foregoing embodiments, wherein the organism is configured for moving a target object, optionally wherein the organism comprises a hole or cavity for holding the target object.

Embodiment 15. The organism of any of the foregoing embodiments, wherein the organism is configured to have a cavity for capturing and/or transporting a target object.

Embodiment 16. The organism of any of the foregoing embodiments, wherein the organism comprises amphibian cells.

Embodiment 17. A plurality of the organism of any of the foregoing embodiments, wherein the plurality exhibits collective and/or coordinated behavior.

Embodiment 18. The plurality of embodiment 17, wherein the collective and/or coordinated behavior is collective and/or coordinated movement.

Embodiment 19. A method for removing a target substrate from an environment, the method comprising engineering the organism of any of embodiments 1-18 or a plurality thereof to express an enzyme that metabolizes the target substrate and placing the organism in the environment.

Embodiment 20. A method for detecting a target ligand in a sample, the method comprising engineering the organism of any of embodiments 1-18 or plurality thereof to express a receptor for the target ligand and place the organism in the sample, wherein the organism generates a signal after the receptor binds the target ligand.

Embodiment 21. A method for detecting movement of an organism of any of embodiments 1-17 or a plurality thereof, wherein the organism or the plurality thereof expresses a photoconvertible fluorescent reporter molecule, and the organism generates a fluorescent signal when the photoconvertible fluorescent reporter molecule is exposed to light.

Embodiment 22. A method for preparing the engineered multicellular organism of any of embodiments 1-17 or a plurality thereof, the method comprising explanting cells from tissue and culturing the explanted cells under conditions in which the cultured, explanted cells form the engineered multicellular organism or the plurality thereof.

Embodiment 23. A system comprising an engineered multicellular organism comprising an aggregate of ciliated cells and a plurality of dissociated cells, wherein the engineered multicellular organism is capable of moving when the ciliated cells are actuated and the engineered multicellular organism moves the plurality of dissociated cells into piles of cells which form a multicellular organism comprising an aggregate of ciliated cells which is capable of moving when the ciliated cells are actuated.

Embodiment 24. The system of embodiment 23, wherein the engineered multicellular organism is semitoroidal in shape.

Embodiment 25. The system of embodiment 23 or 24, wherein the organism consists of biological material and/or does not comprise any inorganic material, for example as a scaffold.

Embodiment 26. The system of any of embodiments 23-25, wherein the cells of the organism self-assemble.

Embodiment 27. The system of any of embodiments 23-26, wherein the organism has an effective diameter of about 100-500 microns.

Embodiment 28. The system of any of embodiments 23-27, wherein the organism moves at a rate of at least about 15, 20, 25, 50, 100, 200, 500, or 1000 microns/second when the ciliated cells are actuated.

Embodiment 29. The system of any of embodiments 23-28, wherein the organism does not comprise neural cells or neural tissue.

Embodiment 30. The system of any of embodiments 23-29, wherein the ciliated cells are eukaryotic epidermal cells.

Embodiment 31. The system of any of embodiments 23-30, wherein the organism is configured for moving a target object, optionally wherein the organism comprises a hole or cavity for holding the target object.

Embodiment 32. The system of any of embodiments 23-31, wherein the organism is configured to have a cavity for capturing and/or transporting a target object.

Embodiment 33. The system of any of embodiments 23-32, wherein the organism comprises amphibian cells.

Embodiment 34. A method for forming an engineered multicellular organism comprising an aggregate of ciliated cells which is capable of moving when the ciliated cells are actuated, the method comprising combining in cell media an engineered multicellular organism comprising an aggregate of ciliated cells and a plurality of dissociated cells, wherein the engineered multicellular organism is capable of moving when the ciliated cells are actuated and the engineered multicellular organism moves the plurality of dissociated cells into piles of cells which form the multicellular organism comprising the aggregate of ciliated cells which is capable of moving when the ciliated cells are actuated.

Embodiment 35. The method of embodiment 34, wherein the engineered multicellular organism is semitoroidal in shape.

Embodiment 36. The method of embodiment 34 or 35, wherein the organism consists of biological material and/or does not comprise any inorganic material, for example as a scaffold.

Embodiment 37. The method of any of embodiments 34-36, wherein the cells of the organism self-assemble.

Embodiment 38. The method of any of embodiments 34-37, wherein the organism has an effective diameter of about 100-500 microns.

Embodiment 39. The method of any of embodiments 34-38, wherein the organism moves at a rate of at least about 15, 20, 25, 50, 100, 200, 500, or 1000 microns/second when the ciliated cells are actuated.

Embodiment 40. The method of any of embodiments 34-39, wherein the organism does not comprise neural cells or neural tissue.

Embodiment 41. The method of any of embodiments 34-40, wherein the ciliated cells are eukaryotic epidermal cells.

Embodiment 42. The method of any of embodiments 34-41, wherein the organism is configured for moving a target object, optionally wherein the organism comprises a hole or cavity for holding the target object.

Embodiment 43. The method of any of embodiments 34-42, wherein the organism is configured to have a cavity for capturing and/or transporting a target object.

Embodiment 44. The method of any of embodiments 34-43, wherein the organism comprises amphibian cells.

EXAMPLES

The following examples are illustrative and should not be interpreted to limit the scope of the claimed subject matter.

Example 1—a Cellular Platform for the Development of Synthetic Living Machines

Reference is made to Blackiston et al., "A cellular platform for the development of synthetic living machines," Sci. Robot. 2021 Mar. 31; 6(52): eabf1571. doi: 10.1126/scirobotics.abf1571, the content of which is incorporated herein by reference in its entirety.

Title—a New Cellular Platform for the Development of Synthetic Living Machines

Abstract

Robot swarms have to date been constructed from artificial materials. Motile biological constructs have been created from muscle cells grown on precisely shaped scaffolds. However, the exploitation of emergent self-organization and functional plasticity into a self-directed living machine has remained a major challenge. We report here an explant-based method for generation of in vitro biological robots from frog (*Xenopus laevis*) cells. These Xenobots exhibit coordinated locomotion via cilia present on their surface. These cilia arise through normal tissue patterning and do not require complicated construction methods or genomic editing, making biobot production amenable to high-throughput projects. The biobots arise by cellular self-organization and do not require scaffolds or microprinting; the amphibian cells are highly amenable to surgical, genetic, chemical, and optical stimulation during the self-assembly process. We show that the Xenobots can navigate aqueous environments in diverse ways, heal after damage, and show emergent group behaviors. We provide in silico simulations using evolutionary computation that explain how sensor-less behavior of Xenobots gives rise to observed manipulation of objects in their environment. In addition, we provide proof of principle for a writable molecular memory using a photoconvertible protein which can record exposure to a specific wavelength of light. Together, these results introduce a new platform that can be used to study many aspects of self-assembly, swarm behavior, and synthetic bioengineering, as well as provide versatile, soft-body living machines for numerous practical applications in biomedicine and the environment.

Introduction

Constructing robot swarms at small scales remains an open problem (1-4). Fabrication challenges abound, yet manufacturing advances are allowing for the construction of large numbers of microrobots composed of diverse components (5-7). Formulating and programming complex control policies into very small devices to enable swarm behavior also raises many conceptual challenges (8-10). However, recent advances in synthetic biology suggest an alternative path to many-bodied microswarms that, to some degree, sidestep some of these manufacturing and conceptual challenges: constructing small-scale living machines solely from biological tissue (11) in such a way that they inherit the adaptive potential of their wild type analogs. All organisms, including those that grow to macro size scales, pass through early stages of development in which they must achieve and maintain complex behaviors. This raises the possibility of direct and indirect perturbations to natural development, including tissue explantation and/or rearrangement, to achieve novel yet stable small-scale biological forms orthogonal to any found in nature. One major advantage of this approach is that living cells already possess numerous sensors, effectors, and signaling/computational circuits. Their native biochemical, biomechanical, and bioelectrical communication and control machinery can be repurposed for novel functionality at the system level and does not have to be directly engineered.

Classical developmental biology has long focused on uncovering the genes, organizing centers, and signaling cascades that drive specification of cells and tissues from undifferentiated precursors (12, 13). Historically, this research used in vivo embryonic models to examine the effects of misexpression of early patterning genes on downstream phenotypes, creating morphological and molecular fate maps in their respective native systems (14-19). A more recent effort has been directed towards harnessing the information garnered from this classical basic biology to create complex systems from the ground up in vitro. These biological robots allow investigation into diverse topics ranging from the origin of multicellularity, aspects of basal cognition, new approaches to synthetic biology, and the creation of implantable bio-prosthetics.

A recognizable example of this methodology are organoids, 3-dimensional in vitro cultured representations of complex tissues and organs that reproduce the physiology of their in vivo counterparts. Indeed, this work has revealed many mechanisms of stem cell differentiation, and has enabled investigators to drive progenitor cells to a wide array of complex tissue types with diverse anatomies including components of the eye, cerebral structures, gut, liver, intestine, mammary gland, kidney, and pancreas among others (20). Furthermore, recent advances led the to the miniaturization and daisy-chaining of multiple organoid types, leading to body-on-a-chip systems aimed at recapitulating whole-organism nested physiology (21, 22). The power of this technology enables investigators to model complex multi-organ diseases, understand drug interactions between organ systems, and better represent patient physiology compared to single organoids grown in culture. However, while these techniques further our understanding of many aspects of differentiation and self-assembly, they are designed to replicate existing in vivo systems rather than building novel morphologies. Moreover, they are largely produced by micromanaging (via bio-printing or scaffolds) cellular arrangement, and have yet to truly exploit the remarkable self-assembly and plasticity of cells in vivo (23). Similarly, they have not yet been explored for the ability to exhibit motility and interaction with changing environments. This important advance would enable the extension of physiological and biomedical studies into the emerging field of basal cognition which seeks to address the origin of computation, decision-making, and adaptive control in diverse body-plans. Developing amenable platforms for addressing this question is as crucial for understanding the evolution of brain-body complexity as they are for providing insight and biological inspiration for robotics and artificial intelligence.

Creation of novel biological forms and structures non-existent in nature is the goal of the emerging field of biorobotics. So far, efforts in this field have somewhat coalesced around biohybrid designs, combining synthetic scaffolds or components alongside living cells and tissues. These systems often use muscle actuators to drive rigid artificial body-parts, as in the case of phototaxis guided biohybrid stingray (24), micro walking and swimming biohybrids propelled by skeletal and cardiac muscle tissue (25, 26), and macroscale sea turtle like Aplysia biohybrid (27). This design approach capitalizes on the benefits of traditional robotics; synthetic components can be modeled quickly in simulation, adjusted, and fabricated with a high degree of precision. It also enables the creation of morphologies which would be difficult or impossible to produce with living tissues, including micrometer thin sheets with high rigidity, thin filaments resistant to breaking, and sharp edges. However, these synthetic components also contain the limitations of traditional robotic systems—they are unable to regenerate or self-repair, they do not possess metabolic pathways, and are generally unable undergo extensive remodeling or migration like living cells and tissues.

Instead of relying on synthetic components that specify the types of function the robot can accomplish, one could take advantage of the plasticity biology has to offer and build designs entirely out of cells and tissues, creating a fully biological machine (11). By using a combination of epidermal and cardiac muscle tissue, one can create biobots that can crawl through aqueous environments, collect debris in their immediate vicinity, and quickly heal from mechanical lacerations. While less precise in their functionality compared to biohybrids, the biobots are robust to damage and can respond to changes in their environment. These constructs are also completely self-powered, surviving ten days without additional nutrients, and are fully biodegradable, harmlessly breaking down at their end of life.

The current study expands on these fully biological machines, documenting a bottom up approach to produce synthetic living machines from cells of the frog *Xenopus laevis*. We hypothesized that when liberated from the rest of the animal, cells would self-organize into a functional morphology that was distinct from their genomically-specified default. We report here that tissue explanted from wild-type frog embryos forms synthetic constructs with fascinating morphology and behavior that are different from that of normal tadpoles. These "Xenobots" generate swimming motion through the beating of multiciliated cells present on their surface (repurposing machinery whose normal function is to distribute mucus and flow pathogens and other material off the skin). As opposed to imposing tissue placement and shape from the top down (11), the design method presented here uses whole explants from developing frog embryos. While these explants, known as animal caps, have been used for decades to understand the early patterning events of epidermal and neural cell lineages (28-31), they have not been examined for behavioral capacity as proto-organisms, or used to create novel living machines with specific functions.

Here we report the use of *Xenopus* animal cells for generating swimming automata—capable of locomoting through a variety of environments. In addition to categorizing their lifecycle, behavior, and regenerative capacity, we also document the ability to introduce simple read-write functionality via RNA encoded photoconvertible proteins, serving as a proof of principle that experiences can be encoded as a molecular memory and retrieved at a later time. We use computational modeling to explain their multi-scale behaviors and effects on their environment. These findings demonstrate that novel behaviors can be elicited from biobots, and that they also inherit useful behaviors exhibited by many organisms, such as robustness to damage, and a spontaneous drive to exhibit collective behavior. This may, in future, make coaxing desired collective behaviors from biobot swarms more straightforward than programming equivalent behaviors into swarms of microrobots. Together, these results contribute to a new field at the intersection of synthetic biology and developmental biology and represent a new bottom-up method to produce simple biological machines.

Methods

We here survey the stages of the biological construction process (sects. m1-m8), computational design of simulated biobots to exhibit a representative collective behavior (sect. m9), and analysis of the distinct behaviors exhibited by a physical swarm of biobots performing this behavior (sect. m10).

m1: Animal Husbandry. All experiments were conducted using fertilized *Xenopus laevis* embryos as donor tissue. Wild type embryos were collected 30 minutes post fertilization and reared in 0.1× Marcs Modified Ringer solution (MMR), pH 7.8, at 14° C. prior to microinjection or animal cap dissection. Experimental procedures using animals for experimental purposes were approved by the Institutional Animal Care and Use Committee and Tufts University Department of Laboratory Animal Medicine under protocol number M2020-35.

m2: Explant culture. *Xenopus* animal cap explants were performed using standard methods (32). Briefly, fertilized embryos were raised at 14° C. in 0.1×MMR (pH 7.8), until Neiuwkoop and Faber stage 9. The vitelline membrane of each embryo was removed with surgical forceps (Dumont, 11241-30 #4) before being transferred to a 1% agarose lined petri dish containing 0.75×MMR for excision. Surgical forceps were then used to remove a circular mass of tissue from the animal-most region of each blastula embryo, after which the remainder of the embryo was removed from the dish. Each explant was then inverted and allowed to heal for 30 minutes to 1 hour in 0.75×MMR, allowing the tissue to ball up into a spherical mass. After healing, all the explants from each treatment were transferred to new 1% agarose covered dishes containing 10 ml 0.75×MMR and 5 ng/μl gentamicin and cultured at 14° C. until ready for use. Media was replaced three time a week to clean out cellular debris and any possible contamination.

For long term growth studies extending beyond the normal 10-day lifespan, explants were raised in *Xenopus* cell culture media containing 50% Ringer's solution, 49% Leibovitz L-15 Medium (ThermoFisher 11415064), and 1% fetal bovine serum. Explants were placed into individual wells of a 24-well plate lined with 2% agarose and were fed with 1 ml of culture media and 5 ng/μl gentamicin. Explants were moved to new wells with fresh media three times per week to reduce the likelihood of fungal contamination.

In experiments using the K+ inhibitor/Ca2+ activator barium chloride, Xenobots were exposed a 2.0 mM solution in 0.75×MMR beginning 3-4 hours after excision/healing and kept in the solutions throughout the remainder of the study. All pharmaceuticals were stored as stocks at 4° C. and working solutions were refreshed every three days.

m3: Microinjection. All mRNA was synthesized using standard message machine kits (Life Technologies) and stored at −80° C. until used. Prior to injection, cohorts of 4 cell stage embryos were transferred to a 3% Ficoll solution and aligned in a laser etched Petri dish. Individual embryos were then injected into each of the 4 cells using a pulled capillary to deliver approximately 500 ng of RNA in a 50 nL volume to each cell. Four cell embryos were chosen for injection over one cell due to the observation that expression tended to be more uniform at the 4-cell stage. Two hours after microinjection the embryos were washed twice in 0.1×MMR (pH 7.8), moved to new Petri dishes, and moved to a 22° C. incubator overnight. The following morning, the embryos were cleaned one final time before processing for animal cap excision. Constructs used in the current study included the multi-ciliated cell inhibitor Notch-ICD (33, 34) and EosFP (35).

m4: Immunohistochemistry. Multi-ciliated cell number was visualized through immunohistochemistry with the monoclonal anti-acetylated alpha tubulin antibody (Sigma T7451) using a protocol described previously (36). Cohorts of Xenobots from each treatment were pooled and transferred to a 3 ml scintillation vial containing MEMFA fixative (100 mM MOPS (pH 7.4), 2 mM EGTA, 1 mM MgSO4, 3.7% (v/v) formaldehyde). Fixation proceeded for 2H at room temperature on a nutator, after which the fixative was removed with a disposable pipette and the Xenobots were washed three times, ten minutes per wash, in phosphate buffered saline+0.1% Tween 20 (PBST) and stored at 4° C. until ready for processing. Processing began by blocking for 1H at room temperature with 10% goat serum in PBST. Samples were then rocked overnight at 4° C. in monoclonal anti-acetylated alpha tubulin antibody diluted 1:1000 in PBST+10% goat serum. Following primary incubation, samples were washed three times for 15 min in PBST before 60 min secondary incubation with AlexaFluor-555 conjugated secondary at 1:500 dilution in PBST. Following secondary incubation, samples were washed three times for 15 min in PBST.

m5: Behavioral analysis. Mazes used in behavioral tests were created from acrylic negatives and cast with 2% agarose. Each negative was affixed to the lid of a petri dish with a spot of cyanoacrylate-based adhesive and lowered into a dish containing sufficient volume of melted agarose to submerge the maze one half of its total height. Dishes cooled at room temperature for 1 hour before being wrapped in Parafilm and stored at 4° C. until use. For glass capillary experiments, standard 1.0 mm OD, 0.5 mm ID, 4-inch length capillaries (Sutter Instruments BF100-50-10) were cut down to a 2 cm length using a diamond knife. Individual Xenobots were then manually loaded into one end of the capillary and observed for 10 minutes on a stereoscope with an attached Sony IMX234 camera. In cases where movement was observed moving out of the loading area (i.e. the opposite direction of the preferred movement), the individual was rotated 180 degrees and reloaded in the same manner. Trials were considered a success if the individual emerged from the opposite end of the capillary.

For particle aggregation and displacement experiments, a stock solution carmine dye (Sigma-Aldrich C1022-5G) was created at a concentration of 0.01 g per 10 ml 0.75×MMR and vortexed for 10 seconds. Individual working solutions were then created in 1% agarose coated polystyrene petri dishes by diluting the stock 1:10, again in 0.75×MMR, for a final concentration of 0.001 g per 10 ml. Dishes containing the working solution were housed under an imaging microscope and allowed to settle for four hours at 22° C., creating a layer of particulate dye on the surface of the dish. Silicone coated iron oxide spheres (Ocean Nanotech SOR-10-50) were prepared in a similar manner, though only one hour of settling was necessary due to the higher density of the material.

m6: Wound healing. To assess wound healing, individual Xenobots aged 4 to 7 days post-explantation were moved to fresh 1% agarose coated petri dishes containing 0.75×MMR. Surgical forceps were used to create a mechanical laceration spanning approximately one half the diameter of the individual. Images were collected before injury, directly following injury, 5/10/15 minutes following injury, and after 48 h of healing. Images were first processed by cropping, downsampling, and binarization. To crop the images, contours were automatically drawn on the image by traversing the boundaries of each transition between body and background pixels to find closed loops (each of which is a contour). A bounding box was then drawn around the largest contour (by area), and the rest of the image is trimmed off. Finally, the cropped images were resized (downsampled) to a constant resolution (300×300). These processed images were then assessed by comparing each timepoint to its initial shape using Hausdorff distance. To calculate Hausdorff distance, the image was binarized, with each pixel assigned either 1 (for pixels belonging to the body of the organism) or 0 (the background). The Hausdorff distance is the largest discrepancy between pairs of pre- and post-damage body pixel coordinates, in terms of euclidean distance.

Formally, the Hausdorff distance for tissue type 1 is defined as:

$$H = \max\{\sup_{a \in A} \inf_{b \in B} d(a, b), \sup_{b \in B} \inf_{a \in A} d(a, b)\}, \quad \text{[Eqn. H.]}$$

where A and B are the sets of pre- and post-damage pixels, and d(a, b) is the Euclidean distance between pixels a and b. A small Hausdorff distance indicates that for every pixel prior to damage there is a pixel nearby post-damage, and vice versa. During repair, we measure the amount of shape change toward the pre-damage shape using the statistic $$\Delta = H_{post}/H_{injury}, \quad \text{[Eqn. Delta.]}$$

which is a ratio of two Hausdorff distances: one taken recovery (numerator) and the other immediately after injury (denominator).

Figure 2:
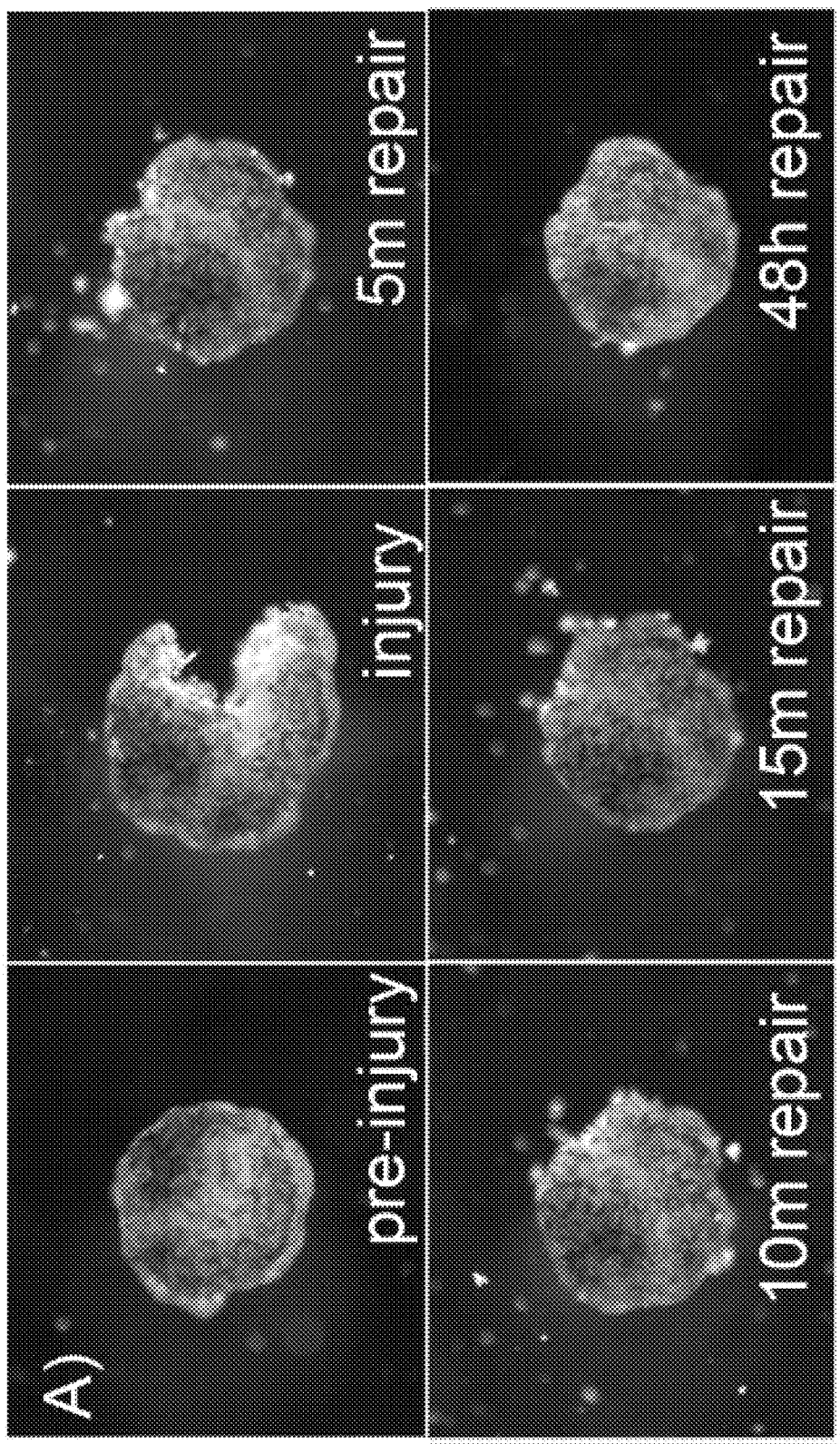
FIG. 2. Xenobots demonstrate robust repair in response to mechanical damage. (A) Individuals were given mechanical lacerations with surgical forceps and imaged before, immediately after, 5/10, 15 m proceeding injury, and after 48 h of healing. In all cases, individuals were capable of closing the wound and resolving the injury. (B) To quantify repair, images were first binarized using edge detection software. The resulting images were passed though Harsdorf distance software, comparing the pre-injury state with proceeding timepoints. (C) All repair time points showed significant improvement over that of the initial injury. Repeated measures ANOVA followed by Dunnett's post-hoc comparisons. Error bars indicate ±1 SD.
Figure 2:
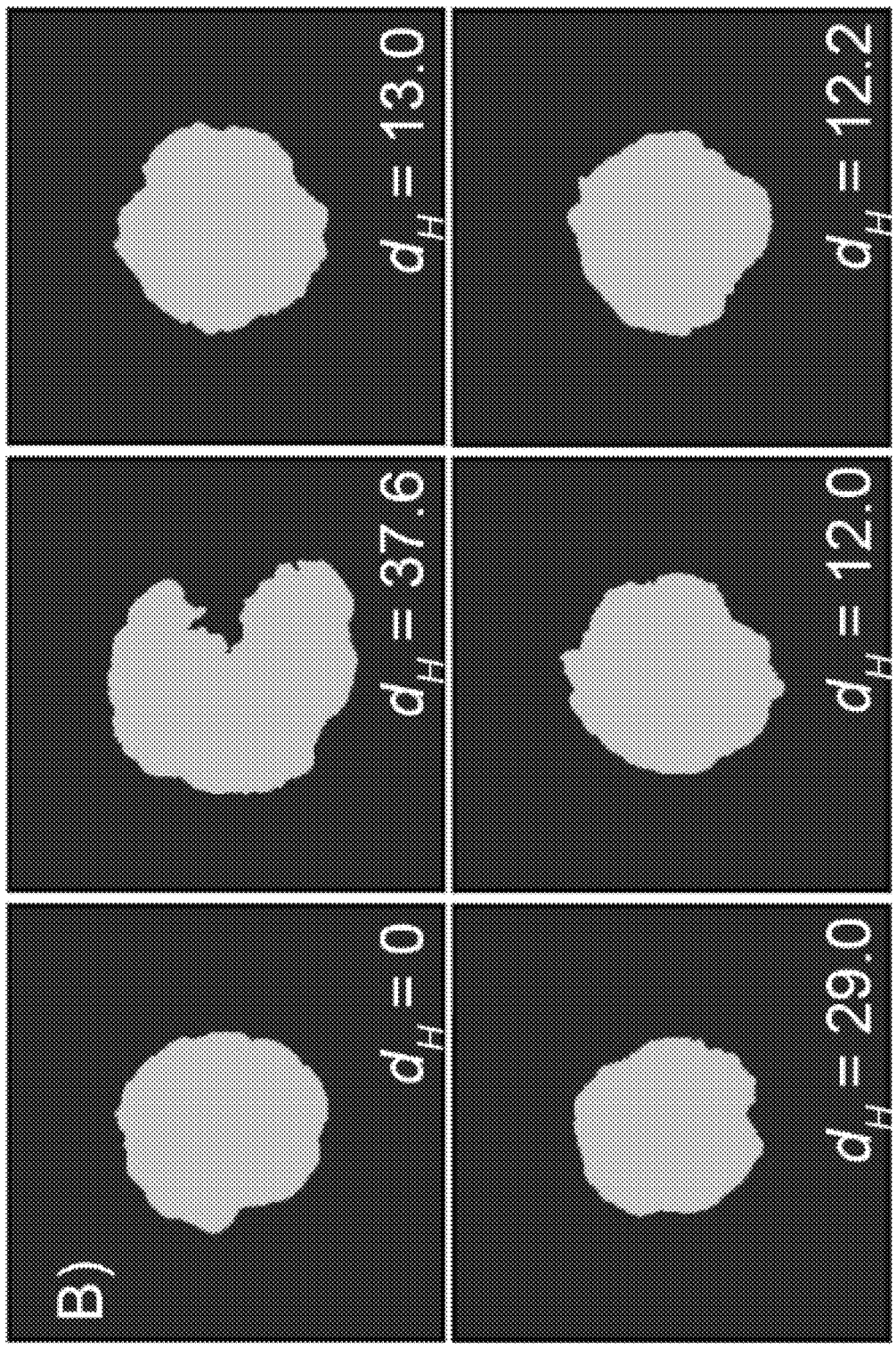
Figure 2:
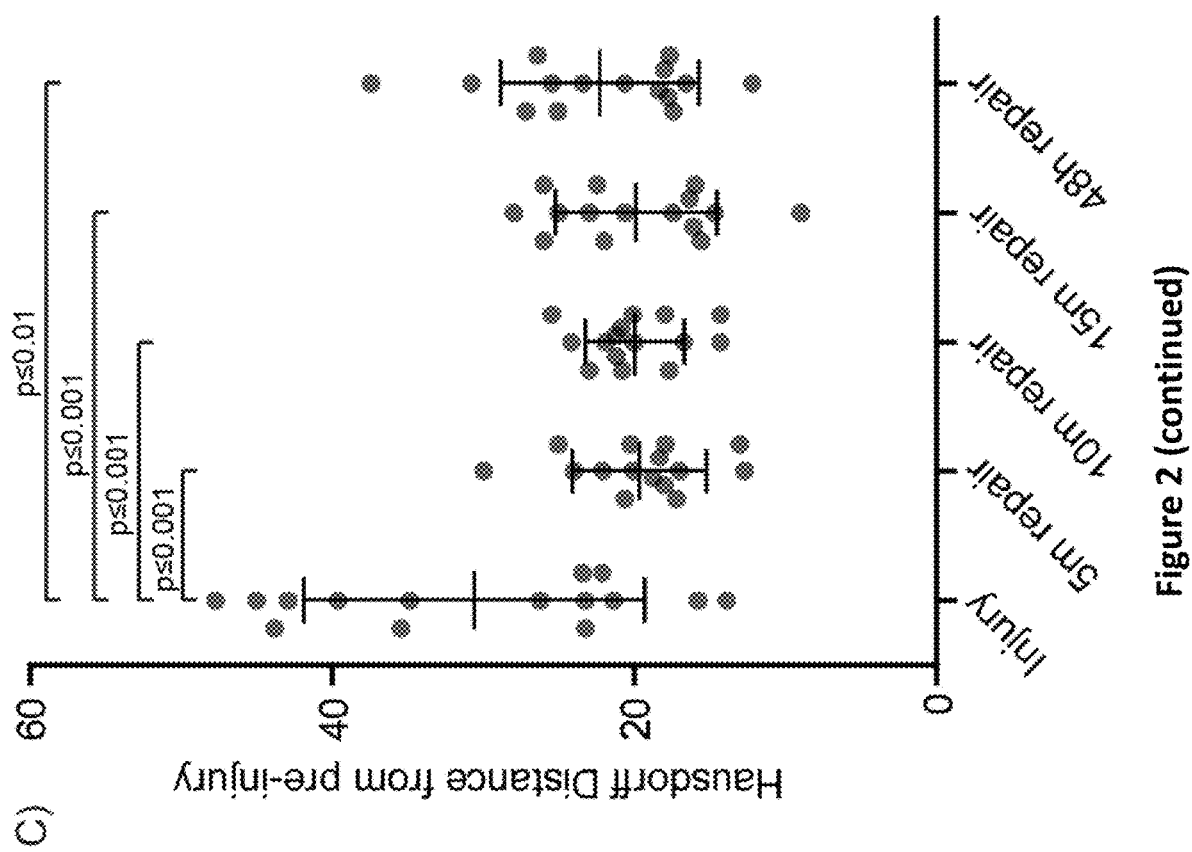

Because H is sensitive to rotation, H was calculated 360 times for every post-damage image, each time rotating the image by 1 degree. The rotation with the best match (the smallest H) was selected and plotted in FIG. 1. Because H is sensitive to the position of the body within the frame of an image, copies of images were auto-cropped (FIG. 2) such that the edge of the design fills the frame, and H was recalculated (with 360 rotations). Final Hausdorff distances conformed to normality and were compared using a repeated measures ANOVA, followed by Dunnett's post-hoc comparison of injury values to all proceeding timepoints.

m7: Imaging. Xenobot morphology was imaged using a Nikon SMZ-1500 microscope attached to a QImaging Retiga 2000R CCD camera. Live samples were photographed in 0.75×MMR at 22° C. using both overhead and substage illumination in combination with a concavity slide to keep the Xenobots in view. Immunofluorescence was detected using a 4× or 10× objective and standard TRITC filter cube on an Olympus BX-61 microscope equipped with a Photometrics CoolSNAP DYNO CCD camera and CoolLED pE-300 lightsource. Images were captured as tiff z-stacks and combined into composite images using Metamorph software before being moved to ImageJ for analysis.

m8: Motion tracking. Motion tracking of Xenobot behavior was completed by uploading time-lapse videos into Ethovision XT v.14/15 (Noldus Information Technology). A scaled background image was uploaded prior to data processing to accurately set movement speeds and distance. Tracking was completed in using automated settings and the coordinates of each xenobot position across the time lapse was then exported as an .xslv file via analysis tools. Any tracking errors were manually removed (field values left empty) in the .xslv file after the coordinates were exported from Ethovision for statistical analysis.

m9: Modeling collective behavior. All modeling was run in voxcraft-sim (37), a GPU-accelerated implementation of the Voxcad environment, which has been documented previously (38, 39). Xenobots are simulated by hundreds of elastic voxels (deformable cuboids), each approximating a section of tissue, rather than a one-to-one voxel-to-cell representation. At each time step, the dynamics (position and motion) of every voxel can be updated in parallel across multiple independent simulations. Xenobots here were simulated with Young's modulus of 0.02 MPa, density 1,500 kg/m^3, 0.35 Poisson's ratio, and coefficients of static and dynamic friction of 1 and 0.5, respectively. The simulated debris were slightly stiffer (0.03 MPa), less dense (1,000 kg/m^3), and had a higher coefficient of dynamic friction (0.8). The debris were made slightly adhesive to better approximate the real properties of the physical particulate matter: a persisting but breakable bond was formed between a pair of voxels if they touched and broken if the bond's stress exceeds a threshold (0.05 MPa).

The material properties of the voxels were manually adjusted for simulation speed (heavier/softer material can be stably simulated with a larger time step of numerical integration because their resonance frequency is lower than lighter/stiffer material). Each simulation consisted of 22,940 time steps (long enough to see pile-making behavior occur), with step size 0.00044 sec (low enough to ensure simulation stability; for details see (38)), yielding an evaluation period of ten seconds. The aggregate (metachronal wave) force produced by a patch of beating cilia was modeled on each surface voxel as an impulse force originating at the center of the voxel and pointing in any direction in the horizontal (x,y) plane. Internal voxels inside a Xenobot do not have cilia, nor do the debris. The maximal magnitude of the force was manually adjusted to ensure that the maximal speed would not cause continual tumbling behavior (which has not been observed in vivo).

A generative network (40) was used to genetically encode the cilia force of every surface voxel. The network takes as input the initial x, y, z position of a voxel (at simulation time t=0) and outputs an impulse force for that voxel. This force is then fixed for the remainder of the evaluation period. The network is inherently biased such that when it generates the constant force for each surface voxel in the simulated swarm, voxel pairs close together in space are more likely to have similar cilia forces than a pair of initially distant voxels. This biases search toward spatial regularity. For more details, see (41).

An evolutionary algorithm (42) was employed that maintains a population of 40 initially random genetic networks for 500 generations. At every generation, the population is doubled by making a randomly mutated copy of each of the 40 networks, where a mutation either adds, removes, or modifies one of the network's edges or vertices (for more details see (11)). Each network then generates cilia forces for a swarm of virtual Xenobots, and the swarm's behavior is evaluated for ten seconds in simulation. The fitness of a swarm (F) was measured as the number of debris voxel pairs within three voxel length units of each other (they are initialized on a grid, four voxel lengths away):

$$F = \sum_{i=1}^{1,225} \sum_{j=1}^{1,225} d(v_i, v_j) \quad \text{Eqn. MCB.}$$

where $v_i$ is the i-th debris voxel (within the 35×35=1,225 grid of debris), $$d(a, b) = 1 \text{ if } dist(a, b) < 3$$
$$d(a, b) = 0 \text{ otherwise,}$$

where dist(.) is the euclidean distance.

This objective function was intended to promote the evolution of pile-making behavior. We also investigated an alternative objective function that measured the pairwise sum of voxel distances; however, the penalty of moving debris apart resulted in no Xenobot movement.

Results

*Xenopus* embryonic ectoderm creates a motile living machine. Previous reports utilized a top down approach to impose shape, cell type, and contractile motion on a first generation of mobile living machines (11). In contrast, the current study used a bottom up approach to ask whether cells removed from their normal developmental constraints would be able to self-organize into a different type of living form. Production began by harvesting stem cell tissue from the animal hemisphere, a region of undifferentiated presumptive ectoderm, from Neiuwkoop and Faber stage 9 *Xenopus laevis* embryos (FIG. 1A). Tissue explants were then moved to a 0.75× Marc's Modified Ringer's (MMR) solution, pH 7.8 and allowed to heal for 1 h at 20° C. (FIG. 1B) and then cultured at 14° C. until experimentation begins (FIG. 1D). Under these conditions, explants form into spheres of tissue (FIG. 1C) that differentiate over the course of 4 days into ciliated epithelium. Three days after formation, explants become mobile in aqueous solutions and are capable of moving at rates exceeding 100 μm/s (FIG. 1E). Fully differentiated spheres range in size from an average of 487±39 μm for the smallest cut explants, to 602±30 μm for the largest (n=15 and 13 respectively).

Surprisingly, we observed motile behavior, as the cells' native cilia, which normally move material past the animal surface, were spontaneously re-purposed for coherent locomotion. Movement is driven by flow arising from multiciliated cells present on the surface of the construct (which are revealed by anti-acetylated tubulin immunohistochemistry (FIG. 1F)). Further, this motion can be abolished by inhibiting multiciliated cell formation through overexpression of the Notch receptor intracellular domain (NotchICD), which drives the differentiating tissue to other epidermal cell fates (FIG. 1F'). Multiciliated cells are also naturally present on the skin of the frog (FIG. 1G), and likewise respond to the overexpression of NotchICD (FIG. 1G'), though explants display a higher multi-ciliated cell density per area than age matched tadpoles (FIG. 1H).

Figure 6:
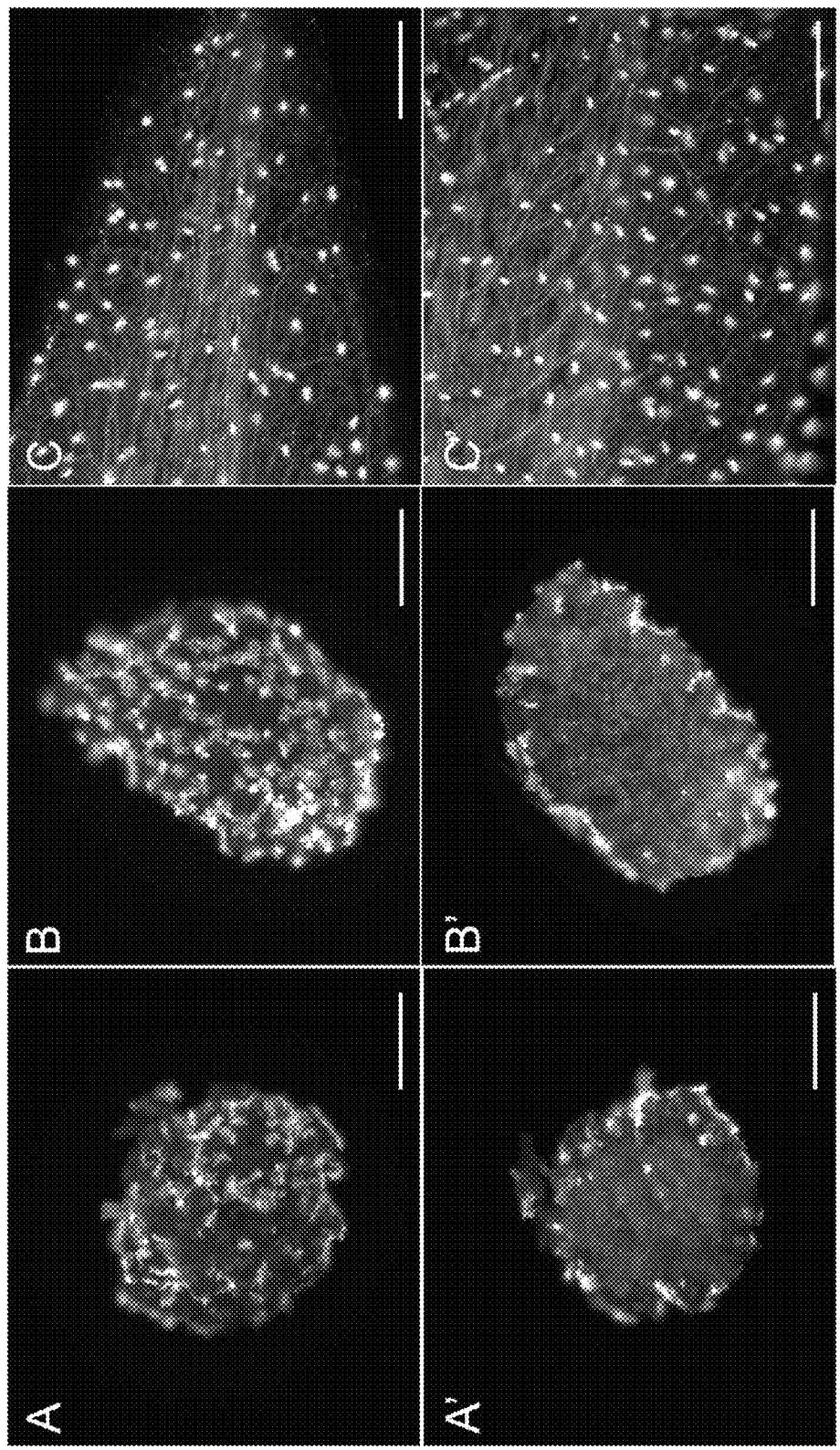
FIG. 6. Ectoderm derived Xenobots do not contain neural tissue. Small (A, A') and large (B, B') Xenobots were fixed, bisected, and processed with anti-acetylated tubulin immunohistochemistry. Visualization of the fluorescent secondary reveals the presence of multiciliated cells along the surface of the Xenobot, but no neurons were present externally or internally (n=24). Similarly, young tadpoles also possess multiciliated cells across the epidermis of their tail (C) and trunk (C'). However, in the case of tadpoles, motor axons are present between the somites and peripheral nerves are observed throughout the fin tissue. Scale bars indicate 250 μm.

The degree of behavioral complexity we observed is normally associated with a nervous system (43). Although made entirely of skin, we sought to confirm whether there might be any neurons in the Xenobots. Using a pan-neuronal marker in immunohistochemistry, we showed that no neurons were present at the surface or internally in any of the individuals imaged (FIG. 6, n=24), indicating that their behavior is driven entirely by the signaling and functional dynamics of non-neural cells. The Xenobots are thus a new synthetic model for understanding preneural life forms and their capacities (44, 45).

Figure 7:
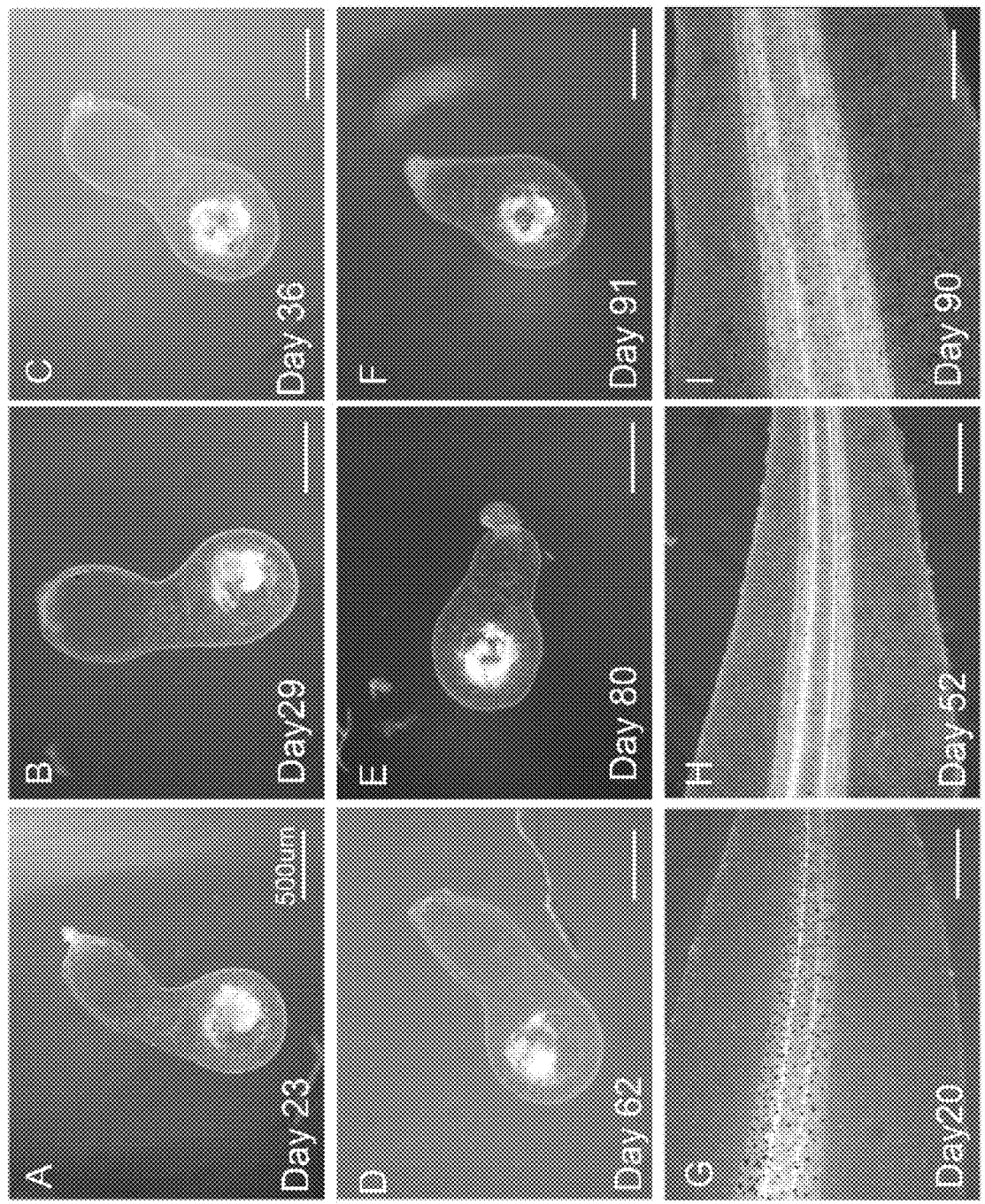
FIG. 7. Xenobot lifespan can be extended with nutrient rich media. Reared in standard 0.75×MMR, Xenobots live an average of 10 days post excision, metabolizing yolk platelets maternally loaded into the embryo. However, this lifespan can be extended for a period of months (A-F) with the addition of nutrient rich culture media. Under these conditions, Xenobots gradually lose pigmentation and become transparent, similar to the epidermis of a developing tadpole tailfin (G-I). Scale bars indicate 500 μm.

Explants have a lifespan of approximately 9-10 days after formation and do not require an external food source as they metabolize the maternally loaded yolk platelets present in all early embryonic *Xenopus* tissues. While their spontaneous disintegration is a welcome safety feature for deploying synthetic biobots, we sought methods to extend their working capacity by taking advantage of the cells' metabolic machinery. We found that their lifespan can be extended for timeframes exceeding 90 days if raised in a *Xenopus* specific culture media (FIG. 7). This ability to control their lifespan also availed us the opportunity to characterize their novel "developmental sequence", as their morphology is not like that of normal *Xenopus* embryos. We found that their pigmentation lightens with age (FIG. 1I-J'), although their average velocity does not vary significantly across explant lifespan (Kruskal-Wallis one-way ANOVA, p=0.29, FIG. 1K), and they eventually acquire a balloon-like, extended spheroid morphology (FIG. 7). At the end of their lifespan, explants begin shedding cells and deteriorate until the multiciliated cells no longer function and the tissue disintegrates. Together, these results demonstrate that embryonic explants from genomically-normal *Xenopus* cells form motile living machines with novel morphologies which are capable of aqueous locomotion via cilia.

Xenobots self-repair after damage. A desired feature in biological and artificial machines is a robust ability to deal with unexpected damage, arising from both normal wear and tear or external environmental insult. To examine the repair ability of Xenobots, 5 day old individuals were given severe mechanical lacerations with surgical forceps. Lacerations were performed with a single incision, opening a wound across approximately half of the diameter of the individual, and spanning the entire width. Images were collected prior to damage, directly proceeding damage, 5/10/15 m post damage, and 48 h following injury. In all cases individuals were capable of resolving the wound, closing the injury site and reestablishing a spherical shape (FIG. 2A). Repair appeared to occur quickly, with the majority of the laceration closing within the first five minutes of observation. Following insult, each Xenobot was reared individually for an additional 48 hours, to determine long term survival. In no cases was mortality observed, all individuals (n=15) persisted for the remainder of the experiment.

To quantify the degree to which the post-repair shape matched that of the individual preinjury, the geometry of an injured Xenobot was compared to its initial shape using Hausdorff distances—a calculation of the degree to which two metric spaces differ. Images were first binarized using edge detection software (FIG. 2B) and then run through a Hausdorff distance software, comparing pre-injury shapes to each of the subsequent images (FIG. 2C). Analysis revealed that all repair timepoints showed significant improvement compared to initial injury (repeated measures ANOVA, $p<0.0001$), with values remaining flat after the initial 5-minute time point. A slight, non-significant, increase can be noted after 48 h of repair, however, this is likely due to further aging and development (thus further changing Xenobot shape compared to the pre-injury time point) rather than a regression in repair. Together, these data demonstrate that Xenobots possess a robust ability to self-repair following injury, and that unlike *Xenopus* tadpoles which repair deformations back to a normal frog-like anatomy (46), they repair to their characteristic, novel Xenobot morphology, not to a frog embryo-specific shape.

Figure 3:
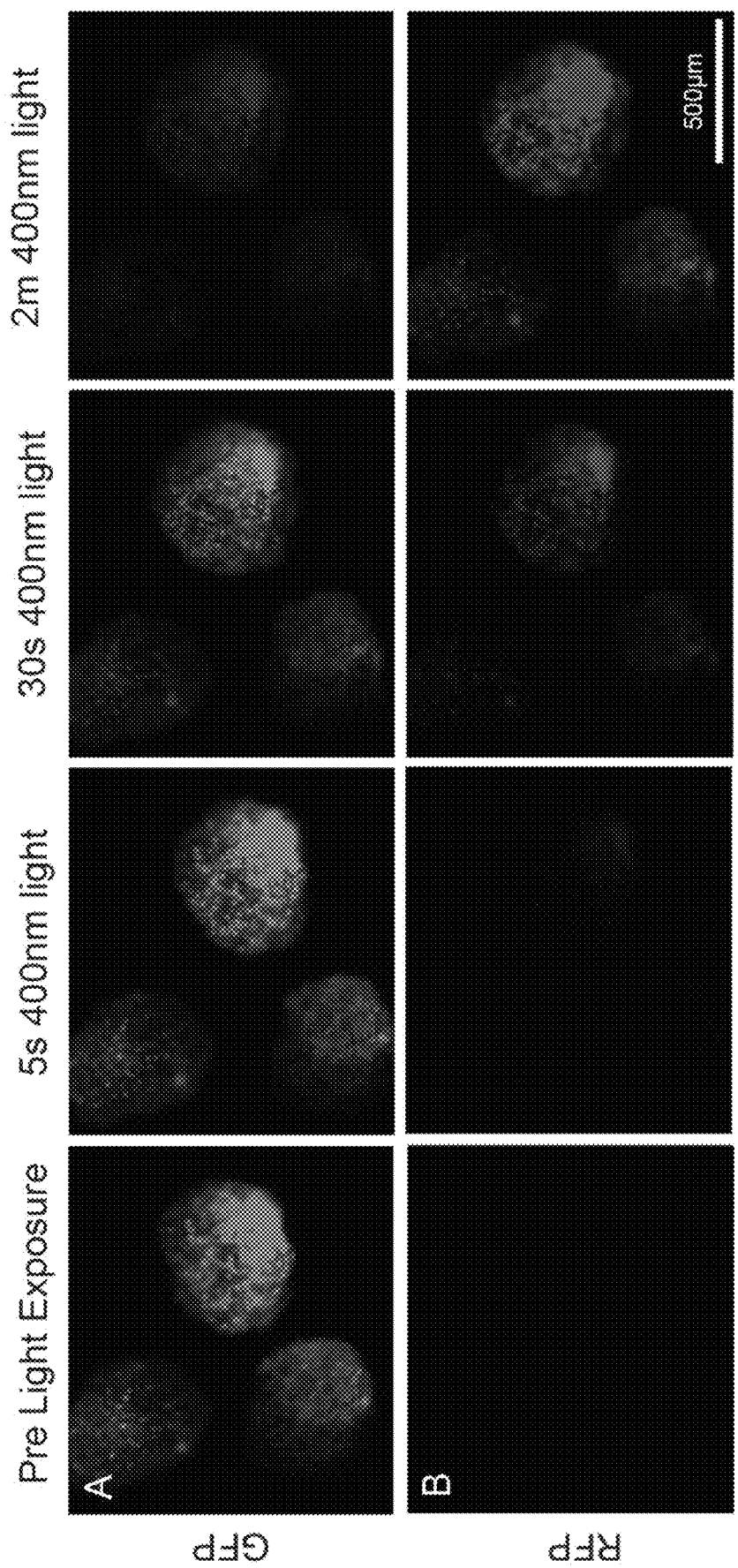
FIG. 3. Xenobots can record experience using a photo-convertible fluorescent reporter. (A) Xenobots injected with mRNA encoding the protein EosFP emit strong green fluorescence at five days of development. This signal permanently photo-converts to red when exposed to 390 nm light (B) due to an irreversible break in the backbone of the chromophore. (C) Using this reporter, Xenobots were introduced into a 5 cm arena containing an illuminated spot 7 mm in diameter. After exploring the environment for 1 hour, the individuals were collected and housed in a 14° C. incubator. (D,E) Two days later, fluorescent imaging revealed which Xenobots moved through the blue light during their exploration of the dish.
Figure 3:
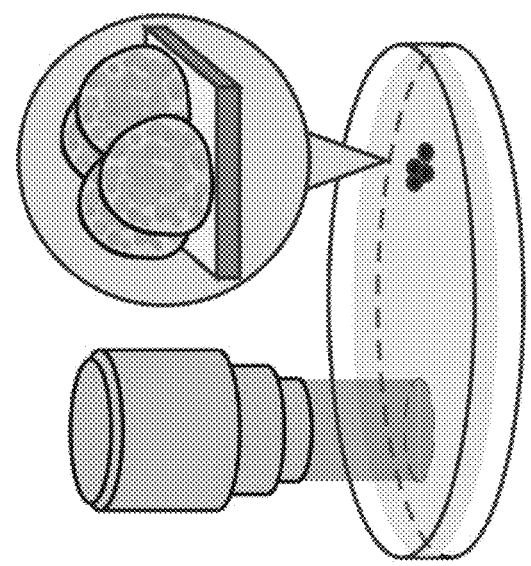
Figure 3:
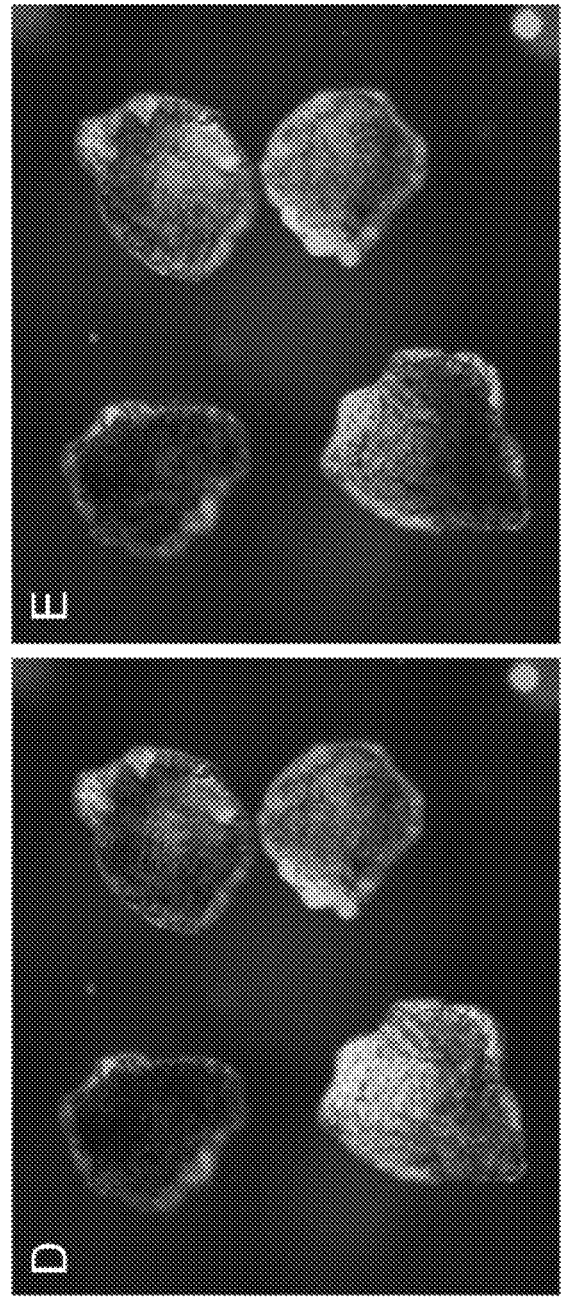

Fluorescent reporters enable a retrievable record of Xenobot experience. In addition to exploring an aqueous environment, a valuable capability of a living machine would be the ability to store and recall experiences across the organism's lifespan. To develop a proof of principle for a generalizable read/write function in Xenobots, mRNA encoding the fluorescent reporter EosFP (35) was injected into each of 4 cells of a stage three embryo, prior to tissue excision. When expressed, this reporter emits strong green fluorescence which is stable over the course of a Xenobot lifespan. However, when exposed to 390 nm blue light, the backbone of the chromophore undergoes a permanent conformational change, shifting the emission wavelength to red. This switch serves as a 'write' function of optical experience which can be 'read' later by an observer through fluorescent detection. After expressing this construct in Xenobots through mRNA microinjection, fluorescence was observed in the green channel but not the red channel prior to blue light exposure (FIG. 3A). Upon increasing duration exposure to 400 nm light, fluorescence in the green channel decreased while that in the red channel increased, with total photoconversion occurring within 2 minutes (FIG. 3B). This red signal remained stable over the lifespan remaining of the Xenobot, although green emission did reappear over time due to additional protein translation from the mRNA after the photoconversion period.

To demonstrate that this protein could be used as a record of experience in an unsupervised environment, 10 Xenobots expressing the construct were released into a 5 cm diameter arena (FIG. 3C). On the far side of the arena, 20 mm away from the loading zone, an illuminated 7 mm diameter spot of 400 nm 0.6 mw blue light was projected vertically through the dish. The Xenobots were then given two hours to explore their environment, after which the light source was removed and the Xenobots placed to a dark 14° C. incubator. Two days after exploring the environment, the Xenobots were imaged for fluorescence using FITC and TRITC cubes. Of the ten individuals imaged, seven showed a complete lack of fluorescence in the red channel, indicating they did not experience enough 400 nm light to photoconvert. Three individuals possessed strong emission at red wavelengths, revealing exposure to blue light during the 2-hour exploration period (FIG. 3D, E). Together, these data demonstrate that engineered read/write circuitry can be easily introduced and assayed in living Xenobots, allowing a subsequently retrievable record of their experience.

Figure 4:
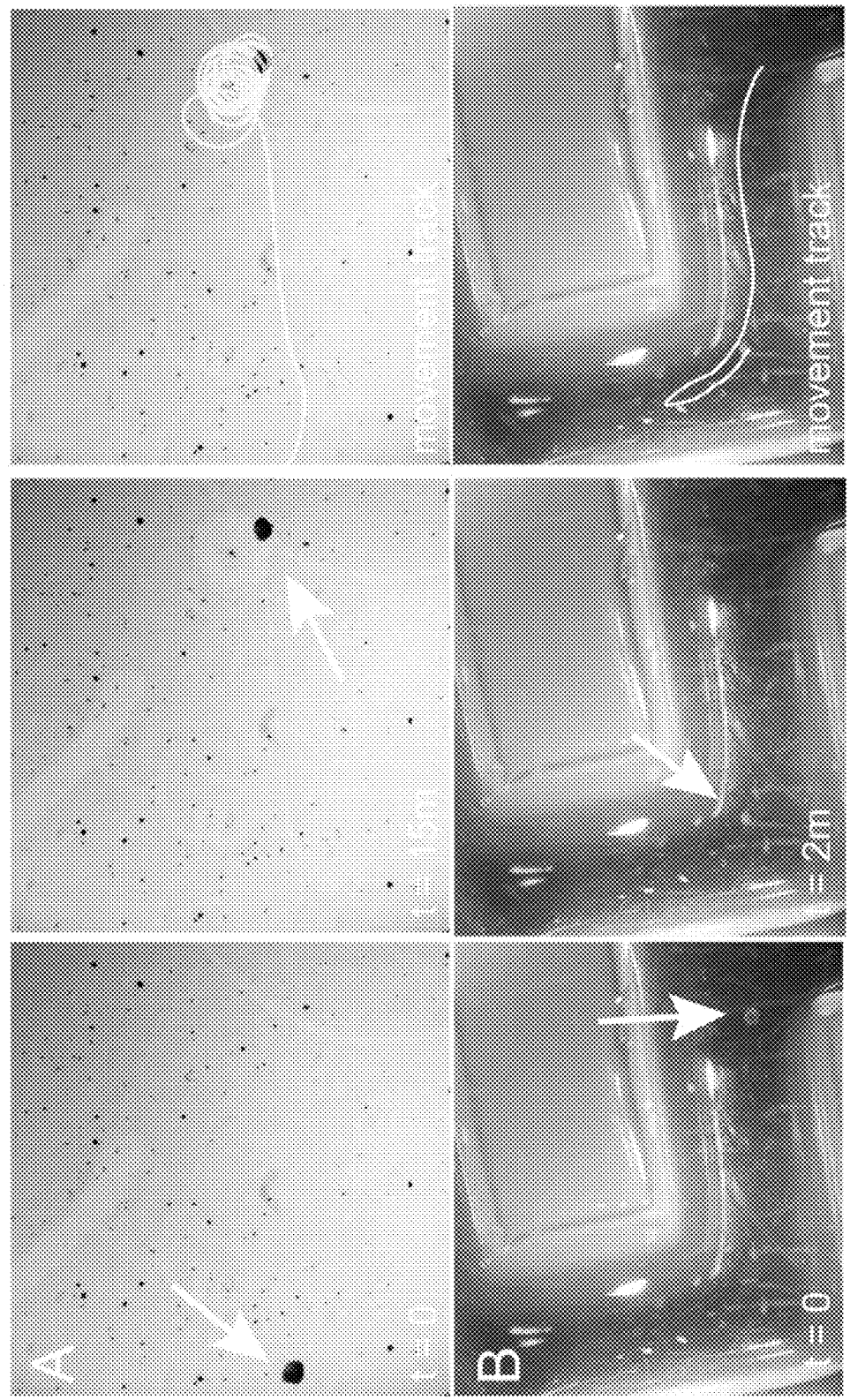
FIG. 4. Xenobots navigate diverse environments. (A) Xenobots were released into an open field with debris composed of carmine dye particles. Similar to prior observations, individuals demonstrate a variety of movement types, from linear motion to elliptical tracks. (B) In large mazes, individuals follow channels provided by the environment. (C) Narrow mazes begin to restrict rotational movement, resulting in individuals following edges in the arena. (D) In a narrow glass capillary with a 0.58 mm inner diameter, individuals can traverse the length of the tunnel and emerge from the opposite end.
Figure 4:
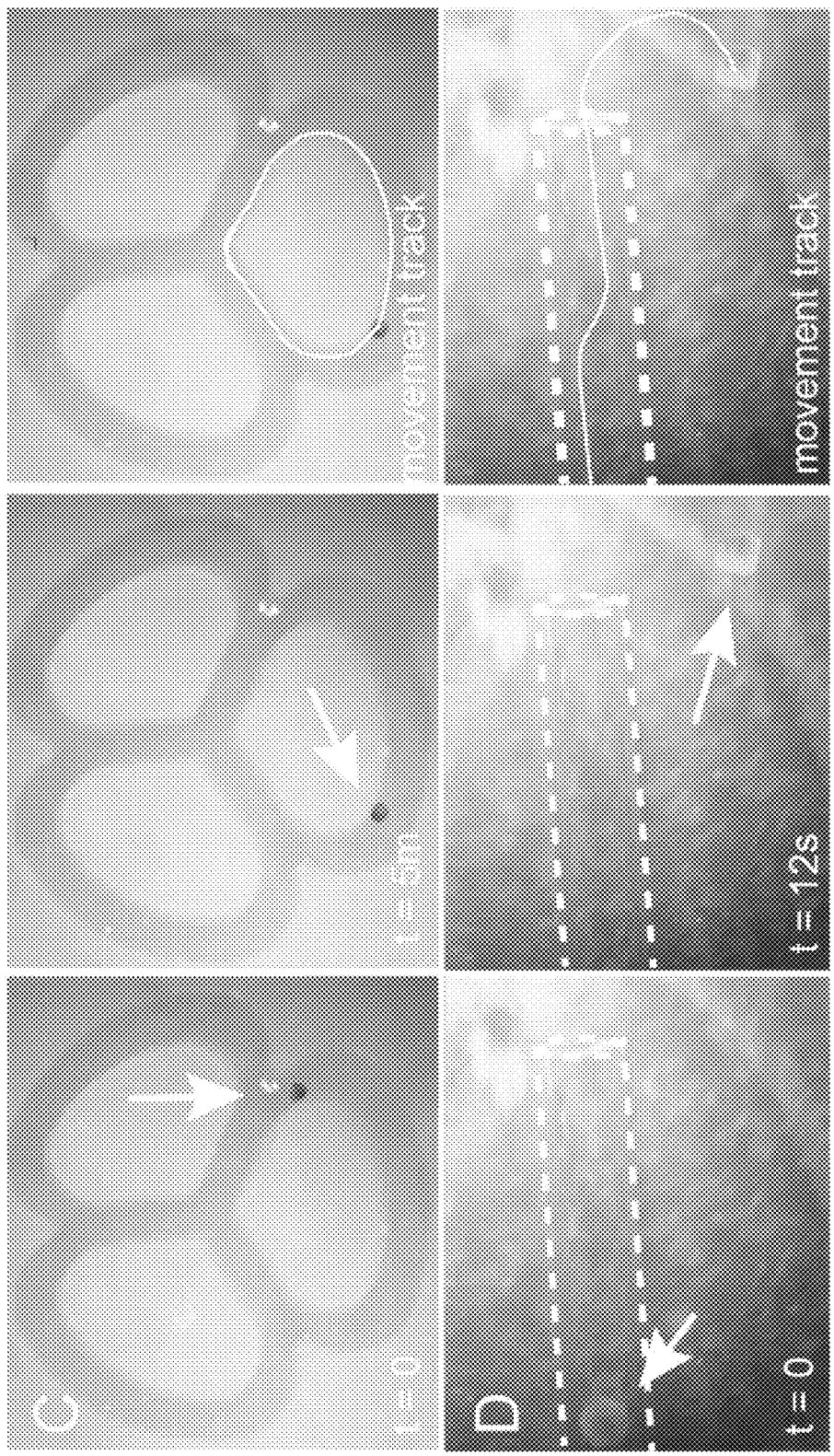

Xenobots can move through varied environments. To test the ability of individual Xenobots to navigate varied environments, arenas of decreasing dimension were constructed ranging from completely open fields to restricted capillaries with a 580 nm inner diameter. In all cases, the Xenobots were capable of locomoting through the space although some individuals became challenged in narrow passages. In an open arena containing a debris field of various sized carmine particles, movement was similar to the results presented above and individuals showed varied combinations of linear and circling movement types (FIG. 4A). Reducing the size of the arena to a 1 cm width maze, Xenobots moved along the center of the channel and were observed occasionally reversing directions during the observation period (FIG. 4B). While the tendency to stay in the center of the channel is likely due to the rounded nature of the floor of the maze, it is unclear what caused reversals in direction as they did not occur repeatedly at the same location nor within the same individual. A further reduction of maze width to 2 mm resulted in frequent circling of one wall of the maze (FIG. 4C). Given the observation that most Xenobots tend to exhibit elliptical movement patterns, it is likely this behavior arises from the walls inhibiting completion of an elliptical path which in turn drives the resultant directional movement.

Finally, individuals were placed at one end of a 2 cm capillary tube with a 580 nm inner diameter (FIG. 4D). Surprisingly, 42% of Xenobots tested (n=12) were able to traverse the capillary end to end, and this number included some individuals which did not show movement in the open field test. In addition, all individuals demonstrating movement successfully traversed the entire length of capillary—none became lodged or reversed directions at intermediate locations between the two ends. Together, these data reveal that Xenobots can successfully traverse varied environments without having been specifically shaped or constructed to fit a given scenario, a desirable feature in many soft bodied robotic applications.

Figure 5:
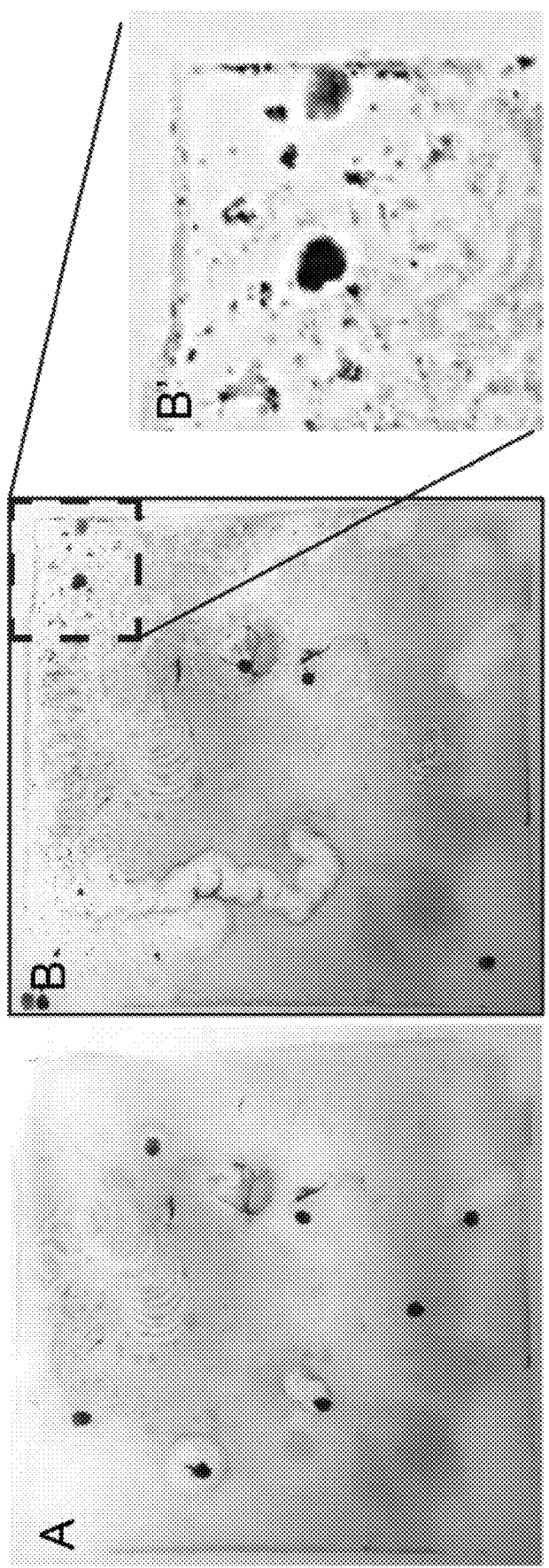
FIG. 5. Modeling collective behavior. (A) Six living Xenobots were released into an arena covered in 5-10 μM silicone coated iron oxide beads. (B) After 12 h, the living Xenobots cleared regions of the arena, creating piles of particles across the environment (B'). (C) Five simulated Xenobots (green) were initially placed within a 35×35 grid of particulate matter (red) and collectively evolved in silico as a swarm to recapitulate a specific behavior observed in vivo: pile making ((C') Expanded inset). (D) The Xenobots were identically shaped and propelled with open-loop control (no sensors were included) according to an initially random set of static cilia forces. (E) The simulated Xenobots were "blind" but nevertheless, after 500 generations of evolution in silico, the simulated swarm exhibited dynamic coupling, complex movement trajectories, and herding behavior by pushing the initially separated debris into central piles. (F) The body shape of five simulated Xenobots (F'; green) was evolved in silico to aggregate particulate matter. Each individual Xenobot in the swarm shares the same evolved morphology but has its own evolved cilia controller. The living Xenobots in this paper have spherical bodies, but can be sculpted to match the computer-designed blueprint (F'''). (G) It remains to be determined if the behavior of a swarm of computer-designed Xenobots would match the predicted behavior.
Figure 5:
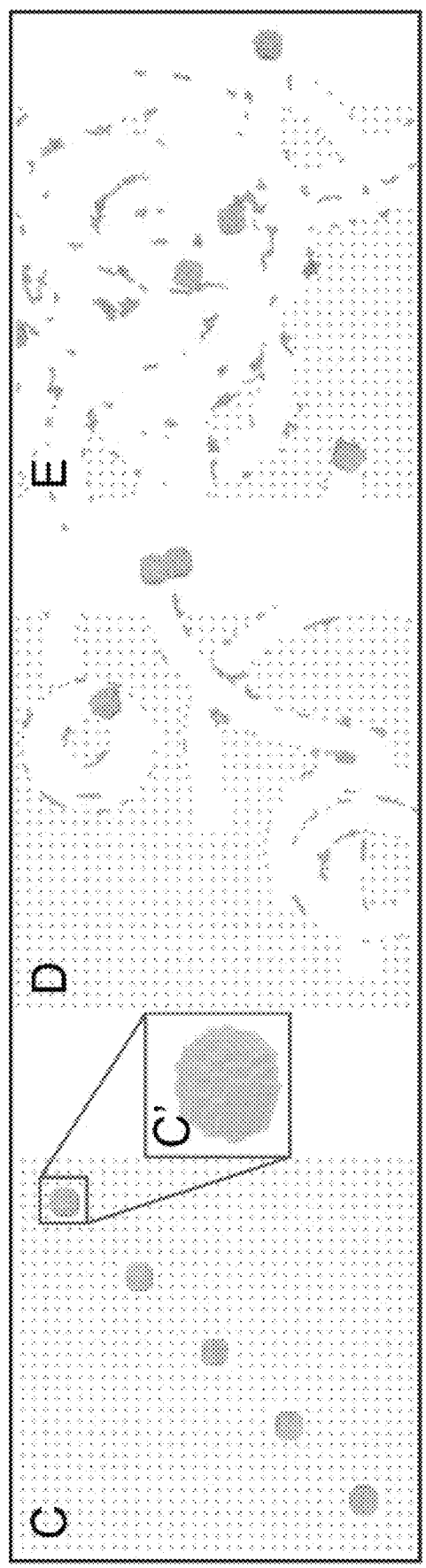
Figure 5:
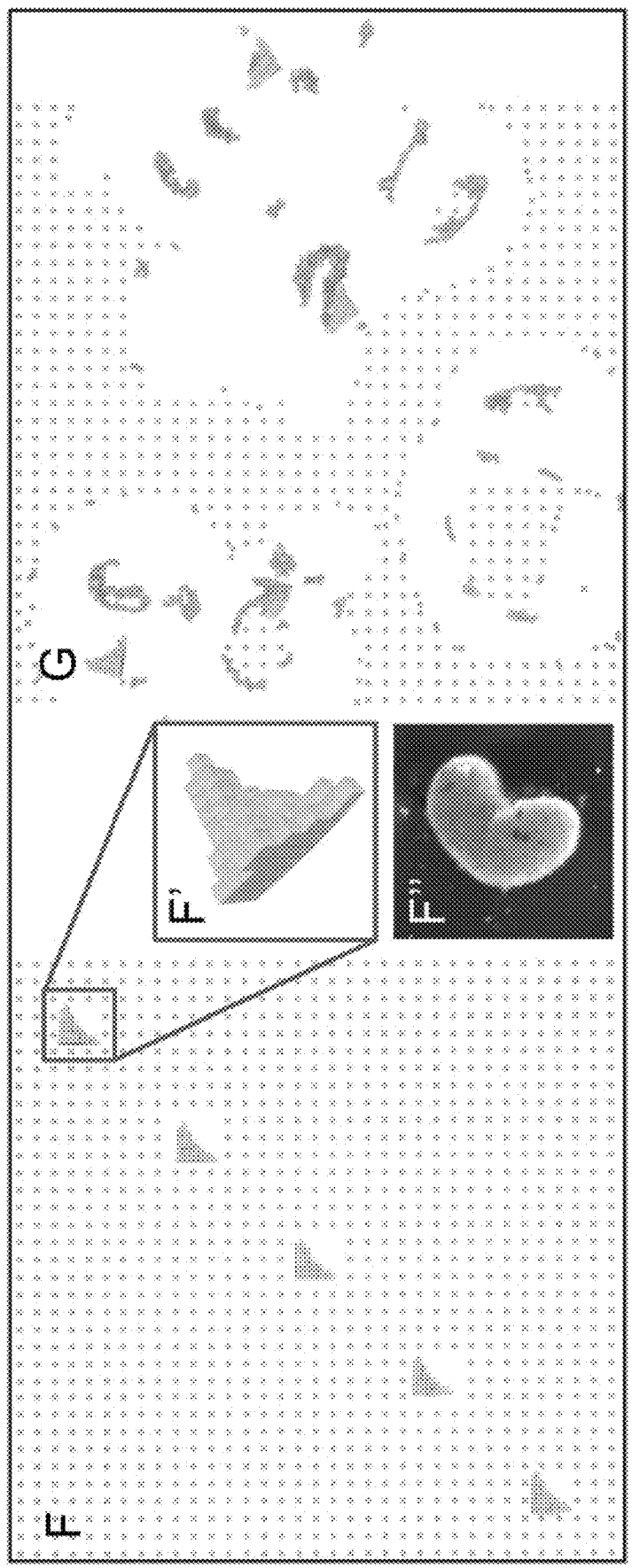

Modeling emergent collective behavior: particle aggregation. Beyond individual movement, cohorts of Xenobots demonstrate emergent group behaviors, such as the spontaneous aggregation of particles resulting from their joint movement patterns (11). Here we have further characterized this behavior by releasing multiple Xenobots into arenas covered with 5 µM silicone coated iron oxide spheres and filming time-lapse video of subsequent movements. Over the course of 12 hours, regions of the arena were swept clean of the particles, creating piles of debris across the field (FIG. 5A, B). The size and density of the particles here are significantly larger than that used in prior work, extending the potential uses of the Xenobots.

We hypothesized that the remarkable effect of their combined behaviors upon the environment could be achieved as an emergent property, not requiring feedback and active sensing/control by the bots. In order to investigate this possibility, we employed a physics-based simulator in combination with an evolutionary algorithm to reproduce the behavior in silico using sensorless designs. While previous work (11) used similar AI models to predict movement in cardiac driven "walking" Xenobots, accurately predicting cilia-driven movement of an individual physical Xenobot presented several novel challenges. For example, the behavior of the swimming Xenobots are not obviously determined by their geometry: similar spherical bodies can move very differently. Even a single swimming Xenobots can exhibit a complex behavioral repertoire driven by tumbling behavior along their axes, rather than traveling along a single trajectory.

To overcome these barriers, we developed a GPU-accelerated physics engine (37) and used it to evolve pile-making swarm behavior for the first time in simulated Xenobots. This involved hundreds of thousands of simulations of swarm behavior, whereas in previous work only a single simulation of Xenobot swarm behavior was reported (11). Five spherical Xenobot disks (each with a diameter of nine voxels and a height of seven voxels) were placed amid a 35-by-35 grid of loose voxel debris (FIG. 5C). The simulated Xenobots' initially spherical bodies were shaved down by two ventral voxel layers (FIG. 5C') to increase the surface area in contact with the simulated ground plane. This stabilizes their movement and reduces the likelihood of persistent tumbling behavior in silico (a behavior that is not common in physical Xenobots).

Five independent evolutionary trials were then conducted. Each trial started with its own unique set of 40 random genetic networks, yielding five champion swarms: the design that achieved the highest value of Eqn. MCB above, in each evolutionary trial. In addition, no movement from the swarm results in a fitness of zero. After behaving for 10 seconds, swarms generated by the random networks (FIG. 5D) have the mean fitness 1098.63+/−811.19 (standard deviation). After 500 generations of evolutionary improvement (<48 hours wall clock time), the five champion swarms (FIG. 5E) have mean fitness 4278.2+/−76.69, which is significantly better pile-making (t-value=−8.71966; p-value <0.00001) according to the imposed objective function. This suggests that evolution did occur in silico. It also supports the hypothesis that "hardcoded" behavioral trajectories of individual biobots, when combined together with debris under physical forces, can generate piles without sensory feedback.

Particle gathering behavior could enable a number of useful environmental applications for Xenobots in the future, especially if the size and distribution of the piles could be specified by the investigator. As proof of principle for this application, we performed a second set of experiments to assess if shape could affect pile making. The experimental design is the same, except each swarm has a second genotype network (in addition to cilia forces) that determines the shape of each Xenobots. Across ten new evolutionary trials, swarms generated from the initial set of randomly-generated network pairs have the mean fitness 687.58+/−826.88 (standard deviation). After 500 generations of evolutionary improvement, the five most fit swarms (one from each trial) (FIG. 5F, G) have mean fitness 12671.9+/−3930.18, which suggests evolution did occur (t-value=−36.37944; p-value <0.00001). Additionally, the data suggest that the mean fitness achieved with morphological change is higher than without morphological change (t-value=−4.4454; p-value<0.00033).

It was found that all evolved swarms could be physically constructed in the real world: Xenobots morphology can be sculpted from an initially spherical body (FIG. 5F', F'') using microsurgery tools. In a single swimming Xenobots, the successful transfer of behavior from in silico to in vivo remains an open problem. Although it is challenging to predict cilia-driven movement of an individual physical Xenobots, the degree to which a swarm tends to herd particles may be sufficiently determined by their shape, providing useful avenues for downstream applications in the real world.

Discussion

Here we documented the creation of Xenobots, synthetic living machines derived from amphibian embryonic explants, their ability to spontaneously exhibit collective behavior, and the potential to design such swarms in future to exaggerate these behaviors. Compared to our previously reported design method (which produced contractile driven motion through top-down implementation of shape and tissue placement (11)) the Xenobots reported here exhibit bottom up emergent behaviors and generate movement through multiciliated cell propulsion. These swimming Xenobots survive for up to ten days in mild saline solution without additional energy sources, and for multiple months if supplemented with cell culture medium. Movement first appears four days after construction and average velocity remains constant across the lifespan of the Xenobot cohorts. Further, motion can be inhibited through the overexpression of the intracellular domain of notch, which inhibits multiciliated cell development by driving precursors to other epidermal lineages. Together, this design method allows for the rapid generation of many mobile constructs with minimum top down design from the investigator.

Xenobot speed and behavior remains constant across their ten-day lifespan, pointing to their potential for maintaining desired swarm behavior. Movement tends towards circular rotation, although arcing and linear motion was also observed less frequently. An interesting future area of study would include the enhancement of planar cell polarity patterning, enforcing specific tissue-scale cilia alignment to drive user specified motion types. Further, given their ability to self-locomote, Xenobots can move through a variety of diverse environments from open fields to narrow capillaries. These features suggest several possible downstream applications which are difficult for traditional robots, from the cleaning microfluidic chambers to environmental sensing and ecologically benign remediation in natural waterways.

The ability to program rudimentary sensing and memory into biobots was also demonstrated. As Xenobots can explore an aqueous environment, we designed a proof of principle system where an individual can record exposure to an environmental stimulus that can be read at a later time by an observer, using the photoconvertible reporter EosFP. After expressing the protein in Xenobots through mRNA microinjection, individuals emit strong fluorescence in green wavelengths. However, following exposure to 400 nm blue light, the reporter undergoes a permanent conformational change, shifting emission wavelengths from green to red. Using this feature, we were able to show that unsupervised Xenobots could explore an environment containing an illuminated blue spot, and exposure to this light could subsequently be assessed using fluorescent microscopy. The general methodology of the approach could be readily adapted to a wide variety of scenarios including: increased/decreased sensitivity to stimuli, chemical/contaminant detection, bioaccumulation of target substances, release of compounds upon sensation of stimuli, multimodal recording, and nested if/then circuitry.

Unlike current robots, in which robustness must be programmed in, Xenobots exhibit automatic self-repair following injury. When presented with lacerations, all individuals were able to heal the wound within 15 minutes and in no cases did an individual perish as a result of the insult. Tadpoles also rapidly resolve injuries resulting from mechanical damage or transplantation, revealing that like ciliary motion, emergent capabilities of cell groups can be deployed in different ways on very different body architectures. Further, contraction at the wound site is sufficient to close minor injuries but the mechanism behind large scale damage repair is unknown. The ability to self-repair remains an important feature of soft-bodied robots that is difficult to achieve using synthetic materials (47) but emerges naturally from the biology of our constructs.

While current Xenobots do not contain specialized sense organs, they display many behaviors comparable to those observed in highly sensorized robots, including the aggregation of environmental debris. We found that Xenobots can move through and push small amounts of debris, clearing regions of the arena while depositing piles of material elsewhere. To test if this behavior could result purely from the physics of sensorless locomoting bodies, we developed a new GPU-based physics engine that could handle the computational demands of many interacting soft bodies at high mechanical resolution. Our simulation results demonstrate that it is indeed possible to achieve the complex pile-making behavior seen in the physical Xenobots without any feedback from sensors. These modeling studies also provide a framework for predicting the collective behavior of a swarm of cilia-driven physical Xenobots based on their geometry, despite the difficulty of predicting cilia-driven movement of an individual physical Xenobot. Such studies also suggest that machine learning methods may in future automatically design the shape and tissue distribution of simulated biobots to maximize desired collective behavior in silico, which retain that collective function when physical copies of the best designs are constructed and deployed. This seems achievable, as transference was obtained with Xenobots previously, for desired individual behavior (11).

Finally, biobots differ from both robot swarms and modular robots in that they exhibit collective behavior and modularity at least four scales. There is the biobot swarm itself, but each individual biobot is composed of thousands of cells, each of which is itself a complex and semiautonomous machine. Finally, the intricate internal architecture of a cell houses myriad self-motile machines that build and maintain cellular integrity and function. Such multiscale structure poses unique future challenges and opportunities for altering collective function at each and all of these scales.

Together, these in vitro and in silico results provide a pipeline to move between the physical and virtual world, where results in one environment can inform the other. For example, modeling may allow rapid testing of many parameters that would be impossible biologically due to the time and effort involved. Alternatively, biological experiments can provide baselines and constraints to existing models, refining them with values which are translatable to real world scenarios for a range of downstream applications.

The computational modeling of unexpected, emergent properties at multiple scales, and the apparent plasticity of cells with wild-type genomes to cooperate toward the construction of new, functional body architectures, offer a very powerful synergy. Future work to better predict and control of the structure and function of synthetic living machines is likely to broadly impact several fields. Basic evolutionary developmental biology and basal cognition can use this new model to understand self-assembly of body forms and functional controllers. Moreover, existing toolkits of synthetic biology, bioelectrical signaling, and computation via cell networks offer an extremely rich space of possible living machines with useful functions including biomedicine, environmental remediation, and exploration (48-52).

REFERENCES FOR EXAMPLE 1

1. J. Yu, B. Wang, X. Du, Q. Wang, L. Zhang, Ultra-extensible ribbon-like magnetic microswarm. *Nat Commun* 9, 3260 (2018).
2. A. Servant, F. Qiu, M. Mazza, K. Kostarelos, B. J. Nelson, Controlled in vivo swimming of a swarm of bacteria-like microrobotic flagella. *Adv Mater* 27, 2981-2988 (2015).
3. H. Xie et al., Reconfigurable magnetic microrobot swarm: Multimode transformation, locomotion, and manipulation. *Sci. Robot* 4, (2019).
4. G. Adam et al., Towards functional mobile microrobotic systems. *Robotics* 8, 69 (2019).
5. M. Soreni-Harari, R. St Pierre, C. McCue, K. Moreno, S. Bergbreiter, Multimaterial 3D Printing for Microrobotic Mechanisms. *Soft Robot* 7, 59-67 (2020).
6. C. C. J. Alcantara et al., 3D Fabrication of Fully Iron Magnetic Microrobots. *Small* 15, e1805006 (2019).
7. E. Avci, M. Grammatikopoulou, G. Z. Yang, Laser printing and 3D optical control of untethered microrobots. *Advanced Optical Materials* 5, 1700031 (2017).
8. Q. Wang et al., Real-time Magnetic Navigation of a Rotating Colloidal MicroswarmUnder Ultrasound Guidance. *IEEE transactions on bio-medical engineering*, (2020).
9. I. R. Bruss, S. C. Glotzer, Curvature-induced microswarming. *Soft matter* 13, 5117-5121 (2017).
10. X. Dong, M. Sitti, Controlling two-dimensional collective formation and cooperative behavior of magnetic microrobot swarms. *The International Journal of Robotics Research* 39, 617-638 (2020).
11. S. Kriegman, D. Blackiston, M. Levin, J. Bongard, A scalable pipeline for designing reconfigurable organisms. *Proc Natl Acad Sci USA* 117, 1853-1859 (2020).
12. C. Anderson, C. D. Stern, Organizers in Development. *Current topics in developmental biology* 117, 435-454 (2016).
13. A. Bongso, M. Richards, History and perspective of stem cell research. *Best practice & research. Clinical obstetrics & gynaecology* 18, 827-842 (2004).
14. C. B. Kimmel, R. M. Warga, T. F. Schilling, Origin and organization of the zebrafish fate map. *Development* 108, 581-594 (1990).
15. L. Dale, J. M. Slack, Fate map for the 32-cell stage of *Xenopus laevis*. *Development* 99, 527-551 (1987).
16. Y. Hatada, C. D. Stern, A fate map of the epiblast of the early chick embryo. *Development* 120, 2879-2889 (1994).
17. A. Redkar, M. Montgomery, J. Litvin, Fate map of early avian cardiac progenitor cells. *Development* 128, 2269-2279 (2001).
18. R. Falk, N. Orevi, B. Menzl, A fate map of larval organs of *Drosophila* and preblastoderm determination. *Nature: New biology* 246, 19-20 (1973).
19. R. Woodrick, P. R. Martin, I. Birman, F. B. Pickett, The *Arabidopsis* embryonic shoot fate map. *Development* 127, 813-820 (2000).
20. G. Rossi, A. Manfrin, M. P. Lutolf, Progress and potential in organoid research. *Nat Rev Genet* 19, 671-687 (2018).
21. B. Zhang, A. Korolj, B. F. L. Lai, M. Radisic, Advances in organ-on-a-chip engineering. *Nature Reviews Materials* 3, 257-278 (2018).
22. J. H. Sung et al., Recent Advances in Body-on-a-Chip Systems. *Analytical chemistry* 91, 330-351 (2019).
23. J. Mustard, M. Levin, Bioelectrical Mechanisms for Programming Growth and Form: Taming Physiological Networks for Soft Body Robotics. *Soft Robotics* 1, 169-191 (2014).
24. S. J. Park et al., Phototactic guidance of a tissue-engineered soft-robotic ray. *Science* 353, 158-162 (2016).
25. C. Cvetkovic et al., Three-dimensionally printed biological machines powered by skeletal muscle. *Proc Natl Acad Sci USA* 111, 10125-10130 (2014).

26. B. J. Williams, S. V. Anand, J. Rajagopalan, M. T. Saif, A self-propelled biohybrid swimmer at low Reynolds number. *Nat Commun* 5, 3081 (2014).
27. V. A. Webster et al., in *Conference on Biomimetic and Biohybrid Systems* (Springer, Cham, 2017), pp. 475-486.
28. B. C. Gallagher, A. M. Hainski, S. A. Moody, Autonomous differentiation of dorsal axial structures from an animal cap cleavage stage blastomere in *Xenopus*. *Development* 112, 1103-1114 (1991).
29. J. Green, The animal cap assay. *Methods in molecular biology* 127, 1-13 (1999).
30. S. Sokol, D. A. Melton, Pre-existent pattern in *Xenopus* animal pole cells revealed by induction with activin. *Nature* 351, 409-411 (1991).
31. H. L. Sive, R. M. Grainger, R. M. Harland, Animal Cap Isolation from *Xenopus laevis*. *CSH Protoc* 2007, pdb prot4744 (2007).
32. T. Ariizumi et al., Isolation and differentiation of *Xenopus* animal cap cells. *Current protocols in stem cell biology* Chapter 1, Unit 1D 5 (2009).
33. D. A. Wettstein, D. L. Turner, C. Kintner, The *Xenopus* homolog of *Drosophila* Suppressor of Hairless mediates Notch signaling during primary neurogenesis. *Development* 124, 693-702 (1997).
34. J. L. Stubbs, L. Davidson, R. Keller, C. Kintner, Radial intercalation of ciliated cells during *Xenopus* skin development. *Development* 133, 2507-2515 (2006).
35. J. Wiedenmann et al., EosFP, a fluorescent marker protein with UV-inducible green-tored fluorescence conversion. *Proc Natl Acad Sci USA* 101, 15905-15910 (2004).
36. D. Blackiston, L. N. Vandenberg, M. Levin, High-Throughput *Xenopus laevis* Immunohistochemistry Using Agarose Sections. *Cold Spring Harb Protoc* 2010, pdb prot5532 (2010).
37. S. Liu, D. Matthews, S. Kriegman, J. Bongard, Voxcraft-sim, a GPU-accelerated voxelbased physics engine. 10.5281/zenodo.3835152, https://github.com/voxcraft/vixcraftsim (2020).
38. J. Hiller, H. Lipson, Dynamic simulation of soft multimaterial 3d-printed objects. *Soft robotics* 1, 88-101 (2014).
39. J. Hiller, H. Lipson, Automatic design and manufacture of soft robots. *IEEE Transactions on Robotics* 28, 457-466 (2011).
40. K. O. Stanley, Compositional pattern producing networks: A novel abstraction of development. *Genet Program Evol M* 8, 131-162 (2007).
41. N. Cheney, R. MacCurdy, J. Clune, H. Lipson, in *Proceedings of the 15th annual conference on Genetic and evolutionary computation*. (2013), pp. 167-174.
42. M. Schmidt, H. Lipson, in *Genetic programming theory and practice VIII*. (Springer, New York, N.Y., 2011), pp. 129-146.
43. F. Keijzer, M. van Duijn, P. Lyon, What nervous systems do: early evolution, inputoutput, and the skin brain thesis. *Adapt Behav* 21, 67-85 (2013).
44. F. Baluška, M. Levin, On Having No Head: Cognition throughout Biological Systems. *Front Psychol* 7, 902 (2016).
45. E. M. Eisenstein, *Aneural organisms in neurobiology*. Advances in behavioral biology v. 13 (Plenum Press, New York, 1975), pp. vii, 145 p.
46. L. N. Vandenberg, D. S. Adams, M. Levin, Normalized shape and location of perturbed craniofacial structures in the *Xenopus* tadpole reveal an innate ability to achieve correct morphology. *Developmental Dynamics* 241, 863-878 (2012).
47. R. A. Bilodeau, R. K. Kramer, Self-healing and damage resilience for soft robotics: a review. *Frontiers in Robotics and AI* 4, 48 (2017).
48. A. Urrios et al., A Synthetic Multicellular Memory Device. *Acs Synth Biol* 5, 862-873 (2016).
49. R. Sole et al., Synthetic collective intelligence. *Biosystems* 148, 47-61 (2016).
50. S. Manicka, M. Levin, The Cognitive Lens: a primer on conceptual tools for analyzing information processing in developmental and regenerative morphogenesis. *Philos Trans R Soc Lond B Biol Sci* 374, 20180369 (2019).
51. S. Manicka, M. Levin, Modeling somatic computation with non-neural bioelectric networks. *Sci Rep* 9, 18612 (2019).
52. S. Toda, L. R. Blauch, S. K. Y. Tang, L. Morsut, W. A. Lim, Programming self-organizing multicellular structures with synthetic cell-cell signaling. *Science*, (2018).

Example 2—Kinematic Self-Replication in Reconfigurable Organisms

Reference is made to Kriegman et al., "Kinematic self-replicatoin in reconfigurable organisms," Proc Natl Acad Sci USA. 2021 Dec. 7; 1189(49):e2112672118. doi: 10.1073/pnas.2112672118, the content of which is incorporated herein by reference in its entirety.

Abstract

All living systems perpetuate themselves via growth in or on the body, followed by splitting, budding, or birth. We find that synthetic multicellular assemblies can also replicate kinematically by moving and compressing dissociated cells in their environment into functional self copies. This form of perpetuation, previously unseen in any organism, arises spontaneously over days rather than evolving over millennia. We also show how AI methods can design assemblies that postpone loss of replicative ability and perform useful work as a side effect of replication. This suggests other unique and useful phenotypes can be rapidly reached from wild type organisms without selection or genetic engineering, thereby broadening our understanding of the conditions under which replication arises, phenotypic plasticity, and how useful replicative machines may be realized.

Significance

Almost all organisms replicate by growing and then shedding offspring. Some molecules also replicate, but by moving rather than growing: they find and combine building blocks into self copies. Here we show that clusters of cells, if freed from a developing organism, can similarly find and combine loose cells into clusters that look and move like they do, and that this ability does not have to be evolved or introduced by genetic manipulation. Finally, we show that AI can design clusters that replicate better, and perform useful work as they do so. This suggests future technologies may, with little outside guidance, become more useful as they spread, and that life harbors surprising behaviors just below the surface, waiting to be uncovered.

Introduction

Like the other necessary abilities life must possess to survive, replication has evolved into many diverse forms: fission, budding, fragmentation, spore formation, vegetative propagation, parthenogenesis, sexual reproduction, hermaphroditism, and viral propagation. These diverse processes however share a common property: all involve growth within or on the body of the organism. In contrast, a non-growth-based form of self replication dominates at the subcellular level: molecular machines assemble material in their external environment into functional self copies directly, or in concert with other machines. Such kinematic replication has never been observed at higher levels of biological organization, nor was it known whether multicellular systems were even capable of it.

Despite this lack, organisms do possess deep reservoirs of adaptive potential at all levels of organization, allowing for manual or automated interventions that deflect development toward biological forms and functions different from wild type (1), including the growth and maintenance of organs independent of their host organism (2,3,4), or unlocking regenerative capacity (5,6,7). Design, if framed as morphological reconfiguration, can reposition biological tissues or redirect self organizing processes to new stable forms without recourse to genomic editing or transgenes (8). Recent work has shown that individual, genetically unmodified prospective skin (9) and heart muscle (10) cells, when removed from their native embryonic microenvironments and reassembled, can organize into stable forms and behaviors not exhibited by the organism from which the cells were taken, at any point in its natural life cycle. We show here that if cells are similarly liberated, compressed, and placed among more dissociated cells that serve as feedstock, they can exhibit kinematic self replication, a behavior not only absent from the donating organism, but from every other known plant or animal. Further, replication does not evolve in response to selection pressures, but arises spontaneously over five days, given appropriate initial and environmental conditions.

Results

Figure 8:
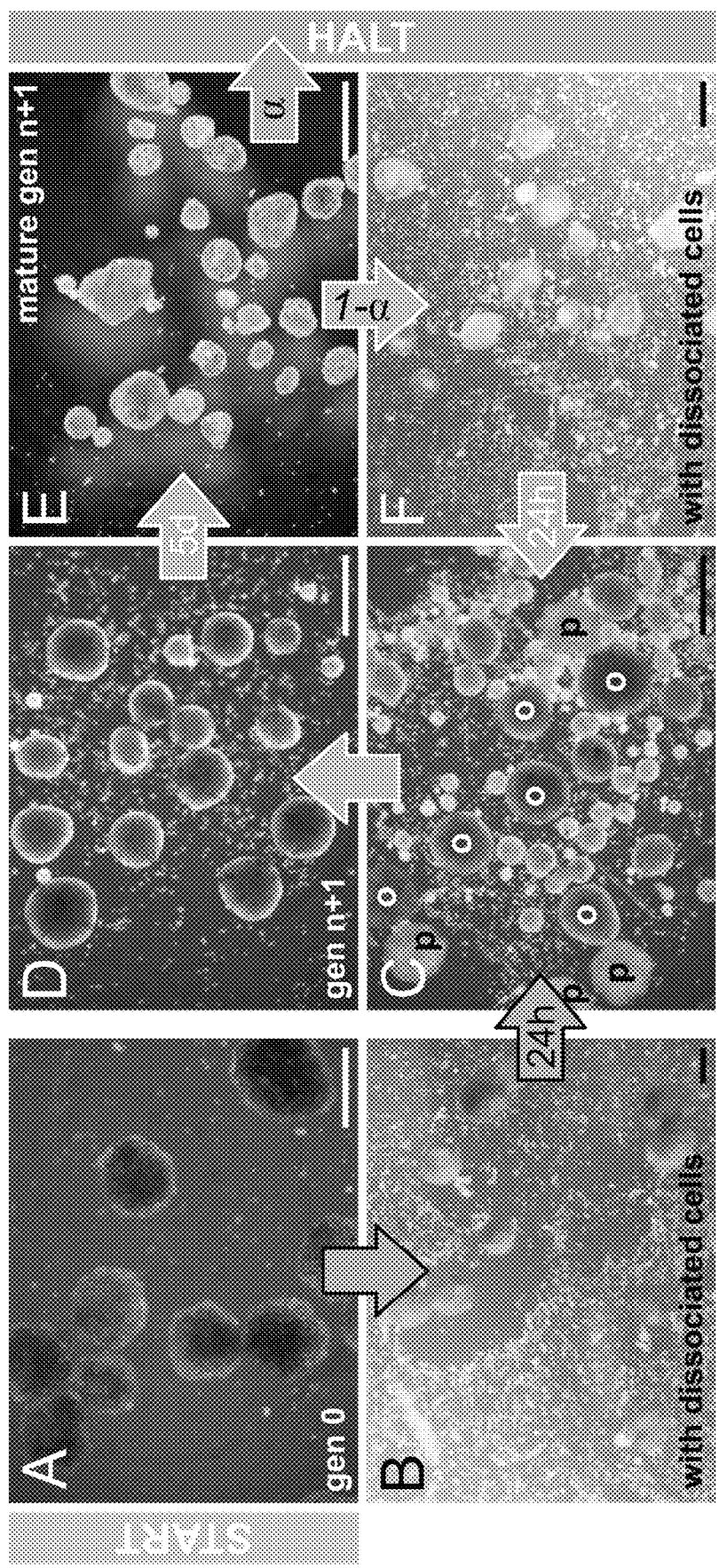
FIG. 8. Spontaneous kinematic self replication. (A) Stem cells are removed from early stage frog blastula, dissociated, and placed in a saline solution where they cohere into spheres containing 3000 cells. The spheres develop cilia on their outer surfaces after 3 days. When the resulting mature swarm is placed amid 60,000 dissociated stem cells in a 60 mm-diameter circular dish (B), their collective motion pushes some cells together into piles (C,D), which, if sufficiently large (at least 50 cells), develop into ciliated offspring (E) themselves capable of swimming, and, if provided additional dissociated stem cells (F), build additional offspring. In short, progenitors (p) build offspring (o), which then become progenitors. This process can be disrupted by withholding additional dissociated cells. Under these, the currently best known environmental conditions, the system naturally self replicates for a maximum of two rounds before halting. The probability of halting (a) or replicating (1-a) depends on a temperature range suitable for frog embryos, the concentration of dissociated cells, the number and stochastic behavior of the mature organisms, the viscosity of the solution, the geometry of the dish's surface, and the possibility of contamination. Scale bars indicate 500 microns.

Pluripotent stem cells were collected from the animal pole of *X. laevis* embryos (FIG. 12A) and raised for 24 h in 14° C. mild saline solution. These excised cells, if left together as an animal cap (11) (FIG. 12A,B) or brought back in contact after dissociation (12) (FIG. 12C,D), naturally adhere and differentiate into a spheroid of epidermis covered by ciliated epithelium (13,14) over five days (9) (Sect. S1; FIG. 8A). The resulting wild type reconfigurable organisms move using multiciliated cells present along their surface (which generate flow through the coordinated beating of hairlike projections) and typically follow helical trajectories through an aqueous solution for a period of 10-14 days, before shedding cells and deteriorating as their maternally-provided energy stores are depleted.

Previous studies reported spontaneous aggregation of artificial particles by groups of wild type self-organizing (9) and AI-designed (10) reconfigurable organisms: the particles were gathered and compressed as a side effect of their movement. Here, kinematic self replication was achieved by replacing the synthetic particles in the arena with dissociated *X. laevis* stem cells as follows.

When 12 wild type reconfigurable organisms are placed in a petri dish amid dissociated stem cells (FIG. 8B), their combined movement re-aggregates some of the dissociated cells into piles (FIG. 8C,D). Piled cells adhere, compact, and, over five days, develop into more ciliated spheroids (FIG. 8E) also capable of self propelled movement. These offspring are then separated from their progenitor spheroids and placed in a new petri dish containing additional dissociated stem cells (FIG. 8F). There, offspring spheroids build further piles, which mature into a new generation of motile spheroids.

In four of five independent trials using densities of 25-150 cells/mm$^2$, wild type reconfigurable organisms kinematically self-replicated only one generation. In the fifth trial, two generations were achieved. Each successive generation, the size and number of offspring decreased until offspring were too small to develop into self-motile organisms, and replication halted.

Figure 13:
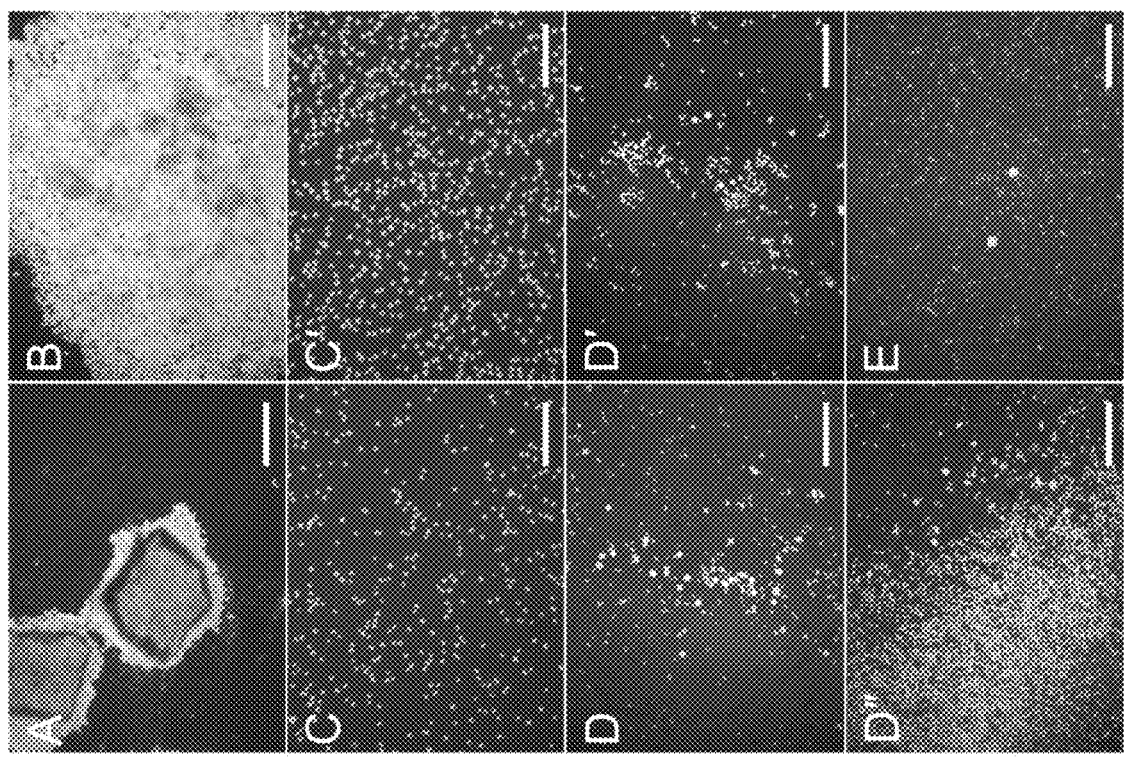
FIG. 13. Reconfigurable organisms are required for the generation of offspring. Dissociated stem cell layers are produced from animal cap tissue of Nieuwkoop and Faber stage 9 embryos (A), which naturally dissociates when placed in calcium-free, magnesium-free media (B). Pooled and washed cells can then be deposited into dishes at various concentrations (C, C'), providing the necessary material for self replication. This process required reconfigurable organisms to be present: offspring were never produced across three trials with dissociated stem cells only (D-D"). Any small aggregates fall apart over proceeding days of development, and no motile offspring were observed after 5 days (E). Scale bars indicate 500 microns.

To determine if offspring were indeed built by the kinematics of progenitor organisms rather than just fluid dynamics and self assembly, the dissociated stem cells were observed alone without the progenitors. With no progenitor organisms present, no offspring self-assembled at any of the stem cell concentrations tested (FIG. 13E).

Kinematic Self Replication

Given their rapid loss of replicative ability, reconfigurable organisms can be viewed as autonomous but partially functioning machines potentially amenable to improvement. Autonomous machines that replicate kinematically by combining raw materials into independent functional self copies have long been known to be theoretically possible (15). Since then, kinematic replicators have been of use for reasoning about abiogenesis, but they have also been of engineering interest: If physical replicators could be designed to perform useful work as a side effect of replication, and sufficient building material were discoverable or provided, the replicators would be collectively capable of exponential utility over time, with only a small initial investment in progenitor machine design, manufacture and deployment. To that end, computational (16,17,18), mechanical (19) and robotic (20-23) self replicators have been built, but to date, all are made from artificial materials and are manually designed. Kinematic self replication may also, in contrast to growth-based biological forms of reproduction, offer many options for automated improvement due to its unique reliance on self movement. If progenitor machines could be automatically designed, it may become possible to automatically improve machine replication fidelity (24), increase or alter the utility performed as a side effect of replication, allow replication to feed on more atomic materials (25), control replication speed and spread, and extend the number of replication cycles before the system suffers a loss of replicative ability. We introduce an AI method here that can indeed extend replication cycles by designing the shape of the progenitor reconfigurable organisms.

Amplifying Kinematic Self Replication

Determining sufficient conditions for self replication requires substantial effort and resources. Each round of replication takes one week, and regular media changes are required to minimize contamination. Thus, an evolutionary algorithm was developed and combined with a physics simulator to seek conditions likely to yield increased self replication, measured as the number of rounds of replication achieved before halting, in the simulator. Progenitor shape was chosen as the condition to be varied, as previous work demonstrated that shapes of simulated organisms can be evolved in silico to produce locomotion in cardiac tissue-driven reconfigurable organisms (10), or enhanced synthetic particle aggregation by ciliated-driven reconfigurable organisms (9).

Figure 9:
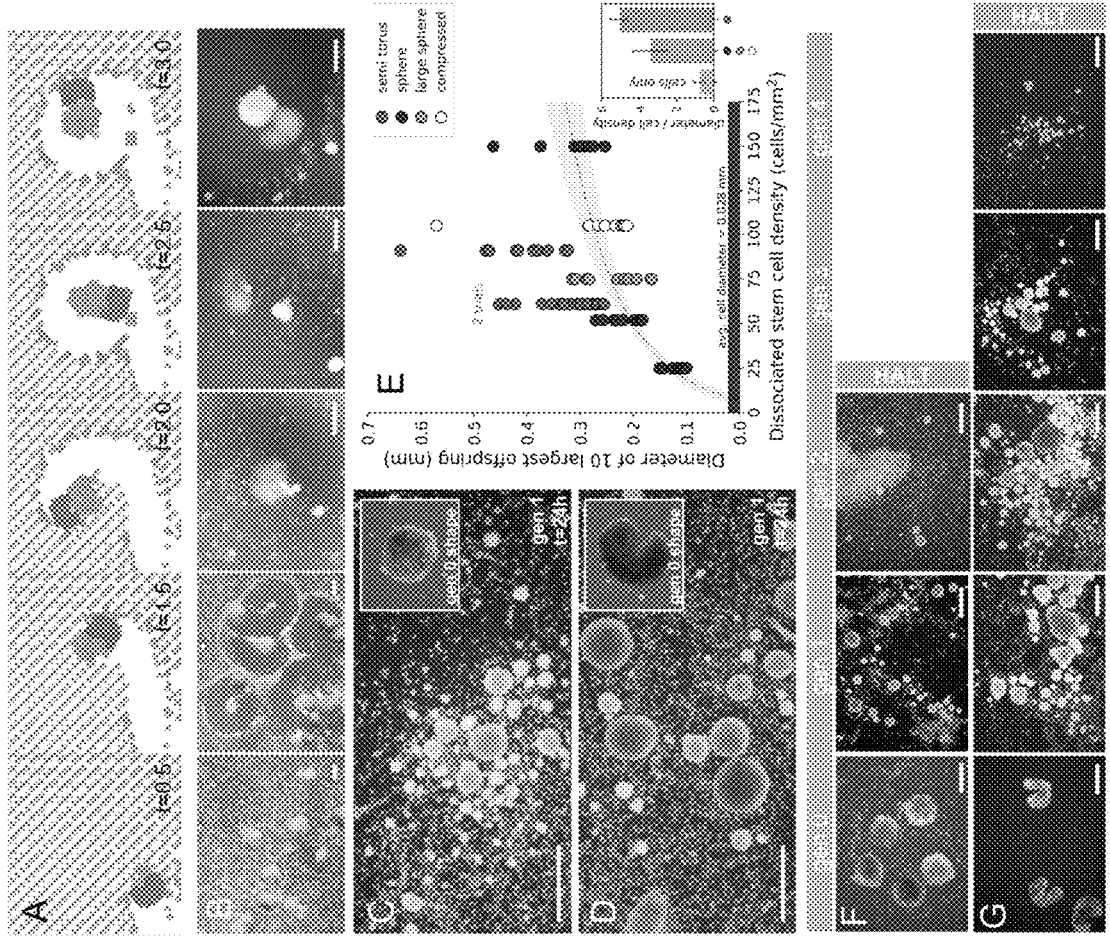
FIG. 9. Amplifying kinematic self replication. Due to surface tension, reconfigurable organisms naturally develop into ciliated spheroids, but they can be sculpted into non spheroidal morphologies manually during development to realize more complex body shapes. Progenitor shapes were evolved in silico to maximize the number of self replication rounds before halting. (A) Shapes often converge to an asymmetrical semitoroid (C-shape; pink) with a single narrow mouth in which dissociated cells (green) can be captured, transported, and aggregated. This evolved shape was fabricated and released in vivo (B), recapitulating the behavior observed in silico (A). Offspring built by wild type spheroids (C) were smaller than those built by the semitoroids (D), regardless of the size and aspect ratios of the spheroids, and across different concentrations of dissociated cells (F). The maximum of two rounds of self-replication achieved by the spheroids (F) was extended by the semitoroids to a maximum of four rounds (G). Scale bars indicate 500 microns.

Simulations indicated that some body shapes amplified pile size and replication rounds, while others damped or halted self replication. Some, but not all geometries were better than the spheroids. The most performant geometry discovered by the evolutionary algorithm in silico and manufacturable in vivo was a semi-torus (FIG. 9A). When 12 semitoroidal progenitor organisms were constructed and placed in an arena filled with densities of 61-91 dissociated stem cells/mm$^2$, they exhibited the same enhanced piling behavior in vivo observed in silico (FIG. 9B). The offspring produced by the progenitor spheroids (FIG. 29C) were significantly smaller than those produced by the progenitor semitoroids (FIG. 9D), although both progenitor groups produced spheroid offspring. Controlling for dissociated cell density, the diameter of offspring produced by progenitor spheroids was increased 149% by the progenitor semitoroids ($p<0.05$) (FIG. 9E). The replication rounds achieved by progenitor spheroids (mean=1.2+/−0.4SD, max of 2 shown in FIG. 9F) was increased 250% by the progenitor semitoroids (mean=3+/−0.8SD, max of four shown in FIG. 9G) ($p<0.05$). The only trial using semitoroids that reproduced less than three rounds was terminated early due to fungal contamination. Across the five trials with wild type progenitor spheroids and the three trials with AI-designed progenitor semitoroids, the size of the first generation of offspring correlated with the total number of generations achieved (rho=0.93; $p<0.001$).

Given the observation that larger spheroids yielded more replication rounds, another, simpler route to increasing self replication seemed possible: increasing the density of dissociated cells. However, FIG. 9E shows that spheroid offspring size does not appreciably increase even when tripling density from 50 to 150 cells/mm$^2$ in the presence of sphere progenitors.

Figure 10:
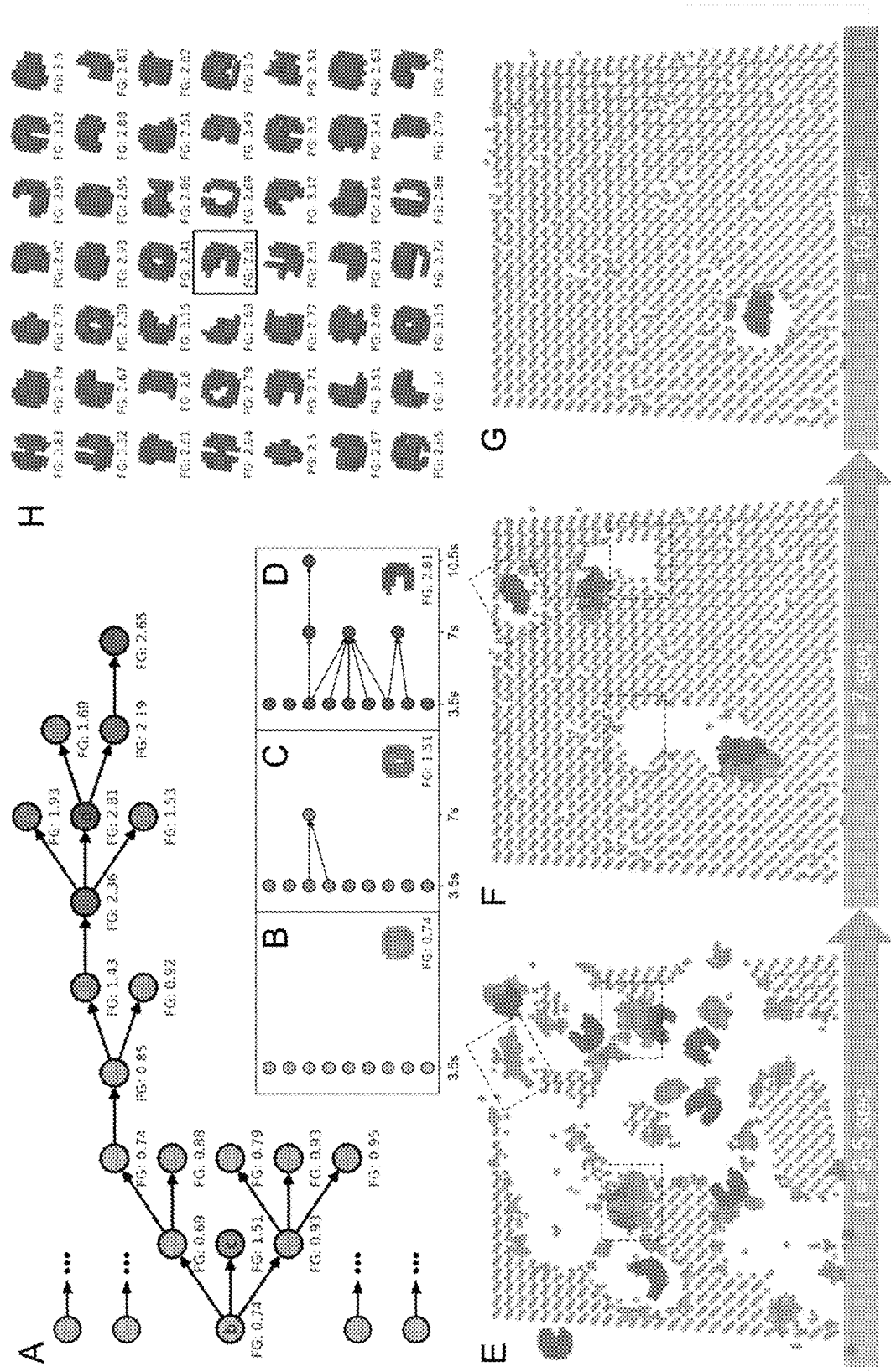
FIG. 10. Evolving self-replication. (A) An evolutionary algorithm, starting with random swarms, evolves swarms with increasing self replicative ability. (FG=number of filial generations achieved by a given swarm. The fractional part denotes how close the swarm got to achieving another replication round.) The most successful lineage in this evolutionary trial originated from a spheroid that built piles no larger than 74% of the size threshold required to self-replicate (B). A descendent swarm composed of nine flexible tori (C) contained two members that built one pile large enough to self-replicate (two arrows), which, alone, built piles no larger than 51% of the threshold. A descendent of the toroid swarm, a swarm of semi-tori (D), contained six members (E) that collectively built three piles large enough to mature into offspring (F). One of those offspring built a pile large enough to mature into a second generation offspring (G). An additional 48 independent evolutionary trials (H) evolved self replicative swarms with diverse progenitor shapes.
Figure 17:
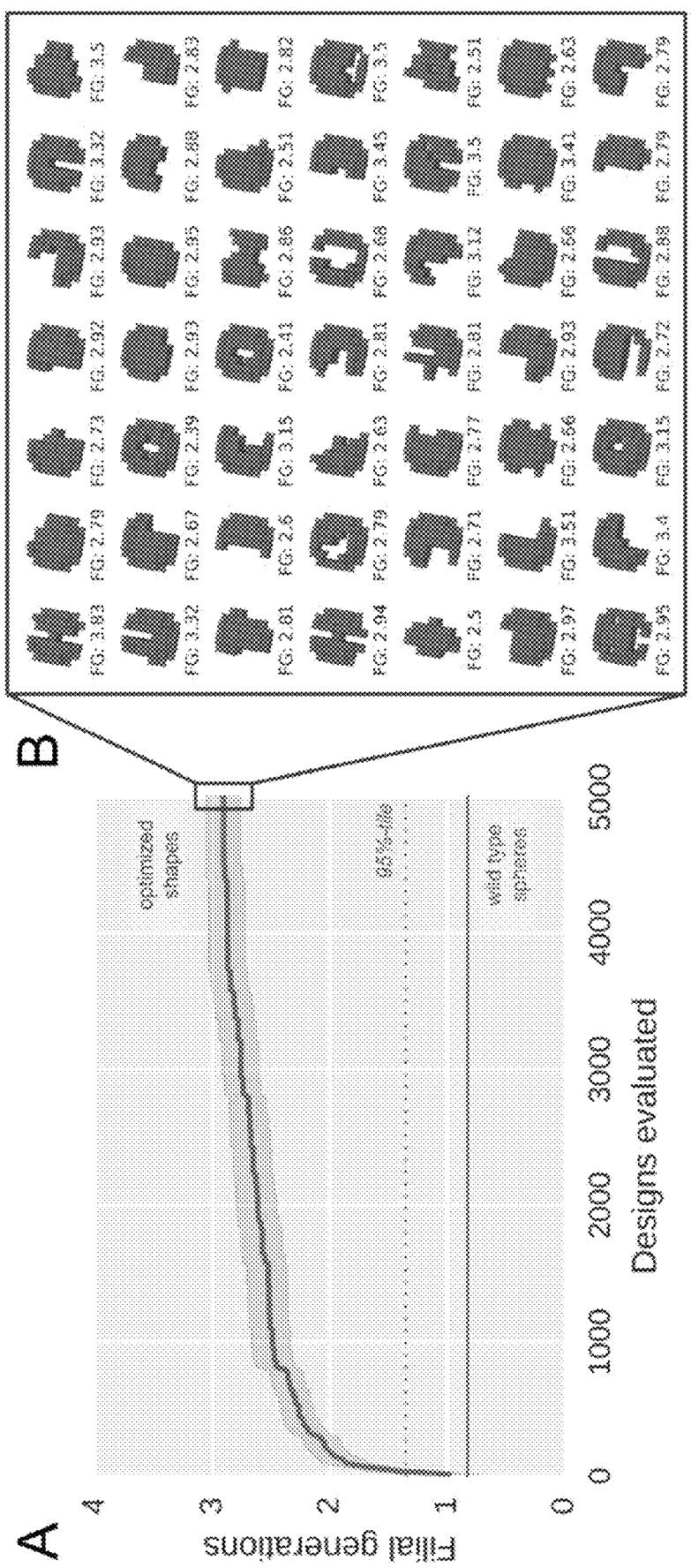
FIG. 17. Amplifying self replication via morphology optimization in silico. Forty nine optimization trials were conducted (A), each of which starts with the evaluation of a swarm of wild type spheroids, in silico, under random swimming trajectories as derived from a unique set of random cilia forces. These 49 independent random cilia forces were held constant while body shape was optimized. Starting from 49 different randomly generated populations of 16 body shapes, the optimizer randomly removes voxels from the sphere, selecting shapes that result in more self replication. At the end of optimization, the highest amount of self replication produced by each of the 49 trials (B) was compared against the amount of self replication produced by the wild type spheres. The solid blue and red lines indicate mean fitness (whose integer part is the number of filial generations produced; Eqn. 1) across optimization time in silico for the optimized and wild type body shapes, respectively. Ninety-five percent bootstrapped confidence intervals (95%- and 5%-tiles) are drawn as shaded blue regions around the mean fitness of the optimized design; the dotted red line denotes the 95%-tile of fitness for the wild type spheres.

The semitoroidal design was found in silico using an evolutionary algorithm (FIG. 10A). First, sixteen progenitor shapes are randomly generated. For each shape, nine simulated organisms with that shape are evaluated within a simulated petri dish (FIG. 10E). If the swarm creates piles large enough to mature into offspring, the simulated offspring are transferred to a fresh dish (FIG. 10F) and the process continues (FIG. 10G). When self replication halts, the shape is assigned a performance score computed as the number of filial generations achieved. Higher performing progenitor shapes are copied, mutated, and replace shapes in the population with poorer performance. Each of the newly-created progenitor shapes is expanded into a swarm, simulated, and scored (FIG. 310C). The algorithm terminates after a fixed amount of computational effort has been expended, and the shape that produced the most replication rounds is extracted (FIG. 10D). Forty nine independent optimization trials were conducted, yielding 49 high performing progenitor shapes (FIG. 10H) that, in silico, produce larger offspring ($p<0.0001$) and more replication rounds ($p<0.0001$) than simulated wild type spheroids (FIG. 17).

Figure 18:
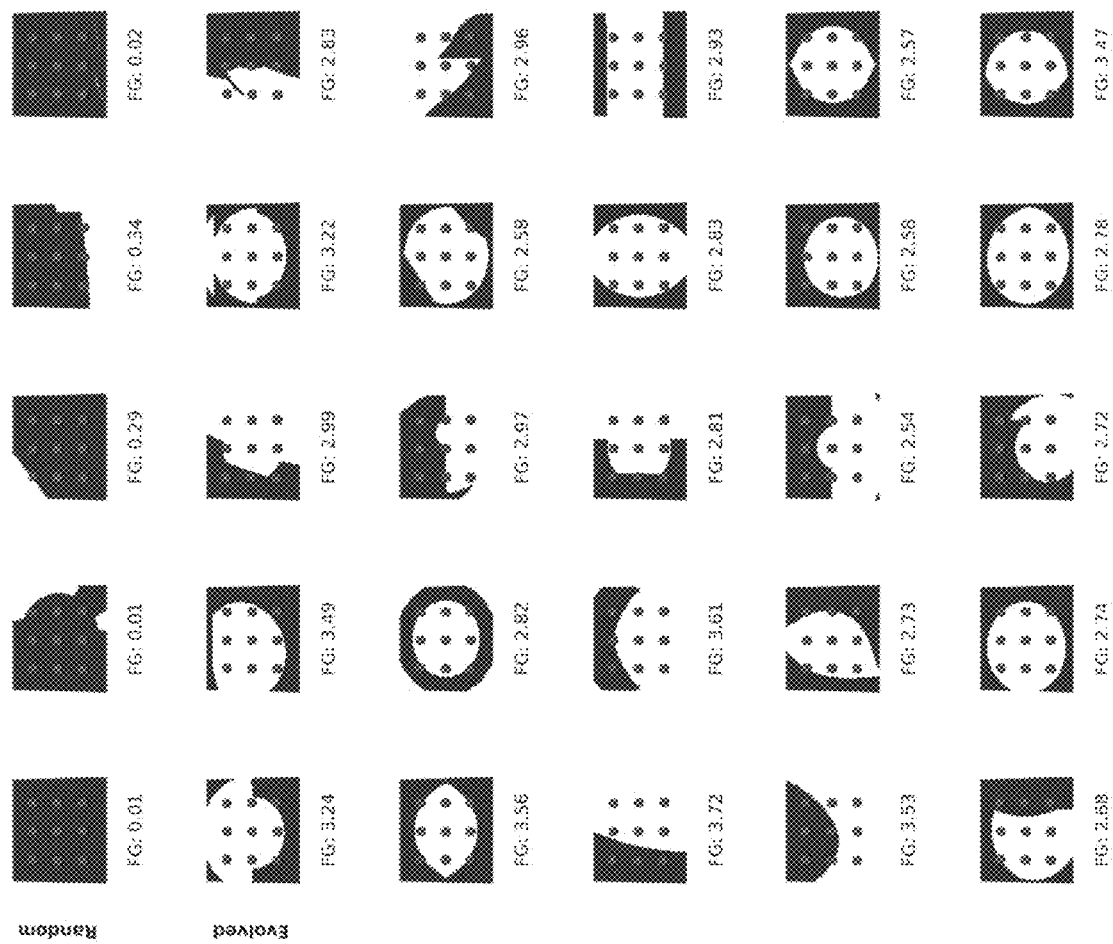
FIG. 18. Controlling self replication via terrain optimization in silico. There are many tunable parameters that affect the efficacy of kinematic self replication in reconfigurable organisms. In addition to optimizing organism shape to increase self replication, we optimized the structure of the terrain. Black, immovable and unpassable voxels were added along the surface of each simulated petri dish. These barriers act as guide rails, channeling the random swimming of the unsculpted wild type spheres (pink) along certain trajectories. Instead of determining where to carve away tissue from a spherical body, the optimization algorithm now determines where to place black voxels on the surface plane. Random terrains trap the organisms, inhibiting self replication (top row). Optimized terrains reliably increased self replication compared to both random terrains and flat terrains without black voxels.
Figure 19:
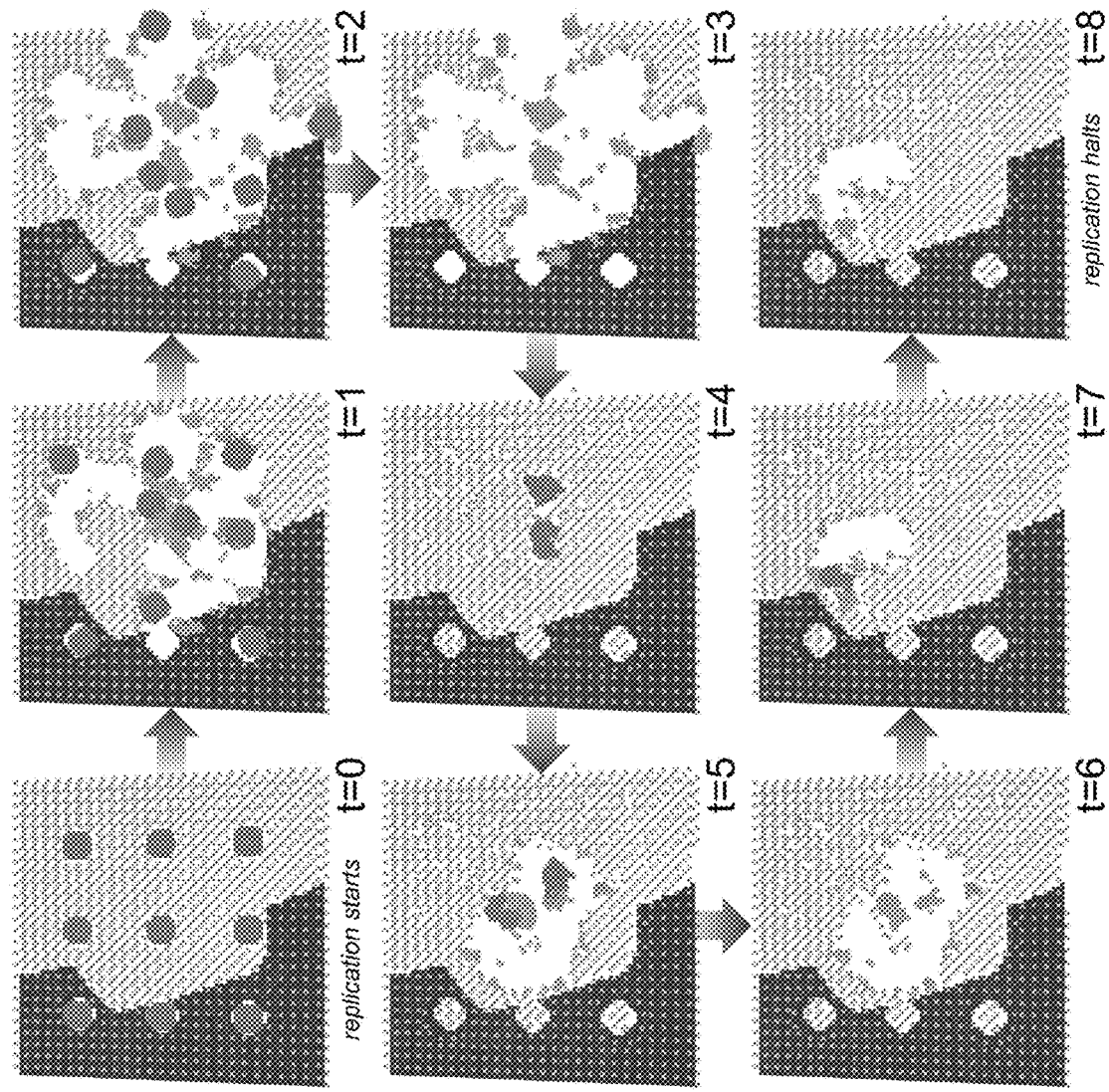
FIG. 19. An optimized terrain that amplifies self replication in wild type reconfigurable organisms. One of the optimized terrains (black voxels) that amplified self replication in silico, yielded two filial generations of pile building after the initial swarm. On flat terrain (without black voxels), no replication occurs on average: the average number of filial generations is below one.

Conditions other than progenitor shape can be optimized to improve self replication. To that end, the algorithm was modified to evolve terrain shape rather than progenitor shape to amplify self replication in silico for wild type spheroid progenitors. Terrain was shaped by the inclusion of reconfigurable walls that, once positioned along the bottom surface of the simulated dish, constrain the stochastic movement of organisms along more predictable trajectories within predefined limits. Starting with randomly generated terrains, the algorithm evolved terrains that, in silico, increased the number of replication rounds achieved by the wild type spheroid progenitors, compared to their performance on a flat surface ($p<0.0001$) (FIGS. 18-19).

Figure 20:
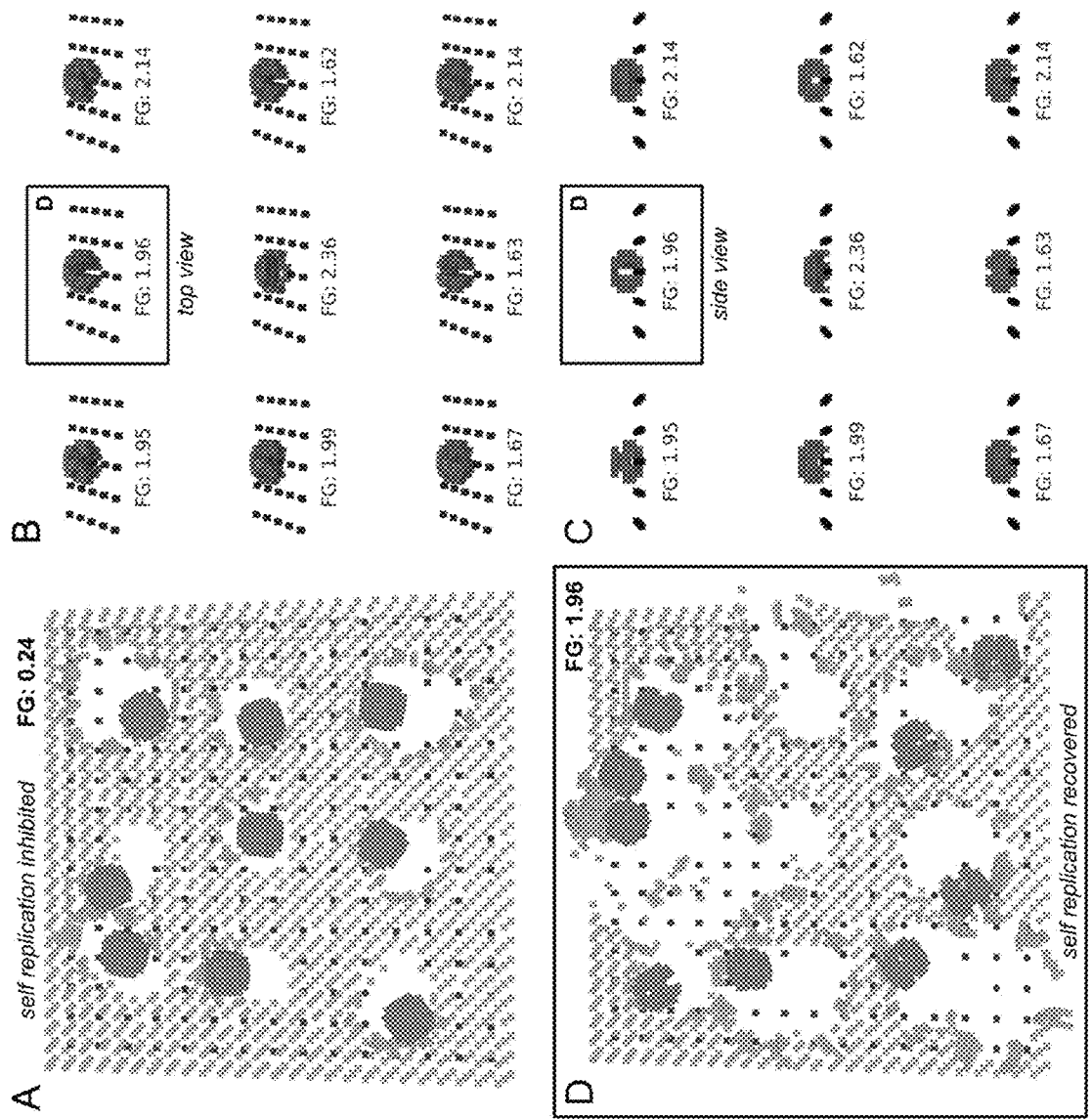
FIG. 20. Recovering self-replication in a cluttered environment in silico. A static grid of unpassable black voxels were placed on the bottom of the simulated dish. In this cluttered environment, the wild type spherical organisms could no longer move enough to build offspring (A). Their ability to spontaneously self-replicate was lost. However, by optimizing organism shape, self replication can be recovered. The results of nine independent evolutionary trials are shown here at two different perspectives: from above (B) and from the side (C). The evolutionary algorithm discovered how to raise the organisms on stilts so they can glide over the top of the clutter and rescue function: aggregating loose stem cells into piles large enough to develop into offspring (D).

The algorithm not only can amplify kinematic self replication in a given environment but can also bestow this capability on swarms otherwise incapable of achieving it in adverse environments. In a cluttered environment, the wild type progenitors cannot move enough to self replicate. However, the algorithm discovered progenitor shapes with ventral surfaces that elevated the simulated organisms above the clutter while maintaining frontal plane curvatures that facilitated pile making and the achieving of self replication (FIG. 20).

Figure 21:
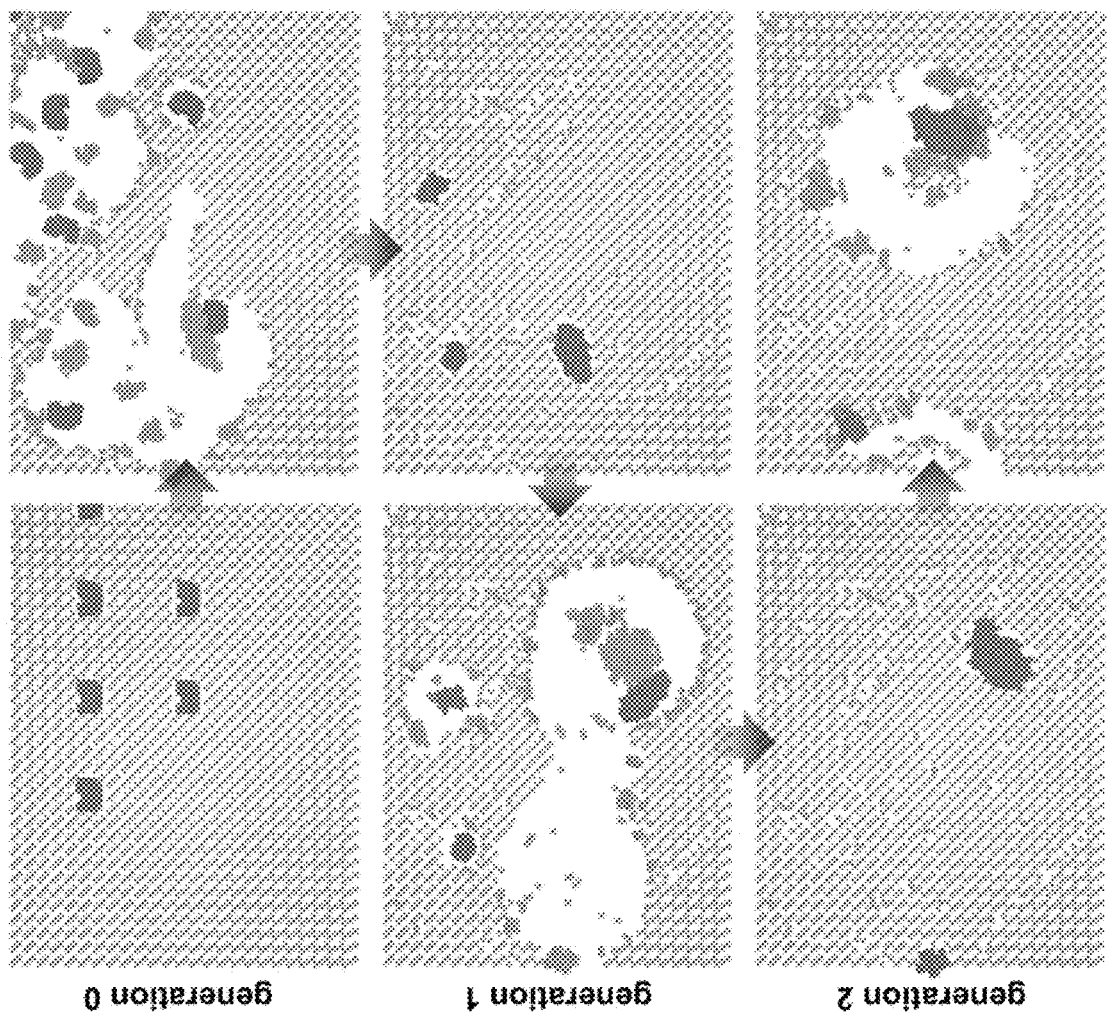
FIG. 21. Increasingly larger offspring in silico. Reconfigurable organisms can create offspring that are larger than parents, and this enlarging process can persist for multiple rounds of replication in silico.

In contrast to other known forms of biological reproduction, kinematic self replication allows for the opportunity to significantly enlarge and miniaturize offspring each generation. This was observed in vivo (FIG. 8G) and in silico (FIG. 21). This suggests that swarms may be automatically designed in future to produce offspring of diverse size, shape and useful behaviors beyond simply more self replication.

Figure 22:
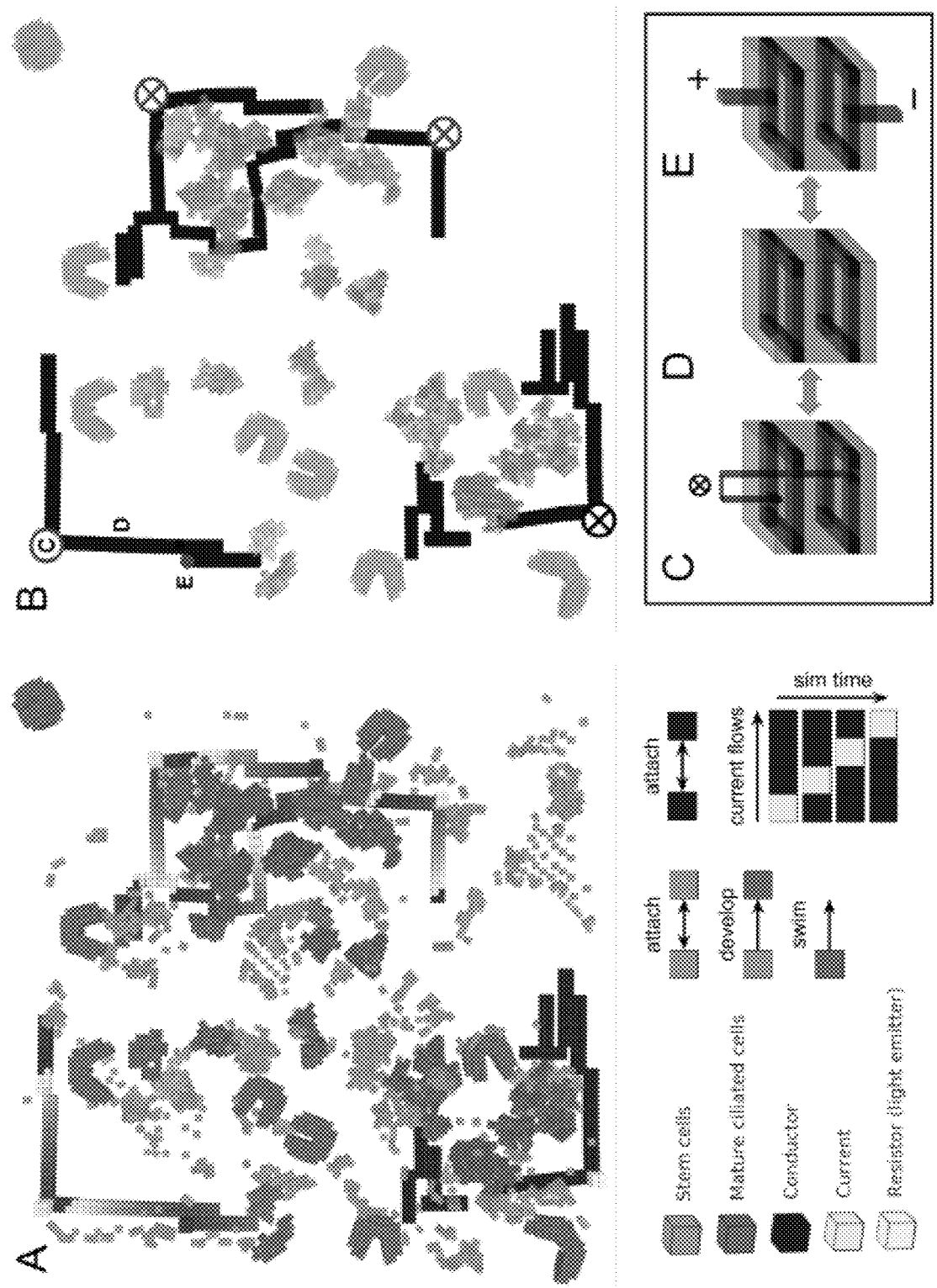
FIG. 22. The simulated circuit completion task. A swarm of simulated kinematically self-replicating reconfigurable organisms was placed inside a petri dish alongside simulated modular electronic components (A) that can freely move and rotate along a surface plane, and connect on contact. For clarity, the dish is shown in grayscale, without the loose stem cells (B). There are three simulated electronic modules: light emitter (C), wire (D), and power supplies (E).

Exponential Utility von Neumann's original self replicating machine (15) was capable in theory of not just building a functional self copy, but also other machines as a side effect of the replicative process. If these tangential machines performed useful work, the entire system was capable of exponential utility. As long as sufficient feedstock was available, only a small expenditure of energy and manufacture was required to build the first replicative machine. To estimate whether the self replicating reconfigurable organisms introduced here may be capable of exponential utility, we created a computational model using known features of the physical semitoroids to forecast their potential rate of increase in utility. It is assumed that progenitor machines will be placed in semi-structured environments, sufficient feedstock will be within reach, and random action of the swarm will be sufficient to result in useful work. Given these requirements, the task of microcircuit assembly was chosen (FIG. 11A). Although current circuit assembly systems are fast, efficient and reliable, in situ repair or assembly of simple electronics in hostile or remote environments is currently impossible using traditional robots, rendering this a use case worthy of investigation. The simulated environment contains microscale power supplies (26), light emitters (27), and disconnected flexible adhesive wires (28) (FIG. 22). Random action by swarm members can inadvertently move wires and close a circuit between a power supply and a light emitter (FIG. 11A), considered here as useful work. The environment is also assumed to contain dissociated stem cells, such that offspring organisms may be built in parallel with circuit assembly. If any offspring are built, they are divided into two groups and moved into two new dishes with more electronic components and stem cells (FIG. 11B,C). If no offspring are built, the process terminates (FIG. 11D). In this model, utility increases quadratically over time (FIG. 11E).

Superlinear utility here depends on a superlinearly increasing supply of dissociated stem cells. This may be more achievable than mining artificial materials for non-biological robot replicators given that a single female *X. laevis* can produce thousands of eggs daily, with each embryo containing ~3000 cells for dissociation, and *X. laevis* itself is capable of reproduction and thereby superlinearly increasing egg production. Reconfigurable organisms are thus constructed from a renewable material source which requires less invasive component sourcing than other existing self-motile biological machines (29,30). The quadratic increase in utility predicted by the model in FIG. 11 may not be achievable when in situ circuit assembly and repair matures and the model can be tested empirically. But, as long as the components are small enough in weight and size to be moved, an acceptable temperature range is maintained, sufficient components have already been created and deployed and are nontoxic, and self replication is maintained, the system will produce superlinear increases in utility. This can be contrasted with non-replicative robot technology for the same task, which would require superlinear investments in robot construction, deployment and maintenance to realize superlinear utility.

Discussion

The ability of genetically unmodified cells to be reconfigured into kinematic self replicators, a behavior previously unobserved in plants or animals, and the fact that this new replicative strategy arises spontaneously rather than evolves, further exemplifies the developmental plasticity available in biological design (1-8). Although kinematic self replication has not been observed in extant cellular life forms, it may have been essential in the origin of life. The amyloid world hypothesis (31), for instance, posits that self assembling peptides were the first molecular entity capable of self replication, and would thus represent the earliest stage in the evolution of life, predating even the RNA world. Unlike self-replicating RNAs which template themselves during replicative events, amyloid monomers can form seeds which produce a variety of amyloid polymorphs, yielding either larger or smaller 'offspring' depending on peptide availability, kinematics, and thermodynamic conditions. This variation is similar to modern day prions, where self-propagating mis-folded proteins are capable of forming aggregates of multiple sizes and polymorphisms (32). Although reconfigurable organisms are not a model for origin of life research, which strives to describe the first information unit capable of self replication, they may shed light on its necessary and sufficient initial conditions.

Traditional machine self replication is assumed to require a constructor, a copier, a controller, and a blueprint to describe all three (15). However, there are no clear morphological or genetic components in the organisms described here that map onto these distinct structures. The concept of control in reconfigurable organisms is further muddied by their lack of nervous systems and genetically modified behavior. This suggests that reconfigurable organisms may in future contribute to understanding how self-amplifying processes can emerge spontaneously, in new ways and in new forms, in abiotic, cellular, or biohybrid machines, and how macroevolution may proceed if based on kinematic rather than growth-based replication.

Today, several global challenges are increasing superlinearly in spatial extent (33), intensity (34), and frequency (35), demanding technological solutions with corresponding rates of spread, adaptability, and efficacy. Kinematic self replication may provide a means to deploy a small amount of biotechnology that rapidly grows in utility, but which is designed to be maximally controllable (36) via AI-designed replicators. Even if the behaviors exhibited by reconfigurable organisms are currently rudimentary, such as those shown in past (10) and this current work, AI design methods have been shown to be capable of exploiting this flexibility to exaggerate these behaviors and, in future, possibly guide them toward more useful forms.

Materials and Methods

Manual construction of reconfigurable organisms. Wild type reconfigurable organisms were constructed manually from amphibian *Xenopus laevis* epidermal progenitor cells using methods described previously (9). Briefly, fertilized *Xenopus* eggs were cultured for 24 h at 14° C. [Nieuwkoop and Faber stage 10; (37)] in 0.1× Marc's Modified Rings (MMR), pH 7.8, after which the animal cap of the embryo was removed with surgical forceps (Dumont, 11241-30 #4) and transferred to 1% agarose coated petri dish containing 0.75×MMR. Under these conditions, the tissue heals over the course of 1 h and differentiates into a ciliated spheroid capable of locomotion after 4d of incubation at 14° C. Water exchanges were done three times weekly, and the organisms were moved to fresh 1% agarose coated petri dishes containing 0.75×MMR and 5 ng/µl gentamicin (ThermoFisher Scientific, 15710072) until ready for experimental use.

For non-spheroid designs, morphology was shaped via microcautery and microsurgery (FIG. 12E-II). The initial production of these organisms began using the methods described above, however, after 24 h at 14° C. the spheroids were subjected to 3 hours of compression with a force of 2.62 mg/mm². This compression results in a mild flattening of the developing tissue, producing a disk that is more amenable to shaping because it is less likely to rotate out of plane. Following compression, the organisms were cultured for an additional 24 h at 14° C., after which final shaping was performed. Shaping was accomplished using a MC-2010 micro cautery instrument with 13 micron wire electrodes (Protech International Inc., MC-2010, 13-Y1 wire tip cautery electrode) in combination with a hand sharpened pair of surgical forceps. Each organism was shaped by first subtracting tissue to make a coarse morphology, then by fine sculpting to remove any cellular debris. After 1 h of healing the morphology became stable for the remainder of the organism lifespan. Following shaping, individuals were moved to fresh 1% agarose coated petri dishes containing 0.75×MMR and 5 ng/µl tlgentamicin and cultured until ready for experimental use.

All animal use was approved by the Institutional Animal Care and Use Committee and Tufts University Department of Laboratory Animal Medicine under protocol number M2020-35.

Dissociated stem cells. Dissociated cell layers for all self-replication experiments were obtained from the same starting material as the manually constructed reconfigurable organisms: *Xenopus laevis* embryos 24 h of age (raised 14° C.). Similar to the manual construction of reconfigurable organisms, the animal cap of each embryo was explanted and the rest of the tissue was discarded. Excised tissue was then moved via transfer pipette to a fresh 1% agarose coated petri dish containing a calcium-free, magnesium-free, dissociation medium (50.3 mM NaCl, 0.7 mM KCl, 9.2 mM $Na_2HPO_4$, 0.9 mM $KH_2PO_4$, 2.4 mM $NaHCO_3$, 1.0 mM edetic acid [EDTA], pH 7.3) and allowed to sit for five minutes. The pigmented outer ectoderm layer does not break down in this solution and was gently separated from the underlying stem cells with surgical forceps and discarded. The remaining tissues were agitated with manual flow from a pipetman until fully dissociated.

Material from 30 embryos were combined into a pool of cells (progenitor organisms are made from the same material, taken from a single embryo, and are composed of approximately 3,000 cells), which was then collected and transferred to a sterile eppendorf tube containing 1 ml of 0.75×MMR. This solution was further mixed via manual pipetting up and down an additional five times, creating a final stem cell suspension. Using a clean transfer pipette, this solution was moved to a new 1% agarose coated petri dish containing 0.75×MMR. The speed and angle of the suspension deposition determined the concentration of the cells in the dish, and this concentration was quantified by imaging five random areas in the arena, then counting and averaging the number of cells per sq. mm. Cells were allowed to settle for 2 minutes before beginning kinematic self replication experiments.

Conditions for kinematic self replication. All experiments were initiated by distributing a stem cell suspension into a 1% agarose coated 60×15 mm petri dish filled with 15 ml of 0.75×MMR, as described above. Dishes were placed on the stage of a stereo microscope equipped with an eyepiece mounted camera allowing for still photographs and time-lapse imaging across the duration of the experiment. Cell suspensions were allowed to settle for 2 minutes, after which an image was captured of the center of the arena, for cell density quantification. Following the initial setup, 12 adult organisms were placed in the center of the area among the dissociated cells via transfer pipette. All experiments were performed with adult reconfigured organisms aged 5 to 6 days at 14° C., as this time point was previously found to represent the middle of their lifespan, and provides a standard movement rate (9).

Combinations of progenitors and dissociated stem cells were allowed to interact overnight (20 h total trial length) at 20° C., and once the progenitors were placed in the arena, the petri dishes were not moved or manipulated in any way to avoid disturbing the dissociated cell distribution. Imaging lights were also turned off for the duration of each generation of self replication, as the heat generated by the light source was found to induce mild convection currents in the solution. Following completion of a generation, dishes were immediately imaged under the stereo microscope, and then moved to a Nikon SMZ-1500 microscope with substage illumination for offspring size quantification. All aggregated stem cell tissue, now compacted as individual spheroids, were then pipetted to the center of the dish and offspring size was calculated by measuring the diameter of each spheroid in the dish.

Upon completion of self replication, adult organisms were returned to their original dishes, and their spheroid offspring were moved to a fresh 1% agarose coated petri dish containing 0.75×MMR and 5 ng/μl gentamicin. Each dish is washed as often as necessary to remove any remaining loose stem cells. The offspring were then cultured 14° C. for 5 to 6 days to verify the mobility and viability of the following generation. Where applicable, further rounds of replication proceed exactly as the first: 12 individuals (the largest individuals are chosen in successive generations) are placed among feeder cells, allowed to self-replicate for 20 hours, and then offspring are quantified and separated for culture.

Evolving swarms in silico. An evolutionary algorithm (38) was used to evolve simulated swarms with better self replication, and for exhibiting diverse ways of doing so. Each independent trial starts with its own unique set of 16 initially random, genetically encoded replicator shapes. Each encoding is evaluated by prompting it to generate its shape, that shape is copied eight times, the resulting nine-progenitor swarm is simulated, and the amount (if any) of self replication is recorded. The process is repeated 15 times with each of the remaining encodings. Each of the 16 encodings is then copied, randomly modified, and the swarm it generates is simulated. A thirty-third, random encoding is added to the expanded population to inject genetic novelty into the population, and its swarm is also simulated and scored. Encodings are then evaluated in pairs: if one encodes a swarm more self replicative and evolutionarily younger than that encoded by the other, the latter encoding is deleted. Giving a selective advantage to younger swarms in this way maintains diversity in the population. Pairwise competitions continue until the population is reduced back to 16 encodings. This process of random variation, simulation, and selection is repeated for 48 hours of wall-clock time on eight NVIDIA Tesla V100s.

Generating initial swarms in silico. Each replicator shape was encoded as a generative neural network (39) that places voxels at some positions within an empty volume of fixed size. The largest contiguous collection of voxels output by the network was taken to be the shape of the replicator. Randomly modifying the edges or nodes in the network modifies the shape it generates.

Figure 16:
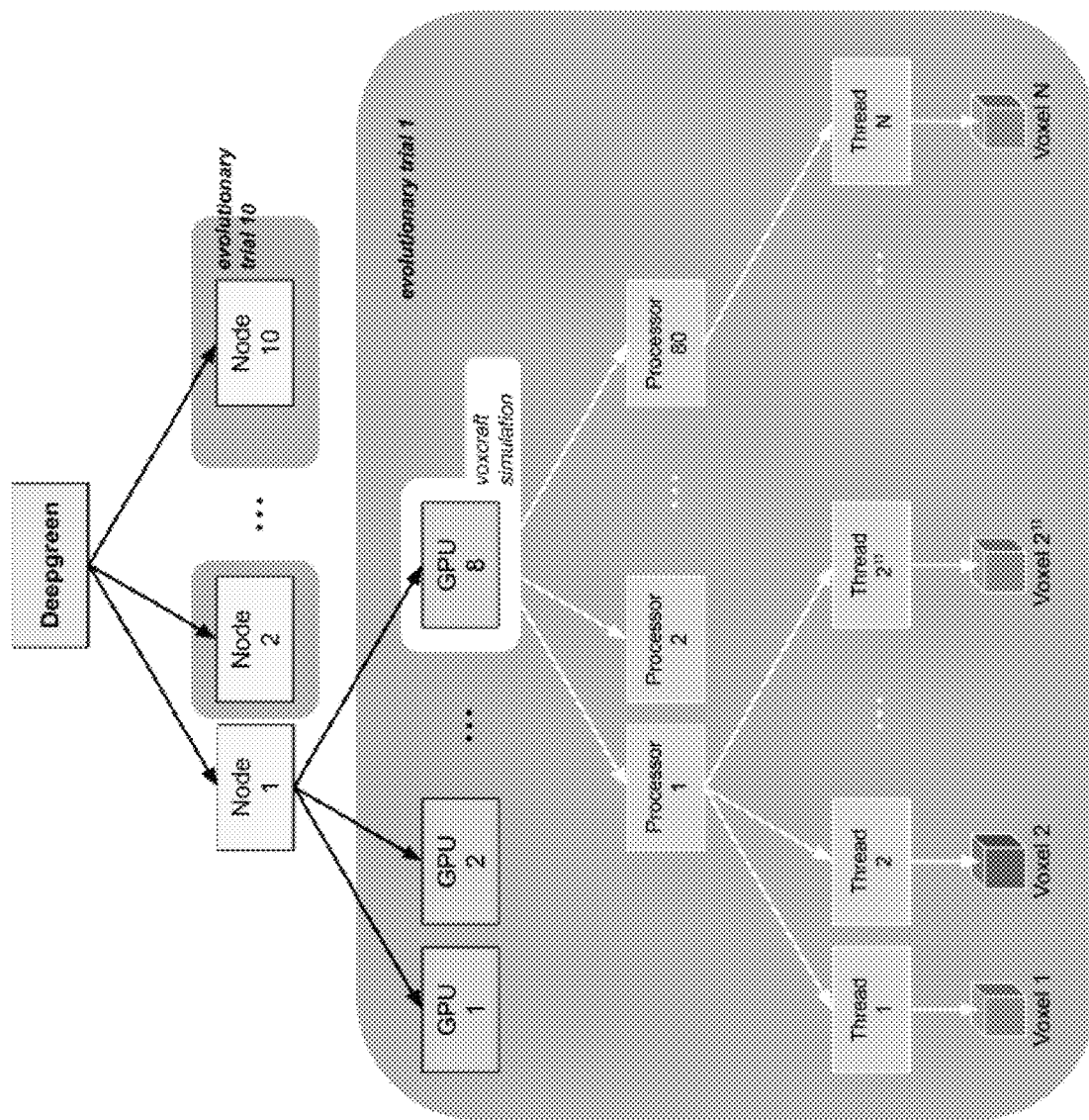
FIG. 16. GPU-accelerated simulations. Deepgreen is a high performance computing cluster at the University of Vermont which contains ten Nvidia GPU nodes. Each Nvidia node has eight Tesla V100s that are capable of running the CUDA programming platform, which was a requirement of the employed simulator, voxcraft-sim. We parallelized evolutionary trials across different nodes: On each node, an independent trial maintained a population of 16 designs, which were evaluated in batches of eight designs at a time, in parallel, across the node's eight GPUs. Each simulation contains a single design, which consists of N voxels. At each time step of simulation (numerical integration), the dynamics (position, velocity and acceleration) of each voxel within a simulation (on the order of 10 4 to 10 5 voxels) were evaluated concurrently on separate threads. Note that the number of voxels that can be updated in parallel will be constrained by the main memory bandwidth well before the number of voxels approaches the total number of potentially independent threads (80×2 11=163, 840).

Simulating replication. Reconfigurable organisms and dissociated stem cells were simulated as elastic voxels using a version of a voxel-based soft-body simulator (40) modified to run on GPU-based platforms (FIG. 16). Interactions between two voxels are modeled as deformations of an Euler-Bernoulli beam (translational and rotational stiffness). Collisions between voxels and the bottom of the petri dish are resolved by Hookean springs (translational stiffness). The height of the aqueous solution, and the walls of the petri dish, were modeled as soft boundaries that repel voxels penetrating predefined bounds with an opposite force proportional to the squared penetration (Sect. S2.1). The aggregate metachronal wave force produced by patches of cilia was modeled as an impulse force against each surface voxel, pointing in any direction in the horizontal (x,y) plane. The vertical (z) moments and forces of a simulated organism's voxels were locked in plane to better approximate the behavior of the physical organisms which maintained constant dorsoventral orientation. The dissociated stem cells were simulated by adhesive voxel singletons with neutral buoyancy, and were free to be moved and rotated in 3D space. When two adhesive voxels collided with each other, they bonded. Compaction and spherification, observed in vivo, is modeled in simulated piles of stem cells by stochastically detaching voxels around the surface of a pile, applying forces pulling them inward toward the center of the pile. Voxels were simulated with material properties manually tuned to allow for the largest stable time step of numerical integration. All other parameters of the model were estimated from biology according to Table 1.

TABLE 1

The parameters of kinematic self replication in reconfigurable organisms. Properties of the environment (1-5), reconfigurable organisms (6-16), and dissociated stem cells (17-26) are grouped under these three categories.

| no. | Parameter | In vivo | In silico |
|---|---|---|---|
| 1 | Temperature | 18-20° C. | N/A |
| 2 | Size of dish | 60 mm in diameter | Soft 81 × 81 × 5 boundaries. |
| 3 | Arena substrate | Arena substrate 1% agarose dissolved in 0.75x MMR | Coulomb friction: 1.0 and 3.0 static and dynamic coefficients, respectively. |
| 4 | Terrain | Terrain | Terrain |
| 5 | Wall forces | The substrate forms a gradual incline at the edge of the dish, due to the meniscus formed during agarose cooling. | A soft constraint that gradually pushes organisms back toward the center of the dish, if they move outside predefined bounds. |

TABLE 1-continued

The parameters of kinematic self replication in reconfigurable organisms.
Properties of the environment (1-5), reconfigurable organisms (6-16), and
dissociated stem cells (17-26) are grouped under these three categories.

| no. | Parameter | In vivo | In silico |
|---|---|---|---|
| 6 | Initial parents' starting position | Reconfigurable organisms were rarely seen at the very edge. Deposited in center of dissociated stem cells from above | Evenly spaced in a 3 by 3 grid, 15 voxel lengths apart, in the center of the dissociated stem cells. |
| 7 | Number of initial Parents | 12 | 9 during optimization: just enough to observe self replication occur while keeping the total number of voxels below 3000 to reduce simulation time. |
| 8 | Number of cells in parents | ~3,000 | 161 voxels |
| 9 | Volume of initial parents | 0.065-0.130 cubic mm | 161 voxel length$^3$ |
| 10 | Length of initial parents. | 400-600 μm | 7 voxels wide |
| 11 | Shape of initial parents | spheroids, toroids, semitoroid, compressed | See FIG. 17 |
| 12 | Width/height of initial parents | spheres: 1:1, toroids and semitoriods: 3:1, compressed 4:1 | 7:5 voxel aspect ratio |
| 13 | Cilia force | PIV analysis | Impulse forces mediated by global damping. |
| 14 | Collisions | Cells and tissues deform elastically. | Voxels are elastic: they deform against objects and recoil from them. |
| 15 | Replication time length | 20 hours | 3.5 seconds (16,366 time steps, step size 0.000214 sec) |
| 16 | Time to senescence | 10 days | 3 seconds of simulation time, which was sufficient for simulated spheroids to collide with about as many dissociated cells as physical spheroid progenitors, given a density of 50 cell/mm$^2$ (FIG. 9E). This was done by visual inspection of the physical and simulated spheroids. Simulation time could be more accurately estimated by computing the mean time it takes for simulated spheroid progenitors to collide with exactly the number of dissociated cells encountered by the physical spheroid progenitors. |
| 17 | Type of dissociated stem cell | *Xenopus laevis* species embryonic cells (stage 10) | Adhesive voxel singletons. |
| 18 | Number of dissociated cells | ~60,000 | 1000-2000 voxels |
| 19 | Density of dissociated stem cells | 25-150 cells/mm2 | 0.15-0.30 voxels/u$^2$, where u = length of one unstretched voxel. |
| 20 | Distribution of dissociated stem cells | Random distribution without any aggregate clumps. | Uniform distribution within a 81 × 81 × 3 bounding volume, without any initially touching each other or the organisms. |
| 21 | Area covered by dissociated stem cells | No data | 81 × 81 voxel lengths |
| 22 | Stem cell stickiness | Contact adherence | Collision radius of 0.85 voxel lengths. |
| 23 | Stem cell spherification | Adhesion properties lead to a minimized surface area to volume ratio. | Stochastic detachment of chains of voxels within a pile of stem cells; pile force pulling stochastically detached cells inward. |

TABLE 1-continued

The parameters of kinematic self replication in reconfigurable organisms.
Properties of the environment (1-5), reconfigurable organisms (6-16), and
dissociated stem cells (17-26) are grouped under these three categories.

| no. | Parameter | In vivo | In silico |
|---|---|---|---|
| 24 | Size of pile that develops into stable offspring that maintain adherence ~4 d but are not self motile. | Minimum size = 50 cells, ~1.7% of default adult size (50/3000) | When optimizing body shape, a threshold of 108 voxels, 66% the size of default simulated spheroids (161 voxels). Higher threshold set to compensate for other, unknown simulation inaccuracies. When forecasting utility, a threshold of 40 voxels, 25% the size of default simulated spheroids. Forty voxels is the best estimate for the minimum size of piles that developed into self motile offspring in vivo. |
| 25 | Size of pile that develops into stable and mobile offspring that are able to self replicate for 10-14 d. | One fourth the default adult diameter. | Two-thirds and one-fourth for shape optimization and utility forecasting, respectively. |
| 26 | Development time from pile to adult | 4 days | 0.5 seconds of simulation time. |

At the start of each simulation, the simulated dish is seeded with the nine progenitors and 1262 dissociated stem cells. After three seconds of simulation time, the progenitors, and any piles with 108 or fewer voxels, are deleted. Any piles with more than 108 voxels (incipient offspring; FIG. 10E) are then given an additional 0.5 sec to compact and spherify. Empty space in the dish is then replenished with dissociated stem cells. The offspring are matured by adding random cilia forces on their surface voxels (FIG. 10F), after which they are simulated for another three seconds. This process continues until no piles greater than 108 voxels are achieved (FIG. 10G).

Measuring self replication in silico. The self replicative ability of a swarm was taken to be:

$$f = s/p + g, \quad \text{(Eqn. 1)}$$

where g is the total number of filial generations achieved, s is the size of the largest pile, in voxels, at the end of an evaluation period of 3.5 sec (16,366 time steps with step size $2.14 \times 10^{-4}$ sec), and p is the pile size threshold required for a pile to develop into an organism. If s is greater than p, a new filial generation begins, otherwise the simulation terminates. A conservative threshold of p=108, two-thirds the size of the simulated wild type spheroids, was selected such that relatively few randomly generated shapes achieved g >0 (Sect. S2.2). Such overly conservative estimates can compensate for inaccuracies in other simulated parameters.

Statistical hypothesis testing. The diameters of the 10 largest physical offspring (generation 1) built by wild type organisms across five independent trials, and across different cell concentrations (gray points, FIG. 9E), were compared to the diameters of those built by the semitoroidal organisms in three independent trials (pink points, FIG. 9E). The diameters of all offspring were normalized by dividing by the cell concentration at which they were built. Comparing offspring size in this way is a conservative test since the volumetric difference between two spheres is eight times as large as their diametric difference. A Mann-Whitney rank test was performed with a sample of eight independent measurements: the average offspring diameter within the eight independent trials (three trials with progenitor semitoroids, five trials with progenitor spheroids). The null hypothesis is that the average size of the semitoroid's offspring (normalized by cell concentration) was no different than the average size of wild type spheroids' offspring (p=0.037). Controlling for false discovery rate (41), this null hypothesis can be rejected at the 0.05 level of significance (Sect. S4.1).

Wild type organisms produced just a single filial generation in four of the five independent trials. The only trial to produce two generations of offspring was the one with the highest cell concentration tested (150 cells/mm²). The first of three independent trials using the semitoroidal organisms resulted in two filial generations at 61 cells/mm², but was then halted because the organisms all contracted a motily-compromising fungal infection. In the second and third trials using semitoroids, additional precautions were taken to avoid fungal infections. Three successive generations of offspring were produced at 61 cells/mm²; four successive generations of offspring were produced at 91 cells/mm². A Mann-Whitney rank test was performed. The null hypothesis is that the number of generations of self replication achieved by the semitoroids (2 g, 3 g, 4 g) was no greater than the number of generations produced by the wild type spheroids (1 g, 1 g, 1 g, 1 g, 2 g) (p=0.019). Controlling for false discovery rate, the null hypothesis is rejected at the 0.05 level of significance (Sect. S4.2).

A Spearman rank-order correlation coefficient of 0.9322 (p=0.00074) holds between the number of generations achieved and the aggregate size of the 10 largest first generation offspring.

Figure 11:
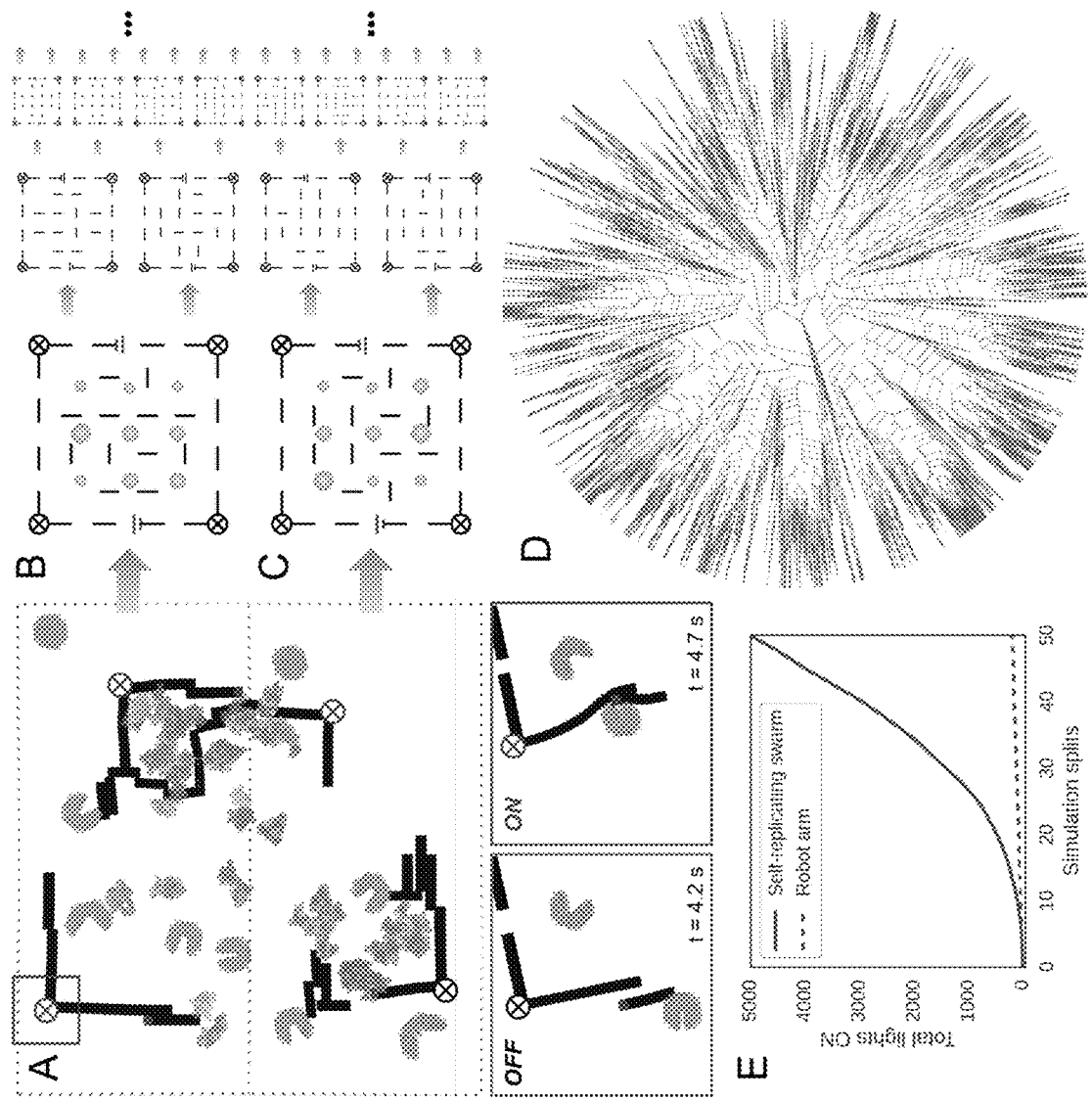
FIG. 11. Forecasting utility. (A) A swarm of self-replicating semitoroidal organisms (grey) was placed inside a partially-completed circuit (black) containing two power sources (red dots), four light emitters (circled X; black when OFF, red when ON), and disconnected flexible adhesive wires (black lines). Dissociated stem cells (not pictured), if pushed into piles, develop into offspring (irregularly shaped gray masses). Dissociated cells are replaced every 3.5 seconds. After 17.5 seconds of self replication and circuit building within a single dish, the progenitors are discarded and all first through fourth filial generation offspring are divided into two equal-sized groups and placed into two new dishes, each containing a partially completed circuit (B,C). If only one offspring is built, one dish is seeded with it. If no offspring are built, bifurcation halts. This process results in an unbalanced binary tree (D). Red edges denote circuits in which at least one light emitter was switched on by closing a circuit from power source to light emitter (OFF/ON inset). Gray edges denote circuits in which no light emitters were switched on. The number of lights switched on increased quadratically with time (E). This differs from k non-replicative robots that can switch lights on in k petri dishes per unit of time, resulting in a line with slope k; for example, a single robot arm could switch on all four lights in its dish at every unit of time (dotted line in E). With sufficient time, the self-replicative swarm can achieve higher utility than the non-replicative swarm for any arbitrarily large value of k.

Forecasting utility. Three kinds of microelectronic components, that adhere permanently upon collision, were added to the simulation: light emitters, batteries, and wire (FIG. 11A). Each component contains vertically stacked and insulated conductors which maintain connectability under translational and rotational movement in plane (FIG. 22C-E). As a side effect of movement, reconfigurable organisms will randomly push together microelectronics modules present in the dish (Sect. S5.1). If a light emitter connects by an unbroken circuit of wire to a battery, the light emitter switches on permanently (as indicated by a red circled X in FIGS. 11 and 22).

The swarm builds piles, which, if large enough, develop into offspring, and the dissociated cells are replenished, every 3.5 seconds. Piles under the size threshold are removed to make way for fresh dissociated cells. Because we are interested in estimating utility rather than self-replication, progenitors are left in the dish and continue building additional offspring alongside their former offspring for another four, 3.5 second periods. After 17.5 seconds of simulation time, the number of light emitters connected to a power supply was recorded, the progenitors were removed, and all offspring were extracted. The offspring were then split equally into two new simulated petri dishes, each with a new partially-completed circuit (Sect. S5.2). Self replication and circuit building begin afresh in these two dishes, again for 17.5 seconds. This is the start of a binary simulation tree (FIG. 11D) in which each simulation begets at most two simulation branches, each containing one half of the produced offspring of their root simulation. If only a single offspring is created by a swarm after 17.5 sec, then only one new simulation branch is started. If no offspring were built, then that branch of the binary simulation tree terminates.

After 50 simulation bifurcations, 5024 light emitters were switched on. Symbolic regression (42) was used to find the degree of a polynomial function that best explains the cumulative number of lights switched on. Regression found that utility increases quadratically with time, as estimates found by symbolic regression all converged toward the quadratic curve derived by ordinary least squares: $2.7x^2-43x+182.4$, where x is the number of simulation bifurcations ($R^2=0.9988$).

REFERENCES AND NOTES FOR EXAMPLE 2

1. Kamm, R. D., Bashir, R., Arora, N., Dar, R. D., Gillette, M. U., Griffith, L. G., Kemp, M. L., Kinlaw, K., Levin, M., Martin, A. C. and McDevitt, T. C. Perspective: The promise of multi-cellular engineered living systems. *APL Bioengineering*, 2, 040901 (2018).
2. Garreta, E., Kamm, R. D., de Sousa Lopes, S. M. C., Lancaster, M. A., Weiss, R., Trepat, X., Hyun, I. and Montserrat, N. Rethinking organoid technology through bioengineering. *Nature Materials*, 20, 145-155 (2021).
3. Huh, D., Matthews, B. D., Mammoto, A., Montoya-Zavala, M., Hsin, H. Y. and Ingber, D. E. Reconstituting organ-level lung functions on a chip. *Science* 328, 1662-1668 (2010).
4. Wu, Q., Liu, J., Wang, X., Feng, L., Wu, J., Zhu, X., Wen, W. and Gong, X. Organ-on-a-chip: Recent breakthroughs and future prospects. *Biomedical Engineering Online*, 19, 1-19 (2020).
5. Losner, J., Courtemanche, K. & Whited, J. L. A cross-species analysis of systemic mediators of repair and complex tissue regeneration. *npj Regen Med* 6, 21 (2021).
6. Hussey, G. S., Dziki, J. L. and Badylak, S. F. Extracellular matrix-based materials for regenerative medicine. *Nature Reviews Materials*, 3, 159-173 (2018).
7. Han, Y., Li, X., Zhang, Y., Han, Y., Chang, F. and Ding, J. Mesenchymal stem cells for regenerative medicine. *Cells*, 8, 886 (2019).
8. Gilbert, S. F., Sarkar, S. Embracing complexity: organism for the 21st century. *Developmental Dynamics*, 219, 1-9 (2000).
9. Blackiston, D., Lederer, E., Kriegman, S., Garnier, S., Bongard, J., Levin, M. A cellular platform for the development of synthetic living machines. *Science Robotics* 6, eabf1571 (2021).
10. Kriegman, S., Blackiston, D., Levin, M., Bongard, J. A scalable pipeline for designing reconfigurable organisms. *Proceedings of the National Academy of Sciences* 117, 1853-1859 (2020).
11. Jones, E. A., & Woodland, H. R. Development of the ectoderm in *Xenopus*: tissue specification and the role of cell association and division. *Cell*, 44, 345-355 (1986).
12. Kim, H. Y., Jackson, T. R., Stuckenholz, C., Davidson, L. A. Tissue mechanics drives regeneration of a mucociliated epidermis on the surface of *Xenopus* embryonic aggregates. *Nature Communications*, 11, 1-10 (2020).
13. Walentek, P. Manipulating and analyzing cell type composition of the *Xenopus* mucociliary epidermis. *Xenopus*, 251-263 (2018). Humana Press, New York, N.Y.
14. Stubbs, J. L., Davidson, L., Keller, R., Kintner, C. Radial intercalation of ciliated cells during *Xenopus* skin development. *Development*, 133, 2507-2515 (2006).
15. von Neumann, J. Theory of self-reproducing automata, Ed. Burks, A. W., *University of Illinois Press* (1966).
16. Ray, T. S., Evolution, complexity, entropy and artificial reality. *Physica D: Nonlinear Phenomena*, 75, 239-263 (1994).
17. Chou, H. H. and Reggia, J. A. Emergence of self-replicating structures in a cellular automata space. *Physica D: Nonlinear Phenomena*, 110, 252-276 (1997).
18. Studer, G. and Lipson, H. Spontaneous emergence of self-replicating structures in molecube automata. In Proc. of *the 10th Int. Conf on the Simulation and Synthesis of Living Systems*, 227-233 (2006).
19. Penrose, L. S. Self-reproducing machines. *Scientific American*, 200, 105-117 (1959).
20. Jacobson, H. On models of reproduction. *American Scientist*, 46, 255-284 (1958).
21. Chirikjian, G. S., Zhou, Y., Suthakorn, J. Self-replicating robots for lunar development. *IEEE Transactions on Mechatronics* 7, 462-472 (2002).
22. Zykov, V., Mytilinaios, E., Adams, B., Lipson, H. Self-reproducing machines. *Nature* 435, 163-164 (2005).
23. Griffith, S., Goldwater, D. & Jacobson, J. Self-replication from random parts. *Nature*, 437, 636 (2005).
24. Adams, B. and Lipson, H. A universal framework for analysis of self-replication phenomena. *Entropy*, 11, 295-325 (2009).
25. Chirikjian, G. S. Parts entropy and the principal kinematic formula. In Procs. of *the IEEE Intl. Conf. on Automation Science and Engineering*, 864-869 (2008). 10.1109/COASE.2008.4626465
26. Qu, Zhe, et al. Towards high-performance microscale batteries: Configurations and optimization of electrode materials by in-situ analytical platforms. *Energy Storage Materials*, 29, 17-41 (2020).
27. Kim, Y., Kim, H., Cho, Y. et al. Bright visible light emission from graphene. *Nature Nanotech* 10, 676-681 (2015).
28. Gao, W., Ota, H., Kiriya, D., Takei, K., & Javey, A. Flexible electronics toward wearable sensing. *Accounts of Chemical Research*, 52, 523-533 (2019).
29. Ricotti, L., Trimmer, B., Feinberg, A. W., Raman, R., Parker, K. K., Bashir, R., Sitti, M., Martel, S., Dario, P. and Menciassi, A. Biohybrid actuators for robotics: A review of devices actuated by living cells. *Science Robotics*, 2, eaaq0495 (2017).

30. Park, S. J., Gazzola, M., Park, K. S., Park, S., Di Santo, V., Blevins, E. L., Lind, J. U., Campbell, P. H., Dauth, S., Capulli, A. K. and Pasqualini, F. S., Phototactic guidance of a tissue-engineered soft-robotic ray. *Science* 353, 158-162 (2016)
31. Maury, C. P. J. Amyloid and the origin of life: self-replicating catalytic amyloids as prebiotic informational and protometabolic entities. *Cellular and Molecular Life Sciences*, 75, 1499-1507 (2018).
32. Tank, E. M., Harris, D. A., Desai, A. A., & True, H. L. Prion protein repeat expansion results in increased aggregation and reveals phenotypic variability. *Molecular and Cellular Biology*, 27, 5445-5455 (2007).
33. Boer, M. M., de Dios, V. R. and Bradstock, R. A. Unprecedented burn area of Australian mega forest fires. *Nature Climate Change*, 10, 171-172 (2020).
34. Emanuel, K. Increasing destructiveness of tropical cyclones over the past 30 years. *Nature*, 436, 686-688 (2005).
35. Lin, N., Kopp, R. E., Horton, B. P. and Donnelly, J. P. Hurricane Sandy's flood frequency increasing from year 1800 to 2100. *Proceedings of the National Academy of Sciences*, 113, 12071-12075 (2016).
36. Liu, Y. Y., Slotine, J. J. and Barabási, A. L. Controllability of complex networks. *Nature*, 473, 167-173 (2011).
37. Nieuwkoop, P. D., & Faber, J. Normal table of. *Xenopus laevis*, 252 (1994).
38. Schmidt, M., Lipson, H. Age-fitness pareto optimization. *Genetic Programming Theory and Practice VIII*, 129-146 (2011).
39. Stanley, K. O. Compositional pattern producing networks: a novel abstraction of development. *Genetic programming and evolvable machines* 8, 131-162 (2007).
40. Hiller, J. and Lipson, H. Dynamic simulation of soft multimaterial 3D-printed objects. *Soft Robotics*, 1, 88-101 (2014).
41. Benjamini, Y., Hochberg, Y. Controlling the false discovery rate: A practical and powerful approach to multiple testing. *Journal of the Royal Statistical Society: Series B (Methodological)*, 57, 289-300 (1995).
42. Schmidt, M., Lipson, H. Distilling free-form natural laws from experimental data. *Science*, 324, 81-85 (2009).

Example 3—Supplemental Material for Example 2

Materials and Methods

1. Summary of Previous Work Using Reconfigurable Organisms.

The first manuscript to report reconfigurable organisms (10) introduced a pipeline for automatically designing cardiac-driven organisms to exhibit a desired behavior, such as locomotion. The overall geometry of each organism, and its internal configuration of ectoderm and cardiac muscle, were designed ab initio using an evolutionary algorithm and physics-based simulation. The most promising designs were manufactured by combining cells, according to the computer-generated blueprint, and shaping the resultant aggregates with a microcautery electrode and surgical forceps.

Later (9), it was demonstrated that multiciliated epithelial tissue could be used, instead of cardiac muscle, to generate cilia-driven "swimming" designs. These ciliated designs can be manufactured more rapidly and have a higher probability of self motile behavior than the cardiac-driven designs. Ciliated reconfigurable organisms can be produced two different ways. The excised animal cap tissue, including the outer superficial ectodermal layer, can be left intact and allowed to heal into mucociliary epidermal spheroids (FIG. 12A,B). Alternatively, if dissociated stem cells from one or more animal caps are brought into contact, they will adhere, compact and reassemble into a mucociliary spheroid (FIG. 12C,D). Using either construction method, the resultant aggregates are structurally and functionally equivalent (8). We here refer to these motile spheres as wild type reconfigurable organisms.

*Xenopus* tissue is ideal for this use case because its cell types and organization are known (43-51) and their development is controllable: cells can be driven to any lineage (52-61) and specific cell types can be inhibited or overproduced with molecular or chemical intervention (62-66). However, outside of (9) and (10), these tissues have not been used as self-motile agents, nor have they been engineered to exhibit specific motile functions such as particle aggregation. In (9), the useful lifespan, velocities, and movements of cilia-driven behavior was quantified as these metrics were not previously reported. These data were used to develop the simulations used in the present work, which builds on both studies to show how ciliated tissues can be shaped to control their collective behavior and amplify their kinematic self replication.

2. The Simulation.

This section details how self-replication was simulated. The corresponding Table 1 details how simulation parameters were estimated from biology.

2.1. Biophysics in Silico.

Voxel-based physics. Biological tissues were modeled as collections of elastic voxels (deformable cuboids) (9,10). Two voxels in the same simulation can connect face to face on a 3D cartesian grid by a single Euler-Bernoulli beam, forming a small body. A beam starts at the center point mass of one voxel and ends at the center of the other voxel. Beams have rotational and translational stiffness allowing for local stretching, compressing, bending, and twisting of one voxel mass relative to another.

Simulated organisms comprise hundreds of voxels. Each voxel within an organism is connected by beams to at most six other voxels, one on each of its six faces (up, down, left, right, front, back). Voxels with less than six beams thus have at least one face that is exposed, forming one part of the external surface of the organism's body (or part of the surface of an internal cavity). Self-collisions between two non-neighboring surface voxels are resolved by temporary beams that are created when two unconnected surface voxels penetrate each other, and are removed after the voxels are pushed far enough apart so that they no longer intersect.

The hydrodynamics of the aqueous medium in which the organisms operate is modeled by a resisting viscous force that damps out inertial effects. Neither laminar nor turbulent flows were simulated. Interactions between voxels and the bottom of the petri dish are modeled as Hookean springs (translational stiffness only), which add an upward force opposing penetration of a surface plane, which is located at $z=0$ and extends infinitely in the horizontal (x,y) plane. For more details about the underlying physics model, see (40).

GPU acceleration. To simulate the swarms of colliding organisms and dissociated stem cells reported in the present work, we used voxcraft-sim (67), a GPU-accelerated re-implementation of Voxelyze (the physical simulator underpinning VoxCAD (40)) with a more scalable tree-based collision system (68). In Voxelyze, voxels are evaluated sequentially on a single thread of a CPU. In voxcraft-sim, thousands of voxels can be evaluated concurrently on a GPU (FIG. 16). Collisions in Voxelyze are detected and resolved in an exhaustive pairwise comparison of all n surface voxels, with time complexity O(n2). In voxcraft-sim, collisions are handled using a bounding volume hierarchy (BVH) tree data structure with O(n log n).

Organisms (ciliated, pink voxels). The mature swimming organisms, which are composed of thousands of living cells, are simulated by hundreds of pink colored voxels (FIGS. 8A, 9F-H, 15). Each pink voxel thus approximates a section of tissue, rather than a one-to-one voxel-to-cell representation. The aggregate (metachronal wave) force produced by a patch of beating cilia was modeled on each surface voxel as an impulse force originating at the center of the voxel and pointing in any direction in the horizontal (x,y) plane. The vertical (z) moments and forces of a simulated organism's pink voxels are locked in plane to stabilize their movement and remove the possibility of persistent tumbling behavior in silico. Tumbling sometimes does briefly occur in wild type reconfigurable organisms, but they tend to glide with a constant dorsoventral orientation.

Dissociated stem cells (adhesive, green voxels). Dissociated stem cells are simulated as dissociated (beamless) voxel singletons and are colored green. When two green voxels collide with each other, a new semi-permanent beam is created to bond them together. The beam is semi-permanent because it is breakable under conditions that are described below. Green voxels do not have cilia and, unlike pink voxels of the mature organisms, green voxels are free to move and rotate vertically as well as horizontally when hit. In an earlier draft of the model, we simulated dissociated stem cells with negative buoyancy so that they would settle to the bottom of the dish, as observed in vivo. However, simulated adhesion under negative buoyancy almost always resulted in flat planes of voxels connected along the surface plane at the bottom of the dish. The model was therefore adjusted so that stem cells were simulated with neutral buoyancy. That is, without collision forces impinging on the green adhesive voxels, they will remain suspended in place. This enabled 3D adhesion because floating voxels are free to rotate out of plane as they bond to other floating voxels and aggregations of voxels.

When dissociated stem cells come together and touch in vivo they naturally compact and form spheres as their adhesion properties lead to a minimized surface-area-to-volume ratio. Because our model initially did not capture this spherical bias, green voxels would often connect distally, forming long chains of voxels, which were not observed in vivo. To simulate in vivo compaction and spherification, piles of connected green voxels are continually compressed together by stochastically detaching the semi-permanent beams of surface voxels that have two or fewer neighbors. When detached from a pile, voxels are immediately pushed toward a different, randomly selected spot along the pile's surface to be reattached upon collision with a new semi-permanent (but breakable) bond. Additional damping was applied to the movement of green voxels to ensure that detached voxels remained within the local neighborhood of a pile.

Petri dish. The depth of the aqueous solution, and its lateral limits (the walls of the dish), were modeled by soft boundaries that repel voxels that penetrate predefined bounds (in the main experiments, a 81 voxel wide, 81 voxel long, 5 voxel high volume) with an opposite force 1 proportional to the squared penetration. A hard boundary, such as the surface plane used to model the bottom of the dish, or an upright plane of immovable voxels, could also be used to simulate a wall of a petri dish. However, using fixed voxels for walls has two issues. First, any additional voxels in the simulation require tracking additional collisions which can become computationally expensive. Additionally, the time step of numerical integration must be lowered to prevent simulation instabilities caused by laterally swimming organisms pressing themselves, and piles of simulated stem cells, against a wall of voxels and penetrating it. This can cause the organism or stem cell pile to become permanently bolted to the wall. Finally, we found that hard boundaries, even when computationally stable, biased the random movement of the organisms to remain pressed along the walls of a dish for long intervals of simulation time. While this prediction of wall following was borne out in vivo, exhausting a fixed computational budget to collect isolated behavioral data can be wasteful for the purposes of learning to control interactions between organisms and dissociated cells. To reduce the amount of simulation time required to observe piling behavior occurring in silico, elastic boundaries were implemented which nudge the organisms back toward the dissociated stem cells in the center of the dish.

Hyperparameters. Parameters of the model were estimated from biology according to Table 1. Both the mature organisms' tissue (pink voxels) and the dissociated stem cells (green voxels) were simulated with Young's modulus of 0.05 MPa, density 1000 kg/m^3, and 0.5 Poisson's ratio. These material properties of the voxels were manually adjusted for simulation speed. (Heavier/softer material can be stably simulated with a larger time step of numerical integration because their resonance frequency is lower than light/stiff material.) These properties were kept constant across the two material types to minimize instantaneous changes in dynamics when piles of stem cells develop into ciliated organisms. The development of adhesive, compacting stem cells into the mature tissue of a swimming organism is detailed in the following section.

2.2. Self Replication in Silico.

Filial generations. A swarm of N parent organisms (ciliated pink voxels) were placed amid a uniform lattice of suspended dissociated stem cells (adhesive green voxels). These initial N parents are here referred to as filial generation zero (F0). In the main experiments, there are nine simulated F0 organisms (N=9).

Each filial generation, parents swam for three seconds with random cilia impulse forces, where the x,y cilia force for each surface voxel, in Newtons, was drawn from a bivariate uniform distribution from (−0.3, −0.3) to (0.3, 0.3). These cilia forces are held constant, relative to the orientation of the voxel, for one second of simulation time (4676 time steps), yielding ballistic swimming trajectories. After every second of simulation time, all of the cilia forces were replaced by new random values, resulting in three independent random trajectories of collective swimming behavior. As simulated parents swim along the surface of the dish, they collide with the simulated dissociated stem cells, which adhere into piles of stem cells that slowly compact together. At the end of their three second evaluation period, parents were removed from the simulation and the piles were allowed to compact and spherify for an additional 0.5 seconds of 2 simulation time.

Figure 15:
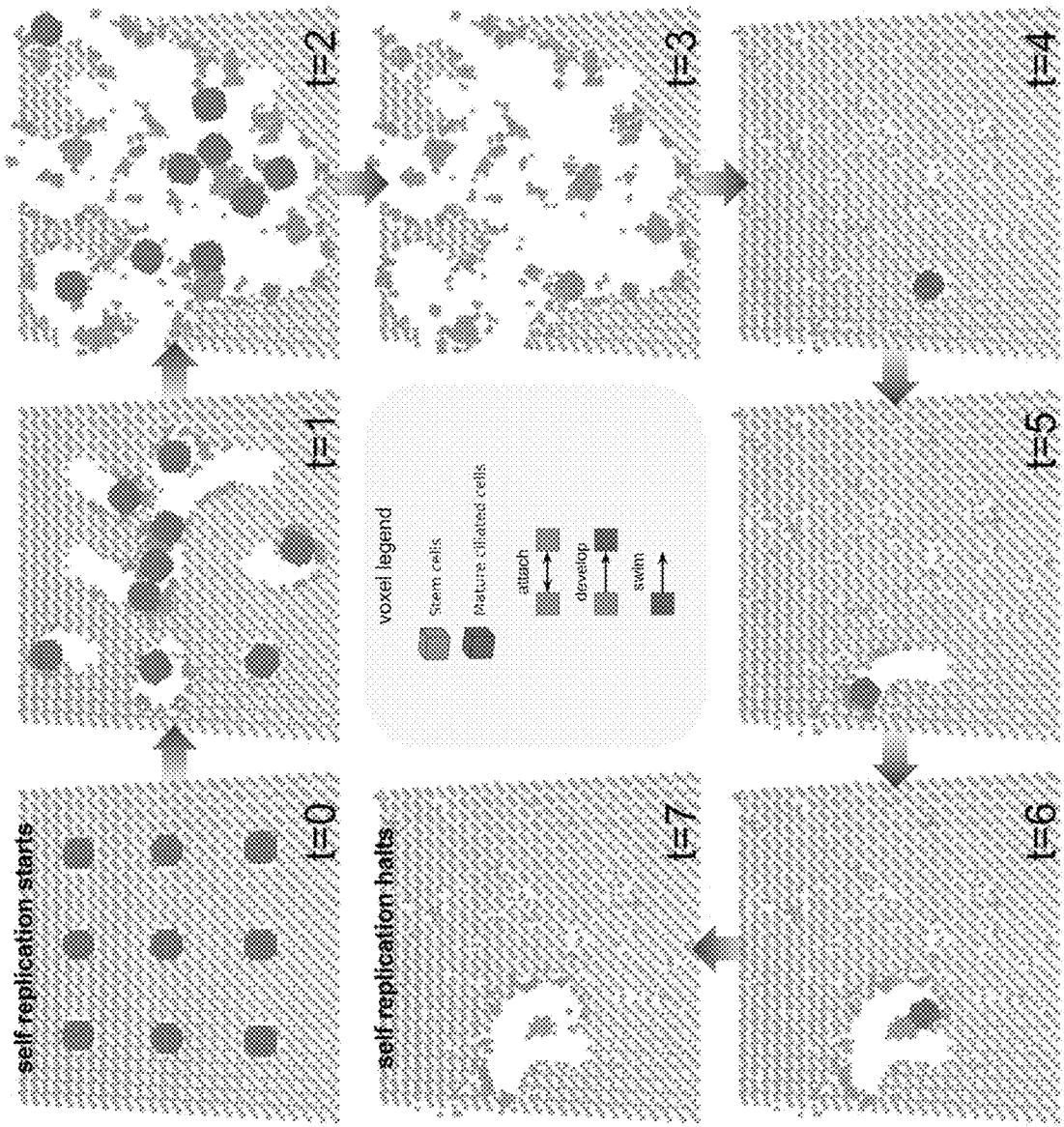
FIG. 15. Modeling kinematic self replication. [Clockwise from top left:] A swarm of nine virtual wild type spheroids (parents; pink) are placed in a virtual petri dish that is lined with virtual dissociated stem cells (green). As the swarm moves through the dissociated stem cells, piles of stem cells are formed (t=2). The parents are then removed (t=3), and any piles larger than a preselected threshold, develop from piles to motile offspring (green to pink) (t=4). More dissociated cells are injected into empty space in the dish, and pile building restarts. Here, a single filial generation was produced, then replication stopped (t=7). On average, simulated wild type spheroids did not produce piles larger than the selected threshold of two thirds the size of a wild type spheroid. This threshold was set higher than the biological data suggested: piles approximately one fifth the diameter of the initial parents could develop into motile offspring. However, small children are likely to produce even smaller grandchildren, or none at all. Because each filial generation is computationally expensive, we increased the threshold to create a more conservative filter: only the settings that result in the largest offspring and the most replication will pass through the filter and be allotted computational resources.

The size of the largest pile was then compared against a threshold of 108 voxels, two-thirds the size of the unsculpted, 161-voxel F0 spheres. Piles smaller than the threshold (less than 108 voxels) were removed from simulation, and piles larger than the threshold (if any) develop instantaneously into child organisms with cilia (green voxels become pink voxels) (FIG. 15). This first set of organisms assembled by the F0 parents are referred to as the first filial generation (F1). Empty space in the dish surrounding the F1 organisms (due to the removal of parents and small piles below the threshold) is repopulated by a fresh grid of dissociated stem cells, and a new 3.5 second evaluation period begins in which the F1 organisms are the pile-building parents.

The F1 organisms may build piles, the largest of which may develop into F2 organisms, which in turn may build piles of their own, and so on. The simulation ends when no parents (pink voxels) remain in the dish, or after a maximum of five filial generations (F5) elapse, for at most 6*3.5=21 seconds.

Figure 12:
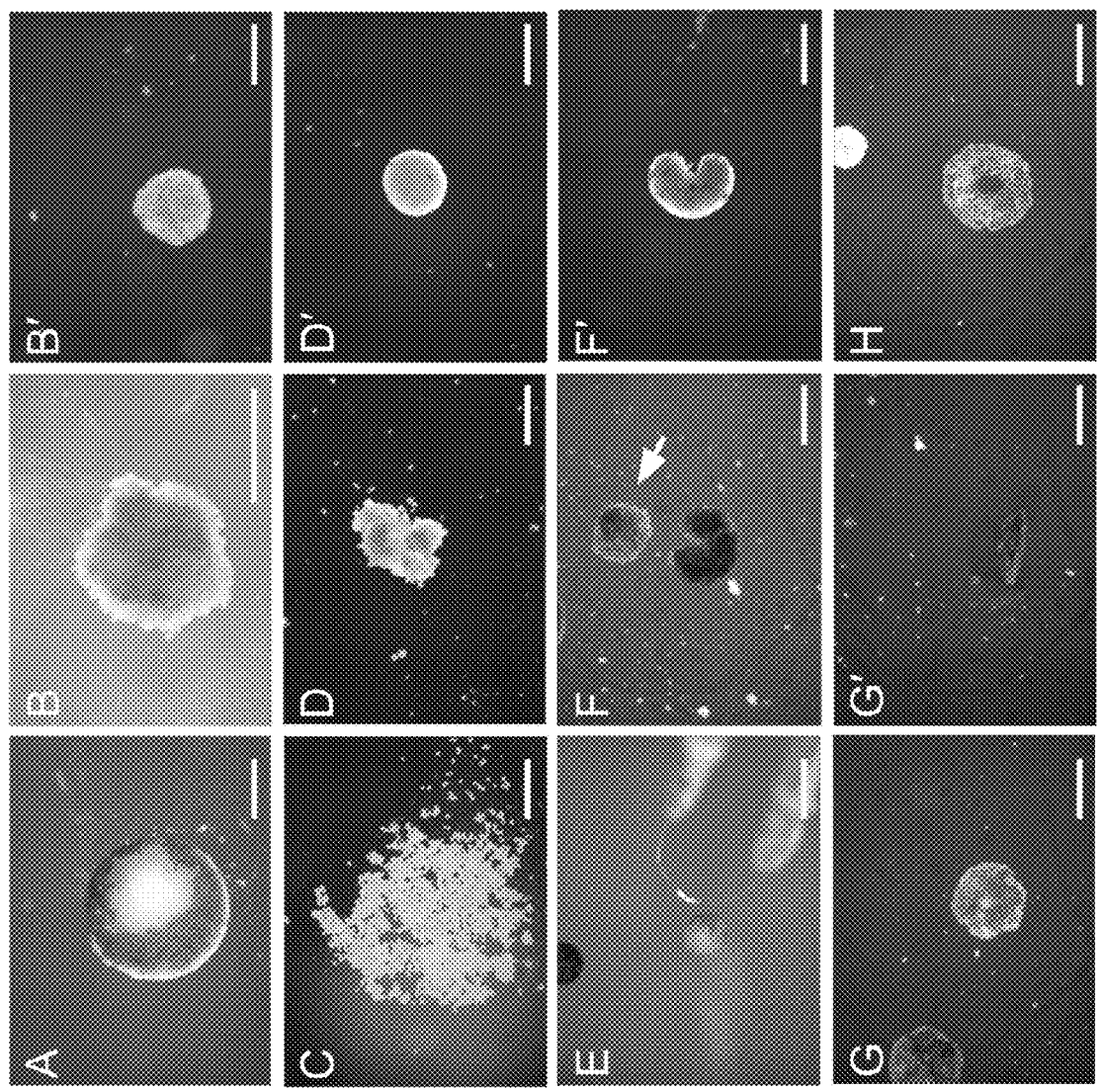
FIG. 12. Construction of reconfigurable organisms from embryonic *Xenopus* material. Two methods are used to construct the initial swarm (generation 0) of reconfigurable organisms. The first requires excision of animal cap tissue of Nieuwkoop and Faber stage 10 embryos (24 h post fertilization at 14° C.) with microsurgery forceps (A). Individual explants are then transferred to a 0.75× saline solution (Marc's Modified Ringer's) which allows the tissue to heal into a spheroid of tissue (B) and develops into a mucociliary epithelium, becoming motile after 3-4 days of culture at 14° C. (B'). The second method dissociates the animal cap material in calcium free, magnesium free media, and the pigmented superficial ectoderm is discarded (C). The dissociated cells are then transferred to 0.75×MMR and mechanically pushed into a pile, which naturally adheres (D). The aggregates forms into a spheroid of tissue (D') which becomes motile after 3-4 days of culture at 14° C. Various morphologies can be given to parent organisms via surgical forceps and a microcautery electrode (E), allowing for the production of semi-toroidal shapes [shown in F, next to a spheroid (white arrow head in F) and shaped from reaggregated cells in F' ], moderately compressed spheroids (G, lateral view G'), and toroids (H). Scale bars indicate 500 microns.
Figure 14:
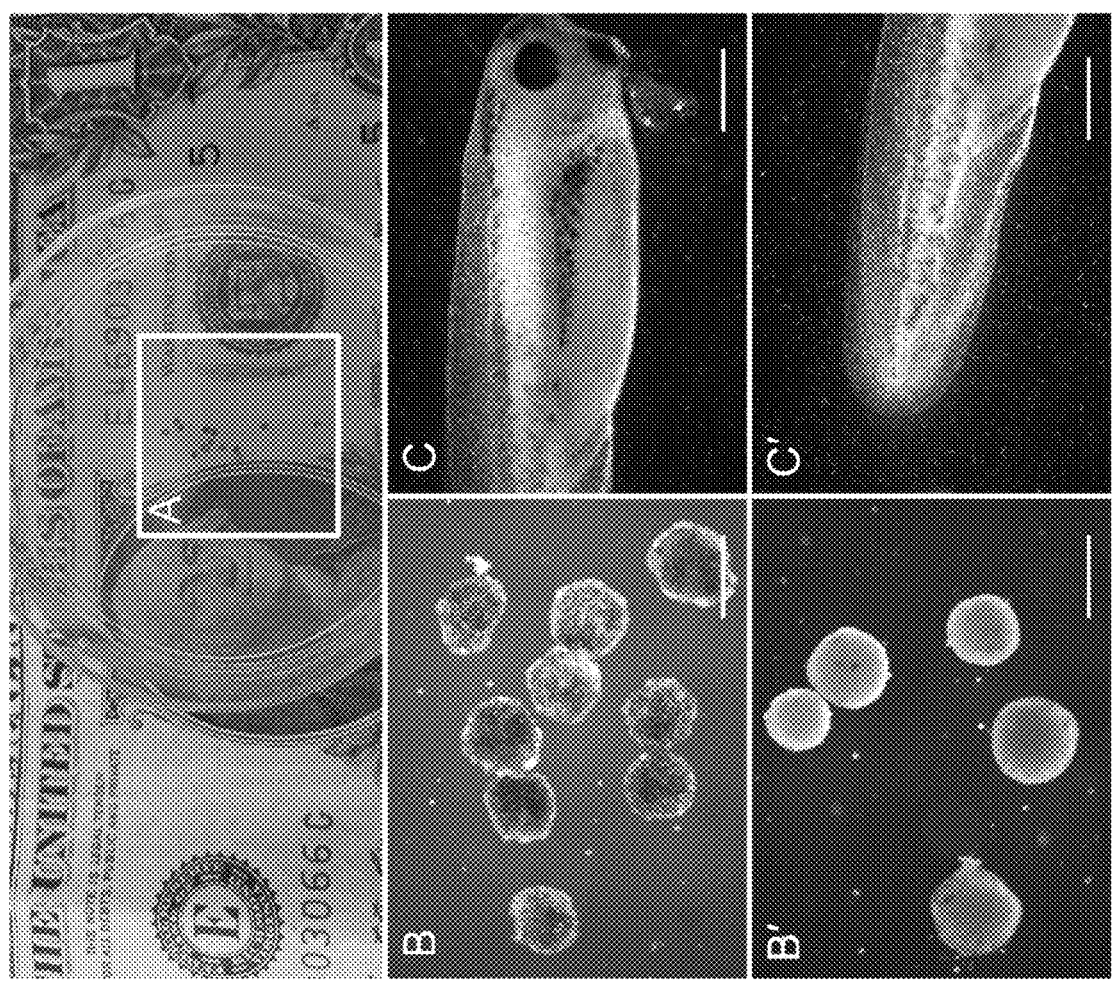
FIG. 14. Relative size of the self-replicating organisms. (A) It can be difficult to conceptualize 500 microns, so C- and O shaped designs were placed on top of a US dollar bill for comparison. Wild type reconfigurable organisms healed from an animal cap (B), and reconfigurable organisms formed by manually dissociating and reassociating the stem cells contained within a cap (B'), are shown at the same magnification beside a tadpole (C,C'), also at the same magnification: Scale bars indicate 500 microns.

Hyperparameters. The behavior of each filial generation was simulated for 16,366 time steps (just long enough to see pile-making behavior occur), with step size $2.14 \times 10^{-4}$ sec (just low enough to ensure simulation stability; for details see (40)), yielding an evaluation period of 3.5 simulation seconds. Table 1 details how these simulated dynamics correspond to properties of the physical self-replicating system, in vivo. 3. The AI design tools. This section describes how parameters of reconfigurable organisms, and their environment, can be adjusted to generate a desired amount of kinematic self replication in reconfigurable organisms. 3.1. Controllability of reconfigurable organisms. Individual behavior. Previous work (10) used an evolutionary algorithm to automatically design the overall shape, and distributions of epidermal and cardiac tissues, of deciliated reconfigurable organisms, so that they would exhibit some desired behavior such as surface-based locomotion in a specified direction. Behavior generated in simulation was observed in some of the manufactured organisms because cardiac-driven movement was sufficiently determined by geometry and tissue distribution. The behavior of the cilia-driven swimming organisms manufactured here, in contrast, are not as obviously determined by their geometry: very similarly shaped bodies can move very differently. Even a single organism can exhibit diverse movement patterns driven by spontaneous transitions in cilia beating patterns, rather than traveling along a single trajectory as when driven by a regular cardiac pulse. Collective Behavior. Predicting cilia-driven movement of an individual organism is challenging. But some collective behaviors do appear to be predictable in simulation. Specifically, it was found that when a swarm of ciliated reconfigurable organisms are placed together in the same dish amid debris [carmine dye particles (10) or silicone coated iron oxide beads (9)], they tend to reliably aggregate the initially scattered debris into piles. Previous modeling studies (9) assessed whether body shape could affect pile size in silico under precisely tuned movement trajectories (a custom set of static cilia forces was optimized for each swarm to increase pile size). The data suggested that some body shapes were capable of building significantly larger piles than others, but this hypothesis was not verified in vivo. And because the simulated debris were intended to model synthetic material, piles of debris did not develop into child organisms. In previous implementations of dynamic voxel attachment, piles were only numerically stable if inertial forces were heavily overdamped post-attachment, resulting in heavy, irregularly-shaped masses of tangled voxels that could not stably locomote using cilia impulse forces. The "debris" in this present work, instead, are dissociated stem cells that, when pushed together into a sufficiently large pile, compact and develop into a ciliated organism (offspring) capable of swimming and pushing together loose stem cells into additional piles (which can then develop into yet additional offspring). The control problem is thus to adjust the amount of self replication produced by the swarm without knowing exactly how the individual organisms will move. 3.2. Increasing the amount of self replication. There are various adjustable parameters of the self reproducing system that can be manually tuned or tuned by an evolutionary algorithm (Table 1) to affect the amount of self replication. Some of these conditions are strict and non-adjustable. Contamination, for instance, must be avoided or viability will be lost between rounds of replication. Likewise, a suitable temperature range for frog embryos and ex vivo tissues/cells must be maintained in vitro (4° C. to 28° C.). Other conditions are more adjustable. For instance, the size of the petri dish and the number of organisms could be changed. The size of the manually constructed organisms are all 400-600 microns in diameter (FIG. 14), but can be made larger or smaller (FIG. 12). The adherence properties of the dissociated stem cells could be altered through the expression of cadherins or integrins. Reconfigurable organisms live for 10 to 14 days from the energy preloaded in their cells; but they can survive for at least three months in a nutrient rich medium (9). The speed at which the organisms can move during their lifetimes can be throttled by increasing or decreasing the viscosity of their aqueous environment and the friction of the arena substrate. The structure of the bottom surface or walls of the dish can channel and/or constrain the otherwise unpredictable movement of cilia-driven reconfigurable organisms (9). Finally, the morphology of the organisms can affect how they interact with other objects and with each other (9,10). This inherent sensitivity of kinematic self replication to adjustable external conditions exposes several potential control parameters that can be set by a human operator or automatic control system. Here, we focus on two such parameters: the shape of the organisms and the structure of the terrain on which they operate. Body shape. The initial swarm of reconfigurable organisms (F0), which are formed by manually deconstructing one-day old *Xenopus* embryos, naturally compact into spheroids due to cell adherence (referred to here as "wild type"), but they can be carved into other shapes by subtraction (FIG. 12F,H). The wild type F0 spheroids are here modeled as a vertical stack of five circular layers of 21, 37, 45, 37, and 21 voxels, respectively, yielding a voxelized spheroid composed of 161 voxels with a 7:5 width:height aspect ratio (FIG. 15). Other body shapes can be formed by removing one or more of the 161 voxels in a single simulated spheroid. For simplicity, each of the N organisms within a swarm were constrained to share the same body shape. Terrain (black voxels). The terrain of a simulated petri dish can be modified by adding fixed structures along the bottom surface of the dish, in the form of black voxels. Because the simulated organisms cannot move over or through the fixed structures, the terrain can channel the random movement of the organisms along more predictable trajectories within predefined limits. Details of the two experiments modifying body shape and terrain, respectively, are identical unless stated otherwise. Encoding shape. A structure made of voxels (whether body shape or terrain) can be encoded as a network that takes as input a set of regularly-spaced coordinates within a bounding volume of fixed size, and outputs whether or not a voxel is present at each of those required to observe piling behavior occurring in silico, elastic boundaries were implemented which nudge the organisms back toward the dissociated stem cells in the center of the dish. Hyperparameters. Parameters of the model were estimated from biology according to Table 1. Both the mature organisms' tissue (pink voxels) and the dissociated stem cells (green voxels) were simulated with Young's modulus of 0.05 MPa, density 1000 kg/m^3, and 0.5 Poisson's ratio. These material properties of the voxels were manually adjusted for simulation speed. (Heavier/softer material can be stably simulated with a larger time step of numerical integration because their resonance frequency is lower than light/stiff material.) These properties were kept constant across the two material types to minimize instantaneous changes in dynamics when piles of stem cells develop into ciliated organisms. The development of adhesive, compacting stem cells into the mature tissue of a swimming organism is detailed in the following section. 2.2. Self replication in silico. Filial generations. A swarm of N parent organisms (ciliated pink voxels) were placed amid a uniform lattice of suspended dissociated stem cells (adhesive green voxels). These initial N parents are here referred to as filial generation zero (F0). In the main experiments, there are nine simulated F0 organisms (N=9). Each filial generation, parents swam for three seconds with random cilia impulse forces, where the x,y cilia force for each surface voxel, in Newtons, was drawn from a bivariate uniform distribution from (−0.3, −0.3) to (0.3, 0.3). These cilia forces are held constant, relative to the orientation of the voxel, for one second of simulation time (4676 time steps), yielding ballistic swimming trajectories. After every second of simulation time, all of the cilia forces were replaced by new random values, resulting in three independent random trajectories of collective swimming behavior. As simulated parents swim along the surface of the dish, they collide with the simulated dissociated stem cells, which adhere into piles of stem cells that slowly compact together. At the end of their three second evaluation period, parents were removed from the simulation and the piles were allowed to compact and spherify for an additional 0.5 seconds of 2 simulation time. The size of the largest pile was then compared against a threshold of 108 voxels, two-thirds the size of the unsculpted, 161-voxel F0 spheres. Piles smaller than the threshold (less than 108 voxels) were removed from simulation, and piles larger than the threshold (if any) develop instantaneously into child organisms with cilia (green voxels become pink voxels) (FIG. 15). This first set of organisms assembled by the F0 parents are referred to as the first filial generation (F1). Empty space in the dish surrounding the F1 organisms (due to the removal of parents and small piles below the threshold) is repopulated by a fresh grid of dissociated stem cells, and a new 3.5 second evaluation period begins in which the F1 organisms are the pile-building parents. The F1 organisms may build piles, the largest of which may develop into F2 organisms, which in turn may build piles of their own, and so on. The simulation ends when no parents (pink voxels) remain in the dish, or after a maximum of five filial generations (F5) elapse, for at most 6*3.5=21 seconds.

Hyperparameters. The behavior of each filial generation was simulated for 16,366 time steps (just long enough to see pile-making behavior occur), with step size 2.14×10−4 sec (just low enough to ensure simulation stability; for details see (40)), yielding an evaluation period of 3.5 simulation seconds. Table 1 details how these simulated dynamics correspond to properties of the physical self-replicating system, in vivo.

3. The AI Design Tools.

This section describes how parameters of reconfigurable organisms, and their environment, can be adjusted to generate a desired amount of kinematic self replication in reconfigurable organisms.

3.1. Controllability of Reconfigurable Organisms.

Individual behavior. Previous work (10) used an evolutionary algorithm to automatically design the overall shape, and distributions of epidermal and cardiac tissues, of decili-ated reconfigurable organisms, so that they would exhibit some desired behavior such as surface-based locomotion in a specified direction. Behavior generated in simulation was observed in some of the manufactured organisms because cardiac-driven movement was sufficiently determined by geometry and tissue distribution. The behavior of the cilia-driven swimming organisms manufactured here, in contrast, are not as obviously determined by their geometry: very similarly shaped bodies can move very differently. Even a single organism can exhibit diverse movement patterns driven by spontaneous transitions in cilia beating patterns, rather than traveling along a single trajectory as when driven by a regular cardiac pulse.

Collective Behavior. Predicting cilia-driven movement of an individual organism is challenging. But some collective behaviors do appear to be predictable in simulation. Specifically, it was found that when a swarm of ciliated reconfigurable organisms are placed together in the same dish amid debris [carmine dye particles (10) or silicone coated iron oxide beads (9)], they tend to reliably aggregate the initially scattered debris into piles. Previous modeling studies (9) assessed whether body shape could affect pile size in silico under precisely tuned movement trajectories (a custom set of static cilia forces was optimized for each swarm to increase pile size). The data suggested that some body shapes were capable of building significantly larger piles than others, but this hypothesis was not verified in vivo. And because the simulated debris were intended to model synthetic material, piles of debris did not develop into child organisms. In previous implementations of dynamic voxel attachment, piles were only numerically stable if inertial forces were heavily overdamped post-attachment, resulting in heavy, irregularly-shaped masses of tangled voxels that could not stably locomote using cilia impulse forces.

The "debris" in this present work, instead, are dissociated stem cells that, when pushed together into a sufficiently large pile, compact and develop into a ciliated organism (offspring) capable of swimming and pushing together loose stem cells into additional piles (which can then develop into yet additional offspring). The control problem is thus to adjust the amount of self replication produced by the swarm without knowing exactly how the individual organisms will move.

3.2. Increasing the Amount of Self Replication.

There are various adjustable parameters of the self reproducing system that can be manually tuned or tuned by an evolutionary algorithm (Table 1) to affect the amount of self replication. Some of these conditions are strict and non-adjustable. Contamination, for instance, must be avoided or viability will be lost between rounds of replication. Likewise, a suitable temperature range for frog embryos and ex vivo tissues/cells must be maintained in vitro (4° C. to 28° C.). Other conditions are more adjustable. For instance, the size of the petri dish and the number of organisms could be changed. The size of the manually constructed organisms are all 400-600 microns in diameter (FIG. 14), but can be made larger or smaller (FIG. 12). The adherence properties of the dissociated stem cells could be altered through the expression of cadherins or integrins. Reconfigurable organisms live for 10 to 14 days from the energy preloaded in their cells; but they can survive for at least three months in a nutrient rich medium (9). The speed at which the organisms can move during their lifetimes can be throttled by increasing or decreasing the viscosity of their aqueous environment and the friction of the arena substrate. The structure of the bottom surface or walls of the dish can channel and/or constrain the otherwise unpredictable movement of cilia-driven reconfigurable organisms (9). Finally, the morphology of the organisms can affect how they interact with other objects and with each other (9,10). This inherent sensitivity of kinematic self replication to adjustable external conditions exposes several potential control parameters that can be set by a human operator or automatic control system. Here, we focus on two such parameters: the shape of the organisms and the structure of the terrain on which they operate.

Body shape. The initial swarm of reconfigurable organisms (F0), which are formed by manually deconstructing one-day old *Xenopus* embryos, naturally compact into spheroids due to cell adherence (referred to here as "wild type"), but they can be carved into other shapes by subtraction (FIG. 12F,H). The wild type F0 spheroids are here modeled as a vertical stack of five circular layers of 21, 37, 45, 37, and 21 voxels, respectively, yielding a voxelized spheroid composed of 161 voxels with a 7:5 width:height aspect ratio (FIG. 15). Other body shapes can be formed by removing one or more of the 161 voxels in a single simulated spheroid. For simplicity, each of the N organisms within a swarm were constrained to share the same body shape.

Terrain (black voxels). The terrain of a simulated petri dish can be modified by adding fixed structures along the bottom surface of the dish, in the form of black voxels. Because the simulated organisms cannot move over or through the fixed structures, the terrain can channel the random movement of the organisms along more predictable trajectories within predefined limits. Details of the two experiments modifying body shape and terrain, respectively, are identical unless stated otherwise.

Encoding shape. A structure made of voxels (whether body shape or terrain) can be encoded as a network that takes as input a set of regularly-spaced coordinates within a bounding volume of fixed size, and outputs whether or not a voxel is present at each of those three-dimensional locations. Consistent with previous computational models of reconfigurable organisms (10), a feedforward Compositional Pattern-Producing Network, or CPPN (39), was used to encode voxel structures. A CPPN consists of vertices connected by weighted edges. Each edge multiplies its input value by a real valued weight between −1 and 1. Each vertex sums the values of its input edges and outputs a function applied to that sum. The function encoded in a node is drawn from the following set: sine, signum, square, absolute value, square root of the absolute value; and the negations of those five functions. In the last layer of the network, positive output values correspond to present voxels and negative values correspond to empty space (an additional signum function is applied). The largest connected component of voxels was taken to be the structure. Alteration to edge weights and/or changes in node-encoded functions alters the structure output by the network. For more details, see (69).

When encoding body shape, for the main experiments within a flat petri dish, networks were restricted to removing vertical columns of voxels along the z axis, at particular positions in (x,y), from the default spheroid, rather than removing individual voxels. This ensured that, if a simulated shape were to be instantiated as a physical reconfigurable organism, organisms could be rapidly shaped using coarse subtraction, instead of sculpting intricate 3D concavities into each one (10). Similarly, when encoding terrain, only one-voxel tall structures (z=0) were considered so that all of the immovable black voxels rested on the bottom of the dish. Thus, in both cases, only the x and y coordinates need to be input to the encoding network.

Measuring the amount of self replication. The amount of self replication achieved by a specific body shape or terrain can be measured by the number of filial generations (g) they generate. The fitness, f, of a CPPN is computed as:

$$f = s/p + g, \qquad \text{(Eqn. 1)}$$

where s is the size of the largest pile (the number of voxels it contains) at the end of the evaluation period; p is the pile size threshold required for a pile to develop into an organism (if s is greater than p, a new filial generation begins, otherwise the evaluation period ends); and g is the number of filial generations achieved. A conservative threshold (s=108 voxels) of two-thirds the size of the simulated wild type spheres (161 voxels) was selected such that relatively few randomly generated swarms achieved g>0. This significantly reduced the computational effort required to find viable terrains and body shapes that increase the amount of self replication. It also matched the observation that physical swarms composed of the wild type spheroids usually only managed one generation of replication.

Optimization algorithm. CPPNs were optimized to output replicator shapes, or terrains, that cause more self replication than that observed in the wild type spheroids. An evolutionary algorithm was used because the authors have considerable experience using this particular algorithm to evolve soft robots and reconfigurable organisms in previous work. Many optimization methods could be adapted for optimizing CPPNs, but derivative-free optimization methods such as evolutionary algorithms are a natural choice for this problem because the relationship between behavior and morphology was modeled using a nondifferentiable physical simulator. More specifically, low self replicative ability cannot yet be localized to specific missing parts of specific piles. These missing pile parts in turn cannot yet be propagated back through the physical simulator to implicate movement patterns of specific swarm members, and back further to specific parts of the replicators' bodies causing those movements. Finally, implicated body parts cannot be propagated back further into the CPPN, to implicate specific edges and nodes that should be tuned to rectify the low replicative ability. In addition, evolutionary rather than learning algorithms are desirable because initial conditions of the system (body shapes, terrains) are optimized here, rather than optimizing the control of each organism.

The evolutionary algorithm used here is a multiobjective optimization algorithm (38) that continuously injects new design alternatives into the population, and reduces selection pressure on newer designs, in order to favor the evolution of new, different ways to achieve self replication. Each independent evolutionary trial starts with its own unique set of 16 initially random CPPNs, and a sequence of random (but static) cilia forces (described in Sect. S2.1). Each CPPN is translated into a swarm, or a terrain for the default swarm of spheroids. The swarm is simulated and its self replicative ability is measured. A modified copy is made of all 16 CPPNs in the population, and each copy inherits the lineage age of its parent CPPN. A mutation adds, removes, or modifies one of the network's edges or vertices. Vertex modification involves replacing the activation function currently encoded there with a function randomly selected from the following set: sine, signum, square, absolute value, square root of the absolute value. The age of each of the 32 CPPNs is incremented by one, and one new CPPN with a lineage age of zero is randomly generated. The 17 new swarms produced by the 17 new CPPNs are evaluated in silico, as described in Sect. S2.2. Then, the entire population of 16+17=33 CPPNs are then sorted, on the basis of their age and fitness scores (Eqn. 1), into Pareto fronts. The first Pareto front consists of the youngest and most fit CPPNs, which are by definition nondominated. The second Pareto front consists of CPPNs that are dominated by at least one CPPN in the first front, but are not dominated by any other CPPNs. The N-th front consists of CPPNs that are dominated only by CPPNs the preceding N−1 fronts. Starting with the first Pareto front, successive fronts are kept in their entirety until doing so would overfill the population past its original size, 16 CPPNs, at which point CPPNs are added stochastically with probability proportional to their fitness until the population contains 16 CPPNs.

When evolving body shape, 49 independent evolutionary trials were conducted. Each evolutionary trial started with its own unique set of random shape-encoding CPPNs and sets of random cilia forces, yielding 49 champion swarms: the body shape that achieved the highest value of Eqn. 1 above, in each trial.

Runtime. Each evolutionary trial was conducted using eight NVIDIA Tesla V100s for a maximum of 48 hours wall-clock time or 500 updates of the CPPN population (whichever came first). The runtime varies due to the algorithm's stochasticity; some swarms produce more filial generations than others and thus require more time to simulate. Because evaluating swarms in simulation is the computational bottleneck, the algorithm is readily parallelizable: doubling the number of GPUs would allow halving the wall-clock time for the same population size, or doubling the size of the CPPN population that can be evaluated using the same amount of wall-clock time.

3.3. Inhibiting and Recovering Self Replication.

A simple way to stop kinematic self replication is to stop supplying the system with additional building materials (here, dissociated stem cells). This is one of the reasons that kinematic self replication is inherently more controllable than the other nine known forms of biological replication. Another way to slow or halt a kinematic self-replicator is to impede its movement in a cluttered environment.

Cluttered environment. To investigate whether the evolutionary algorithm could impart self replication to a system otherwise incapable of it, a cluttered environment was created by attaching a sparse uniform grid of immovable black voxels to the bottom of the dish (FIG. 20). The simulated wild type reconfigurable organisms could no longer spontaneously self-replicate in this environment because their movement is contained within a small region surrounding their starting position (FIG. 20A). However, if sections are removed from the simulated organisms' ventral surfaces, they can glide over the top of the static debris (FIG. 20B-D). The challenge here is to not only regain movement, but to recover self replication. This requires carving away voxels on the ventral surface of a body shape while retaining the ability to capture and aggregate dissociated cells into piles. Thus, instead of carving away entire columns at a time (which simplifies manufacture), independent removal of any voxel within the sphere was permitted.

4. Statistical Analysis.
4.1. Size of Offspring.

In silico. Five hundred simulations were conducted in which two groups—the wild type spheroids and the evolved semitoroids—built piles. In each simulation, the swarm moved differently, as each member was driven by different random cilia forces. The simulations were terminated before any piles could develop into F1 organisms. The null hypothesis is that the average size of the piles built by the spheroids was no different from the size of those built by the optimized shape (the semi-torus). Because the same random cilia forces were used for the spheres and the evolved shape, the two samples are dependent. Thus, a Wilcoxon test was performed, resulting in p=3.9*10-5 (W=6311.5). Controlling for false discovery rate, the null hypothesis is rejected at the 0.0001 level of significance.

In vivo. The sizes of the 10 largest physical F1 offspring generated by each of eight different swarms was recorded. Five of the swarms were composed of wild type spheroids, one was composed of spheroids double the size, and one was composed of flattened spheroids (gray points in FIG. 9E). Each swarm behaved within a dish with differing dissociated cell density. The sizes of the 10 largest physical F1 offspring generated by each of three additional swarms, composed of the automatically designed semitoroid, were also recorded, again at different dissociated cell densities (pink points in FIG. 9E). Within each set of 10, the size of the offspring was divided by the cell density in which they were built. The null hypothesis is that the average diameter of the offspring (normalized by cell concentration) built by semitoroids progenitors across three independent trials was no different than the average diameter of the offspring built across five independent trials by the wild type spheroids or spheroid variants. Comparing offspring size in this way is a conservative test since the volumetric difference between two spheres is eight times as large as their corresponding difference in diameter. A Mann Whitney U test was performed, resulting in p=0.0368 (U=1.0). Controlling for false discovery rate, the null hypothesis is rejected at the 0.05 level of significance.

4.2. Number of Generations.

In silico. The 49 evolutionary trials resulted in progenitor shapes that self-replicated for two to three generations in silico, under strict conditions: a pile size threshold of two thirds the number of voxels contained within the simulated wild type spheres. Two thirds is a strict threshold because the best estimate is closer to one fourth (see Table 1). All 49 trials were compared to evaluations of spheres. The wild type spheres did not self replicate for more than a single generation, in any of the 49 trials. Bootstrapped confidence intervals of the 49 best swarms from each trial were compared against 49 of the wild type spheroid swarms to determine the probability of overlap (FIG. 17A). Controlling for false discovery rate the null hypothesis is rejected at the 0.0001 level of significance.

The same procedure was performed for terrain optimization with wild type spheroid swarms in silico (FIG. 18). The null hypothesis is that of no difference in the number of filial generations produced by swarms operating on the best evolved terrains (e.g. FIG. 19) and those operating on the flat surface plane of a standard petri dish (e.g. FIG. 15). Based on the bootstrapped confidence intervals, and controlling for false discovery rate, the null hypothesis is rejected at the 0.0001 level of significance.

In vivo. The wild type reconfigurable organisms produced just a single filial generation in four of the five independent trials. The only trial to produce two generations of offspring required the highest cell concentration we tested (150 cells/mm$^2$). In the first of three self replication trials using the optimized body shape (semitoroids) resulted in two generations at 61 cells/mm$^2$ but then degraded into immobility due to a fungal infection. In the second and third trials using the optimized body shape, additional precautions were taken to avoid fungal infections. Three successive generations of offspring were produced at 61 cells/mm$^2$; four successive generations of offspring were produced at 91 cells/mm². The null hypothesis is that the number of generations of self replication achieved by the optimized design (2 g, 3 g, 4 g) was no greater than the number of generations produced by the wild type spheroids (1 g, 1 g, 1 g, 1 g, 2 g). A Mann Whitney U test was performed: p=0.0188. (U=0.5). Controlling for false discovery rate, the null hypothesis is rejected at the 0.05 level of significance.

4.3. Correlation Between First Generation Size and Total Number of Generations in Vivo.

There was a Spearman rank-order correlation coefficient of 0.9322 (p=0.000'74) between the number of replication generations achieved and the aggregate size of the 10 largest first generation offspring.

5. Utility Forecast.

A computational model was created to predict the amount of utility (useful work) the self-replicating swarm may be capable of, if it was provided with reachable but unassembled parts in a semi-structured environment. To that end, a circuit completion task was chosen. This section details how the parameters were estimated for the self-replicating swarm and the electronic parts. The model incorporates many biological details from the physical reconfigurable organisms reported here, and from emerging microscale electronic components. But, many of the details estimated in the model will be refined when more is known about how such organisms can or cannot interact with various microscale environments containing artificial materials. This will, in future, yield better forecasts of the potential utility of this technology.

5.1. Circuit Components.

Three types of modular microelectronic components were simulated: light emitters, batteries, and wire. Each component contains vertically stacked and insulated conductors, which maintains connectability under translational and rotational movement in plane (FIG. 22C-E). That is, the electronic components, if resting on a surface plane, can be pushed together and connected by a swarm of reconfigurable organisms that move along the same surface. The simulated wires (blue voxels in FIG. 22A) adhere to each other upon collision like the simulated dissociated stem cells do (green voxels). Except, once the wires attach, they do not detach (there is no stochastic spherification as in the stem cells). Current emanates from a power source that could, if instantiated physically, be supplied by a microbattery or electrodes, and is approximated in simulation by passing discrete packets of voltage along neighboring voxels in a chain of connected voxels. If a packet of voltage reaches a light emitter, it is switched on, permanently.

There exist atomically-thin light emitters with light emission visible to the naked eye that are made of just a few layers of graphene, stretched across a 2D sheet <5 μM in length and width and powered at ~0.4 V $\mu m^{-1}$ (27). Any organisms gathering and connecting these emitters to a power supply would have to be removed or sacrificed before powering the circuit. The number of switched-on light emitters was chosen here as the unit of "useful work" performed by a self-replicating swarm, but the choice was arbitrary. There are other kinds of microscale resistors, such as transistors, which could be used instead, or any number of other kinds of microscale inspection, maintenance or assembly tasks.

5.2. Estimated Utility.

Task environment. Sixteen initially disconnected strips of vertically stacked and insulated conductive voxels ("wires"; blue voxels) are spread out along the edge of the soft boundary of a simulated dish (FIGS. 11 and 22). In each corner, two of the strips are connected at a 90 degree angle to a small light emitter (white voxels). Two of the remaining eight strips along the edge, on opposing sides, are attached to power supplies. Nine reconfigurable organisms are placed in the center of the simulated dish amid a grid of dissociated stem cells. Twelve additional strips of vertically-insulated conductive voxels are placed among them, randomly oriented north-south or east-west with equal probability (FIG. 11B,C). Potential current flow is shown in yellow propagating down blue conductive voxels connected to a power supply. As organisms move in their dish, they self replicate (by building piles out of dissociated stem cells) and, simultaneously, snap together the conductive strips of voxels in the dish as a side effect of movement. If one of the corner strips with a light emitter connects by conductive voxels to one of the two power supplies, the light emitter switches on (as indicated by a red circled X in FIGS. 11 and 22).

The swarm builds piles, which, if sufficiently larger than 40 voxels, develop into offspring, and the dissociated cells are replenished, every 3.5 seconds, as in the above experiments. Forty voxels is one fourth the size of the simulated wild type spheroids, which is the best estimate for the minimum size of piles that developed into self motile offspring in vivo (Table 1). Because utility is measured rather than self replication, the parents are left in the dish and continue building additional filial generations alongside their offspring for 17.5 seconds. As the 3 organisms move they randomly push the circuit components into place, occasionally turning on up to four light emitters. After 17.5 seconds of simulation time, the parents were removed, and the offspring were extracted. To better approximate the spherification that occurs in vivo, offspring extracted from a completed simulation are converted to spheroids containing roughly the same number of voxels. The spherified offspring were then split into two subgroups, each subgroup was injected into one of two new simulated petri dishes, and each new dish contains a new partially-completed circuit. Self replication and circuit building begin afresh in these two dishes, again for 17.5 seconds. This process triggers the growth of a binary simulation tree (FIG. 11) in which each simulation begets at most two simulation branches, each containing one half of the produced offspring of their root simulation. If only a single offspring is created by a swarm after 17.5 seconds, then only one new simulation branch is spawned. If no offspring were built, then that branch of the binary simulation tree dies out.

Growth rate of utility. After 50 simulation bifurcations (875 seconds of simulation time), 5024 light emitters were switched on by the self-replicating swarm.

Symbolic regression (42) was used to find the degree of a polynomial function that best explains the cumulative number of emitters switched on by the self-replicating swarm. The regression operators were limited to addition and multiplication. The operands were the number of simulation bifurcations (a sequence from 1 to 51), and an ephemeral constant drawn from a gaussian distribution (mu=0, sigma=10). Each candidate solution is evaluated based on its root mean squared error (RMSE) with the cumulative number of emitters switched on at each simulation bifurcation.

A population of 1000 candidate equations was optimized for 1000 generations using the same optimization algorithm (38) used to design body shapes and terrains. The population size could be set much larger for this experiment because evaluating equations takes milliseconds whereas evaluating self-replicating swarms takes minutes. Ten independent optimization trials were conducted, each starting from a different random set of 1000 candidate equations. The objective is to minimize root mean squared error. After 1000 generations, the least-error equations found in each trial all converged about the quadratic curve derived by ordinary least squares: 2.7x 2-43x+182.4, where x is the number of simulation bifurcations (R2=0.9988). The prediction of the model is thus, under the simulated conditions, utility increases quadratically with time.

Self replication (and thus utility) could, in principle, be enhanced in vivo through numerous bioengineering and molecular interventions, including: altering cell adherence properties (through the expression of cadherins or integrins), increasing cell lifespan with culture media, increasing swimming velocity by altering the number and polarity of cilia, changing cilia beat frequency, generating larger parents, increasing the number of adults during self replication, provision of more feeder cells, altering the size of the arena, and changing the substrate on which self replication occurs (increased or decreased friction). For the current settings of these parameters, and others that could affect the rate of utility produced by future reconfigurable organisms, see Table 1.

It is clear that, in theory, self-replicative machines that perform useful work as a side effect will superlinearly increase in utility over time. However, it was not clear that there exists a domain in which the randomly-acting self-replicative system described here would be so. The flexible electronics technology simulated here demonstrates that, assuming such technology comes to fruition, there may soon be a domain in which our technology may be superlinearly useful over time.

TABLE 2

The sizes of the largest first generation offspring, and the total number of generations of self replication produced for eight independent trials here.

| Shape | sphere | sphere | sphere | C-shape | 2 × sphere | flattened sphere |
|---|---|---|---|---|---|---|
| Cell Density (cell/mm$^2$) | 25 | 75 | 150 | 61 | 52 | 105 |
| 1 | 0.150529 | 0.31482 | 0.462979 | 0.4521711 | 0.2709368 | 0.5708763 |
| 2 | 0.150529 | 0.30909 | 0.374610 | 0.4222342 | 0.2563316 | 0.2848421 |
| 3 | 0.144521 | 0.28793 | 0.311415 | 0.3721605 | 0.2349632 | 0.2837237 |
| 4 | 0.127189 | 0.28328 | 0.301657 | 0.3390132 | 0.2306789 | 0.2662974 |
| 5 | 0.122757 | 0.22929 | 0.296657 | 0.3316211 | 0.2193553 | 0.253071 |
| 6 | 0.115907 | 0.21604 | 0.284842 | 0.31915 | 0.1972816 | 0.2336026 |
| 7 | 0.111897 | 0.20854 | 0.283428 | 0.3051737 | 0.1907842 | 0.2221158 |
| 8 | 0.110652 | 0.19352 | 0.27555 | 0.294971 | 0.185410 | 0.218342 |
| 9 | 0.105918 | 0.16718 | 0.253179 | 0.277902 | 0.184210 | 0.215852 |
| 10 | 0.100552 | 0.16526 | 0.252247 | 0.271702 | 0.182473 | 0.210657 |
| average | 0.124045 | 0.2375 | 0.309656 | 0.33861 | 0.215242 | 0.275938 |
| stdev | 0.0185808 | 0.056967 | 0.0640444 | 0.060209 | 0.0321140 | 0.1073014 |
| generations produced | 1 | 1 | 2 | 3 | 1 | 1 |

| Shape | C-shape* | no parent | no parent | no parent | no parent |
|---|---|---|---|---|---|
| Cell Density (cell/mm$^2$) | 61 | 91 | 61 | 83 | 150 |
| 1 | 0.4383921 | 0.6386021 | 0.07590 | 0.07316 | 0.078242 |
| 2 | 0.3548237 | 0.4772063 | 0.071828 | 0.071102 | 0.074105 |
| 3 | 0.3314105 | 0.4711292 | 0.071052 | 0.063268 | 0.072260 |
| 4 | 0.3000474 | 0.4204208 | 0.066418 | 0.059136 | 0.069526 |
| 5 | 0.2992605 | 0.41675 | 0.064513 | 0.057894 | 0.067247 |
| 6 | 0.2852816 | 0.3883958 | 0.064084 | 0.053673 | 0.068989 |
| 7 | 0.2686263 | 0.3793729 | 0.063157 | 0.052697 | 0.065789 |
| 8 | 0.26635 | 0.3611813 | 0.061434 | 0.049652 | 0.059663 |
| 9 | 0.2570342 | 0.3286396 | 0.061434 | 0.047442 | 0.058431 |
| 10 | 0.2542158 | 0.323275 | 0.061378 | 0.047442 | 0.058431 |
| average | 0.3055442 | 0.420497 | 0.066120 | 0.057547 | 0.067068 |
| stdev | 0.0568754 | 0.092792 | 0.005106 | 0.009238 | 0.006774 |
| generations produced | 2 | 4 | 0 | 0 | 0 |

*contamination

SUPPLEMENTAL REFERENCES FOR EXAMPLE 3

1. Kamm, R. D., Bashir, R., Arora, N., Dar, R. D., Gillette, M. U., Griffith, L. G., Kemp, M. L., Kinlaw, K., Levin, M., Martin, A. C. and McDevitt, T. C. Perspective: The promise of multi-cellular engineered living systems. APL Bioengineering, 2, 040901 (2018).
2. Garreta, E., Kamm, R. D., de Sousa Lopes, S. M. C., Lancaster, M. A., Weiss, R., Trepat, X., Hyun, I. and Montserrat, N. Rethinking organoid technology through bioengineering. Nature Materials, 20, 145-155 (2021).
3. Huh, D., Matthews, B. D., Mammoto, A., Montoya-Zavala, M., Hsin, H. Y. and Ingber, D. E. Reconstituting organ-level lung functions on a chip. Science 328, 1662-1668 (2010).
4. Wu, Q., Liu, J., Wang, X., Feng, L., Wu, J., Zhu, X., Wen, W. and Gong, X. Organ-on-a-chip: Recent breakthroughs and future prospects. Biomedical Engineering Online, 19, 1-19 (2020).

5. Losner, J., Courtemanche, K. & Whited, J. L. A cross-species analysis of systemic mediators of repair and complex tissue regeneration. npj Regen Med 6, 21 (2021).
6. Hussey, G. S., Dziki, J. L. and Badylak, S. F. Extracellular matrix-based materials for regenerative medicine. Nature Reviews Materials, 3, 159-173 (2018).
7. Han, Y., Li, X., Zhang, Y., Han, Y., Chang, F. and Ding, J. Mesenchymal stem cells for regenerative medicine. Cells, 8, 886 (2019).
8. Gilbert, S. F., Sarkar, S. Embracing complexity: organicism for the 21st century. Developmental Dynamics, 219, 1-9 (2000).
9. Blackiston, D., Lederer, E., Kriegman, S., Gamier, S., Bongard, J., Levin, M. A cellular platform for the development of synthetic living machines. Science Robotics 6, eabf1571 (2021).
10. Kriegman, S., Blackiston, D., Levin, M., Bongard, J. A scalable pipeline for designing reconfigurable organisms. Proceedings of the National Academy of Sciences 117, 1853-1859 (2020).
11. Jones, E. A., & Woodland, H. R. Development of the ectoderm in *Xenopus*: tissue specification and the role of cell association and division. Cell, 44, 345-355 (1986). 14
12. Kim, H. Y., Jackson, T. R., Stuckenholz, C., Davidson, L. A. Tissue mechanics drives regeneration of a mucociliated epidermis on the surface of *Xenopus* embryonic aggregates. Nature Communications, 11, 1-10 (2020).
13. Walentek, P. Manipulating and analyzing cell type composition of the *Xenopus* mucociliary epidermis. *Xenopus,* 251-263 (2018). Humana Press, New York, N.Y.
14. Stubbs, J. L., Davidson, L., Keller, R., Kintner, C. Radial intercalation of ciliated cells during *Xenopus* skin development. Development, 133, 2507-2515 (2006).
15. von Neumann, J. Theory of self-reproducing automata, Ed. Burks, A. W., University of Illinois Press (1966).
16. Ray, T. S., Evolution, complexity, entropy and artificial reality. Physica D: Nonlinear Phenomena, 75, 239-263 (1994).
17. Chou, H. H. and Reggia, J. A. Emergence of self-replicating structures in a cellular automata space. Physica D: Nonlinear Phenomena, 110, 252-276 (1997).
18. Studer, G. and Lipson, H. Spontaneous emergence of self-replicating structures in molecube automata. In Proc. of the 10th Int. Conf. on the Simulation and Synthesis of Living Systems, 227-233 (2006).
19. Penrose, L. S. Self-reproducing machines. Scientific American, 200, 105-117 (1959).
20. Jacobson, H. On models of reproduction. American Scientist, 46, 255-284 (1958).
21. Chirikjian, G. S., Zhou, Y., Suthakorn, J. Self-replicating robots for lunar development. IEEE Transactions on Mechatronics, 7, 462-472 (2002).
22. Zykov, V., Mytilinaios, E., Adams, B., Lipson, H. Self-reproducing machines. Nature, 435, 163-164 (2005).
23. Griffith, S., Goldwater, D. & Jacobson, J. Self-replication from random parts. Nature, 437, 636 (2005).
24. Adams, B. and Lipson, H. A universal framework for analysis of self-replication phenomena. Entropy, 11, 295-325 (2009).
25. Chirikjian, G. S. Parts entropy and the principal kinematic formula. In Procs. of the IEEE Intl. Conf. on Automation Science and Engineering, 864-869 (2008). 10.1109/COASE.2008.4626465
26. Qu, Zhe, et al. Towards high-performance microscale batteries: Configurations and optimization of electrode materials by in-situ analytical platforms. Energy Storage Materials, 29, 17-41 (2020).
27. Kim, Y., Kim, H., Cho, Y. et al. Bright visible light emission from graphene. Nature Nanotech 10, 676-681 (2015).
28. Gao, W., Ota, H., Kiriya, D., Takei, K., & Javey, A. Flexible electronics toward wearable sensing. Accounts of Chemical Research, 52, 523-533 (2019). 15
29. Ricotti, L., Trimmer, B., Feinberg, A. W., Raman, R., Parker, K. K., Bashir, R., Sitti, M., Martel, S., Dario, P. and Menciassi, A. Biohybrid actuators for robotics: A review of devices actuated by living cells. Science Robotics, 2, eaaq0495 (2017).
30. Park, S. J., Gazzola, M., Park, K. S., Park, S., Di Santo, V., Blevins, E. L., Lind, J. U., Campbell, P. H., Dauth, S., Capulli, A. K. and Pasqualini, F. S., Phototactic guidance of a tissue-engineered soft-robotic ray. Science, 353, 158-162 (2016)
31. Maury, C. P. J. Amyloid and the origin of life: self-replicating catalytic amyloids as prebiotic informational and protometabolic entities. Cellular and Molecular Life Sciences, 75, 1499-1507 (2018).
32. Tank, E. M., Harris, D. A., Desai, A. A., & True, H. L. Prion protein repeat expansion results in increased aggregation and reveals phenotypic variability. Molecular and Cellular Biology, 27, 5445-5455 (2007).
33. Boer, M. M., de Dios, V. R. and Bradstock, R. A. Unprecedented burn area of Australian mega forest fires. Nature Climate Change, 10, 171-172 (2020).
34. Emanuel, K. Increasing destructiveness of tropical cyclones over the past 30 years. Nature, 436, 686-688 (2005).
35. Lin, N., Kopp, R. E., Horton, B. P. and Donnelly, J. P. Hurricane Sandy's flood frequency increasing from year 1800 to 2100. Proceedings of the National Academy of Sciences, 113, 12071-12075 (2016).
36. Liu, Y. Y., Slotine, J. J. and Barabási, A. L. Controllability of complex networks. Nature, 473, 167-173 (2011).
37. Nieuwkoop, P. D., & Faber, J. Normal table of *Xenopus laevis,* 252 (1994).
38. Schmidt, M., Lipson, H. Age-fitness pareto optimization. Genetic Programming Theory and Practice VIII, 129-146 (2011).
39. Stanley, K. O. Compositional pattern producing networks: a novel abstraction of development. Genetic Programming and Evolvable Machines 8, 131-162 (2007).
40. Hiller, J. and Lipson, H. Dynamic simulation of soft multimaterial 3D-printed objects. Soft Robotics, 1, 88-101 (2014).
41. Benjamini, Y., Hochberg, Y. Controlling the false discovery rate: A practical and powerful approach to multiple testing. Journal of the Royal Statistical Society: Series B (Methodological), 57, 289-300 (1995).
42. Schmidt, M., Lipson, H. Distilling free-form natural laws from experimental data. Science, 324, 81-85 (2009).
43. Müller, H. A. J., Hausen, P. Epithelial cell polarity in early *Xenopus* development. Developmental Dynamics, 202, 405-420 (1995).
44. Deblandre, G. A., Wettstein, D. A., Koyano-Nakagawa, N., Kintner, C. A two-step mechanism generates the spacing pattern of the ciliated cells in the skin of *Xenopus* embryos. Development, 126, 4715-4728 (1999). 16
45. Werner, M. E., Mitchell, B. J. Understanding ciliated epithelia: the power of *Xenopus*. Genesis, 50, 176-185 (2012).
46. Walentek, P., Bogusch, S., Thumberger, T., Vick, P., Dubaissi, E., Beyer, T., Blum, M. and Schweickert, A. A novel serotonin-secreting cell type regulates ciliary motil- 46. ity in the mucociliary epidermis of *Xenopus* tadpoles. Development, 141, 1526-1533 (2014).
47. Dubaissi, E., Rousseau, K., Lea, R., Soto, X., Nardeosingh, S., Schweickert, A., Amaya, E., Thornton, D. J., Papalopulu, N. A secretory cell type develops alongside multiciliated cells, ionocytes and goblet cells, and provides a protective, anti-infective function in the frog embryonic mucociliary epidermis. Development, 141, 514-1525 (2014).
48. Walentek, P., & Quigley, I. K. What we can learn from a tadpole about ciliopathies and airway diseases: Using systems biology in *Xenopus* to study cilia and mucociliary epithelia. Genesis, 55, e23001 (2017).
49. Kim, S. K., Zhang, S., Werner, M. E., Brotslaw, E. J., Mitchell, J. W., Altabbaa, M. M., Mitchell, B. J. CLAMP/Spef1 regulates planar cell polarity signaling and asymmetric microtubule accumulation in the *Xenopus* ciliated epithelia. Journal of Cell Biology, 217, 1633-1641 (2018).
50. Angerilli, A., Smialowski, P., & Rupp, R. A The *Xenopus* animal cap transcriptome: building a mucociliary epithelium. Nucleic Acids Research, 46, 8772-8787 (2018).
51. Chuyen, A., Rulquin, C., Daian, F., Thome, V., Clement, R., Kodjabachian, L., Pasini, A. The Scf/Kit pathway implements self-organized epithelial patterning. Developmental Cell, 56, 795-810 (2021).
52. Green, J. B., Smith, J. C. Graded changes in dose of a *Xenopus* activin A homologue elicit stepwise transitions in embryonic cell fate. Nature, 347, 391-394 (1990).
53. Thomsen, G., Woolf, T., Whitman, M., Sokol, S., Vaughan, J., Vale, W., Melton, D. A. Activins are expressed early in *Xenopus* embryogenesis and can induce axial mesoderm and anterior structures. Cell, 63, 485-493 (1990).
54. Thomsen, G. H., Melton, D. A. Processed Vg1 protein is an axial mesoderm inducer in *Xenopus*. Cell, 74, 433-441 (1993).
55. Gurdon, J. B., Harger, P., Mitchell, A., Lemaire, P. Activin signalling and response to a morphogen gradient. Nature, 371, 487-492 (1994).
56. Ariizumi, T., Asashima, M. In Vitro Control of the Embryonic Form of *Xenopus laevis* by Activin A: Time and Dose-Dependent Inducing Properties of Activin-Treated Ectoderm: (activin/ectoderm/organizer/*Xenopus laevis*/neural induction). Development, Growth & Differentiation, 36, 499-507 (1994).
57. Sasai, Y., Lu, B., Piccolo, S., De Robertis, E. M. Endoderm induction by the organizer-secreted factors chordin and noggin in *Xenopus* animal caps. The EMBO Journal, 15, 4547-4555 (1996). 17
58. Miyanaga, Y., Shiurba, R., Asashima, M. Blood cell induction in *Xenopus* animal cap explants: effects of fibroblast growth factor, bone morphogenetic proteins, and activin. Development Genes and Evolution, 209, 69-76 (1999).
59. Ariizumi, T., Takahashi, S., Chan, T. C., Ito, Y., Michiue, T., Asashima, M. Isolation and differentiation of *Xenopus* animal cap cells. Current Protocols in Stem Cell Biology, 9, 1D-5 (2009).
60. Ariizumi, T., Michiue, T., Asashima, M. In Vitro Induction of *Xenopus* Embryonic Organs Using Animal Cap Cells. Cold Spring Harbor Protocols, pdb-prot097410 (2017).
61. Teegala, S., Chauhan, R., Lei, E., Weinstein, D. C. Tbx2 is required for the suppression of mesendoderm during early *Xenopus* development. Developmental Dynamics, 247, 903-913 (2018).
62. Marnellos, G., Deblandre, G. A., Mjolsness, E., Kintner, C. Delta-Notch lateral inhibitory patterning in the emergence of ciliated cells in *Xenopus*: experimental observations and a gene network model. In Biocomputing 2000, 329-340 (1999).
63. Stubbs, J. L., Oishi, I., Belmonte, J. C. I., Kintner, C. The forkhead protein Foxj 1 specifies node-like cilia in *Xenopus* and zebrafish embryos. Nature Genetics, 40, 1454-1460 (2008).
64. Quigley, I. K., Stubbs, J. L., Kintner, C. Specification of ion transport cells in the *Xenopus* larval skin. Development, 138, 705-714 (2011).
65. Myers, C. T., Appleby, S. C., Krieg, P. A. Use of small molecule inhibitors of the Wnt and Notch signaling pathways during *Xenopus* development. Methods, 66, 380-389 (2014).
66. Brooks, E. R., Wallingford, J. B. Multiciliated cells. Current Biology, 24, R973-R982 (2014).
67. Liu, S., Matthews, D., Kriegman, S., Bongard, J. Voxcraft-sim, a GPU-accelerated voxel-based physics engine. 10.5281/zenodo.3835152, https://github.com/voxcraft/voxcraft-sim (2020).
68. Karras, T. Maximizing parallelism in the construction of BVHs, octrees, and k-d trees. In Procs. of the ACM Conf. on High-Performance Graphics, 33-37 (2012).
69. Cheney, N., et al. Unshackling evolution: Evolving soft robots with multiple materials and a powerful generative encoding." In Procs. of the Genetic and Evolutionary Computation Conf. (2013).

Example 4—Control of Locomotion in Engineered Living Systems

Biological robots are currently limited by their lack of autonomy: actuation/movement, where available, requires remote controlled stimulation of specific cell populations, and currently no closed loop autonomous systems exist. We have developed a new approach to control movement/behavior in engineered biological robots, through the utilization of motile cilia, small hairlike structures present on the surface of cells which beat in unison to generate fluid flow.

This new advance in the autonomous control of movement involves the expression of light sensitive optogenetic proteins in motile cilia containing cell populations. These optogenetic proteins "open" and "close" in response to specific wavelengths of light, which in turn changes the charge [voltage] of the cell. In response to voltage changes, the beat frequency of motile cilia increases or decreases, which could directly alter biological robot movement.

Figure 23:
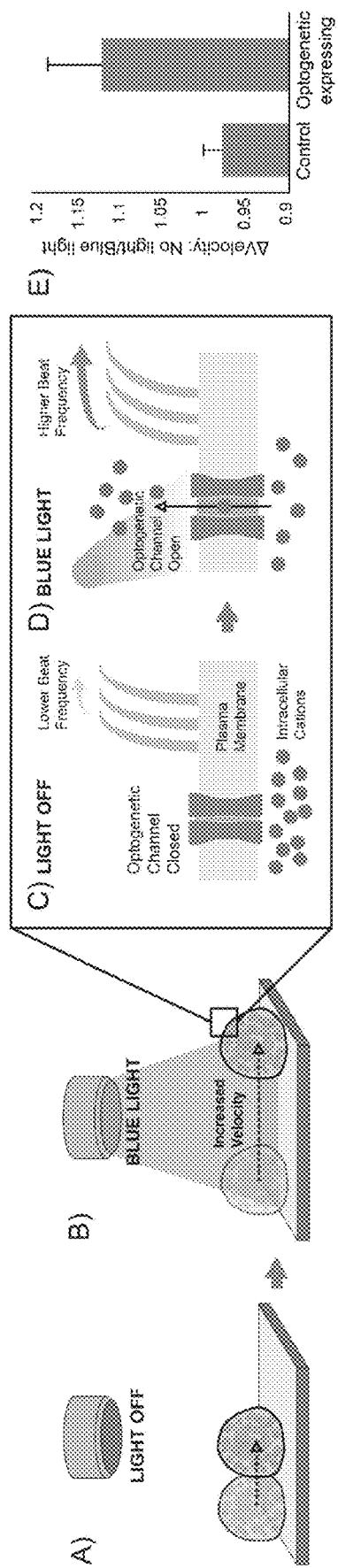
FIG. 23. Stimulation of optogenetic channels with blue light increases biological robot velocity. The optogenetic channel ChR2 was expressed in ciliated designs and velocity was computed over 20 seconds of non-stimulating green light, followed by 20 seconds of channel stimulating blue light (A, B). Upon stimulation the ChR2 channels open allowing cations to exit the cell, which has been hypothesized to increase cilia beat frequency and thus velocity (C, D). (E) In a set of wet-lab experiments, biological robots expressing the optogenetic channel showed a significant increase in velocity in response to light stimulation, compared to untreated controls (paired t-test, p=0.0124, n=8 individuals per treatment).

To demonstrate these channels can be used to control cilia beating, and thus robot velocity, we expressed a common optogenetic channel, channelrhodopsin-2 [ChR2], in our biological robots via mRNA microinjection. This channel is "activated" in response to blue light and remains closed at other wavelengths or in darkness. The velocity of 8 individuals were measured over a period of 40s, with blue light being present only during the latter 20 seconds of observation (FIG. 23 A-D), delivered by a SMZ-1500 fluorescent microscope equipped with 467-498 nm filter. Untreated controls showed no change in velocity in response to blue light, however, ChR2 expressing designs showed a significant increase in velocity in response to light stimulus (FIG. 23E, t-test, p=0.0124, n=8 individuals per treatment). These data are the first to show control of cilia beating with light, and that it is thus possible to control the movement of engineered biological robots within aqueous environments.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

All methods described herein can be performed in any suitable order unless otherwise indicated herein or otherwise clearly contradicted by context. The use of any and all examples provided herein, is intended merely to better illuminate the invention and does not pose a limitation on the scope of the invention unless otherwise claimed. No language in the specification should be construed as indicating any non-claimed element as essential to the practice of the invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. An engineered multicellular organism comprising an aggregate of ciliated *Xenopus laevis* (*X. laevis*) cells derived from fertilized *X. laevis* embryonic cells, wherein the cilia of the ciliated cells move the organism at a rate of at least 15 microns/second in an aqueous environment.

2. The organism of claim 1, wherein the organism consists of biological material and/or does not comprise any inorganic material.

3. The organism of claim 1, wherein the organism comprises a sensor for detecting a target molecule.

4. The organism of claim 1, wherein the cells of the organism self-assemble.

5. The organism of claim 1, wherein the organism has an effective diameter of about 100-500 microns.

6. The organism of claim 1, wherein the organism does not comprise neural cells or neural tissue.

7. The organism of claim 1, wherein the ciliated cells are *X. laevis* epidermal cells.

8. The organism of claim 1, wherein the ciliated cells are engineered to express a heterologous molecule.

9. The organism of claim 8, wherein the heterologous molecule is a reporter molecule.

10. The organism of claim 8, wherein the heterologous molecule is an enzyme that metabolizes a target substrate.

11. The organism of claim 8, wherein the heterologous molecule is a receptor for a target ligand.

12. The organism of claim 1, wherein the aggregate of cells reaggregates after the aggregate is subjected to deaggregation.

13. The organism of claim 1, wherein the organism is capable of moving a target object.

14. The organism of claim 1, wherein the organism comprises a cavity for capturing and/or transporting a target object.

15. A plurality of the organism of claim 1, wherein the plurality exhibits collective and/or coordinated behavior.

16. The plurality of claim 15, wherein the collective and/or coordinated behavior is collective and/or coordinated movement.

17. A method for preparing the engineered multicellular organism of claim 1 or a plurality thereof, the method comprising explanting stem cells derived from fertilized *X. laevis* embryonic tissue and culturing the explanted cells under conditions in which the cultured, explanted cells form the engineered multicellular organism or the plurality thereof, wherein the conditions comprise culturing the explanted cells at 14° C.

* * * * *